United States Patent
Mundy et al.

(10) Patent No.: US 9,576,198 B2
(45) Date of Patent: Feb. 21, 2017

(54) METHODS AND APPARATUS FOR IDENTIFYING SUBJECT MATTER IN VIEW DATA

(71) Applicant: Brown University, Providence, RI (US)

(72) Inventors: Joseph L. Mundy, Barrington, RI (US); Benjamin Kimia, Providence, RI (US); Philip Nathan Klein, Providence, RI (US); Kongbin Kang, Providence, RI (US); Huseyin Can Aras, Providence, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 14/706,522

(22) Filed: May 7, 2015

(65) Prior Publication Data
US 2016/0104026 A1 Apr. 14, 2016

Related U.S. Application Data

(63) Continuation of application No. 13/969,669, filed on Aug. 19, 2013, now abandoned, which is a
(Continued)

(51) Int. Cl.
*G06K 9/00* (2006.01)
*C07D 401/14* (2006.01)
(Continued)

(52) U.S. Cl.
CPC ............ *G06K 9/0055* (2013.01); *A61B 6/032* (2013.01); *A61B 6/5217* (2013.01);
(Continued)

(58) Field of Classification Search
None
See application file for complete search history.

(56) References Cited

U.S. PATENT DOCUMENTS 5,699,799 A 12/1997 Xu et al.
5,712,803 A 1/1998 Garuet-Lempirou
(Continued)

FOREIGN PATENT DOCUMENTS

JP 2004-159913 A 6/2004
WO 02/31768 A2 4/2002
(Continued)

OTHER PUBLICATIONS

N. Srinivasa, K.R. Ramakrishnan, and K. Rajgopal, "Detection of Edges from Projections", Mar. 1992, IEEE Transactions on Medical Imaging, vol. 11, No. 1, pp. 76-80.*
(Continued)

*Primary Examiner* — Atiba O Fitzpatrick
(74) *Attorney, Agent, or Firm* — Nields, Lemack & Frame, LLC

(57) ABSTRACT

In one aspect, a method and apparatus for detecting subject matter of interest in view data obtained by scanning an object including generating a filter adapted to respond to the subject matter of interest, splatting the filter onto a portion of the view data to provide a filter splat, and performing at least one operation on the portion of the view data using the filter splat to facilitate determining whether the subject matter of interest is present in the portion of the view data.

3 Claims, 34 Drawing Sheets

Related U.S. Application Data continuation of application No. 13/154,787, filed on Jun. 7, 2011, now Pat. No. 8,515,145, which is a continuation of application No. 11/299,558, filed on Dec. 9, 2005, now Pat. No. 7,978,887, which is a continuation-in-part of application No. 10/871,265, filed on Jun. 17, 2004, now Pat. No. 7,492,934.

(60) Provisional application No. 60/479,114, filed on Jun. 17, 2003.

(51) Int. Cl.
    *G06T 11/00* (2006.01)
    *G06T 17/10* (2006.01)
    *G06T 5/00* (2006.01)
    *A61B 6/00* (2006.01)
    *A61B 5/00* (2006.01)
    *A61B 6/03* (2006.01)
    *A61B 6/12* (2006.01)

(52) U.S. Cl.
    CPC ....... *C07D 401/14* (2013.01); *G06K 9/00503* (2013.01); *G06T 5/001* (2013.01); *G06T 11/008* (2013.01); *G06T 17/10* (2013.01); *A61B 5/489* (2013.01); *A61B 6/03* (2013.01); *A61B 6/12* (2013.01); *G06T 2200/04* (2013.01); *G06T 2207/10116* (2013.01); *G06T 2207/20024* (2013.01); *G06T 2207/20144* (2013.01)

(56) References Cited

U.S. PATENT DOCUMENTS

| | | | |
|---|---|---|---|
| 5,769,640 | A | 6/1998 | Jacobus et al. |
| 5,921,920 | A | 7/1999 | Marshall et al. |
| 5,966,141 | A | 10/1999 | Ito et al. |
| 6,028,907 | A * | 2/2000 | Adler .................. A61B 6/032 378/4 |
| 6,236,878 | B1 | 5/2001 | Taylor et al. |
| 6,409,760 | B1 | 6/2002 | Melvin |
| 6,434,265 | B1 | 8/2002 | Xiong et al. |
| 6,501,848 | B1 | 12/2002 | Carroll et al. |
| 6,507,633 | B1 | 1/2003 | Elbakri et al. |
| 6,915,004 | B2 | 7/2005 | Newport et al. |
| 7,043,290 | B2 | 5/2006 | Young et al. |
| 7,257,237 | B1 | 8/2007 | Luck et al. |
| 2001/0020175 | A1 | 9/2001 | Yassour et al. |
| 2002/0114503 | A1 | 8/2002 | Klotz et al. |
| 2002/0142294 | A1 | 10/2002 | Blair et al. |
| 2003/0053697 | A1 | 3/2003 | Aylward et al. |
| 2003/0076987 | A1 | 4/2003 | Wilson et al. |
| 2003/0099391 | A1 | 5/2003 | Bansal et al. |
| 2003/0187358 | A1 | 10/2003 | Okerlund et al. |
| 2004/0267114 | A1 | 12/2004 | Mundy et al. |
| 2006/0182327 | A1 | 8/2006 | Mundy et al. |

FOREIGN PATENT DOCUMENTS

| | | |
|---|---|---|
| WO | 02/066470 A1 | 8/2002 |
| WO | 03/034176 A2 | 4/2003 |
| WO | 2005/050544 A1 | 6/2005 |

OTHER PUBLICATIONS

European communication dated Jun. 27, 2006 in European patent application No. 047556295.
International Search Report dated Oct. 14, 2004 in PCT application No. PCT/US2004/019584.
International Search Report mailed Nov. 11, 2004 in PCT application No. PCT/US2004/019584.
International Search Report mailed Apr. 4, 2008 in PCT application No. PCT/US2006/047236.
International Search Report dated Oct. 6, 2009 in PCT application No. PCT/US2006/047236.
Bresler et al, "Three-Dimensional Reconstruction from Projections with Incomplete and Noisy Data by Object Estimation," Aug. 1987, IEEE Transactions on Acoustics, Speech, and Signal Processing, vol. ASSP-35, No. 8, pp. 1139-1152.
Bullitt et al, "Computer-Assisted Visualization of Arteriovenous Malformations on the Home PC," 2001, Neurosurgery, vol. 48, pp. 576-583.
Frangi et al, "Model-Based Quantization of 3-D Magnetic Resonance Angiographic Images," IEEE Transactions on Medical Imaging, vol. 18, No. 10, Oct. 1999, pp. 946-956.
Huang et al, "Generalized Tube Model: Recognizing 3D Elongated Objects from 2D Intensity Images," Proceedings CVPR, 1993, 6 pages.
Lorigo et al, "CURVES: Curve Evolution for Vessel Segmentation," Medical Image Analysis, 2001, pp. 1-14.
Mueller et al, "High-Quality Splatting on Rectilinear Grids with Efficient Culling of Occluded Voxels," IEEE Transactions on Visualization and Computer Graphics, Apr.-Jun. 1999, pp. 116-134, vol. 5, No. 2.
Neophytou et al, "Post-Convolved Splatting," Joint Eurographics, IEEE TGVG Symposium on Visualization, 2003, Section 3, pp. 223-230, 300.
Preim et al, "Resection Proposals for Oncologic Liver Surgery based on Vascular Territories," CARS/Springer 2002, pp. 1-6.
Rossi et al, "Reconstruction from Projections Based on Detection and Estimation of Objects—Parts I and II: Performance Analysis and Robustness Analysis," Aug. 1984, IEEE Transactions on Acoustics, Speech, and Signal Processing, vol. ASSP-32, No. 4, pp. 886-906.
Salome et al, "A Synchrotron Radiation Microtomography System for the Analysis of Trabecular Bone Samples," Am. Assoc. Phys. Med., Oct. 1999, Med. Phys., vol. 26, No. 10, pp. 2194-2204.
Nestover, "Splatting: A Parallel, Feed-Forward Volume Rendering Algorithm," PhD Thesis, Department of computer Science, University of North Carolina, Chapel Hill, NC, 1991, 103 pages.
Canadian communication dated Nov. 24, 2016 in corresponding Canadian patent application No. 2,672,094.

* cited by examiner

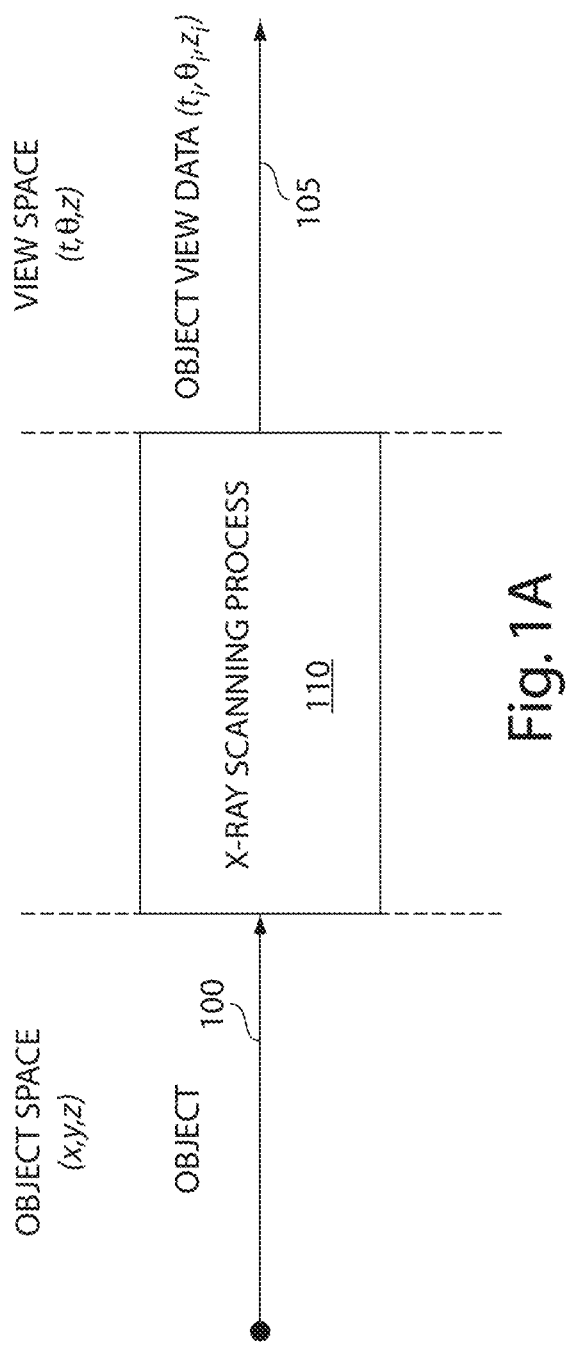

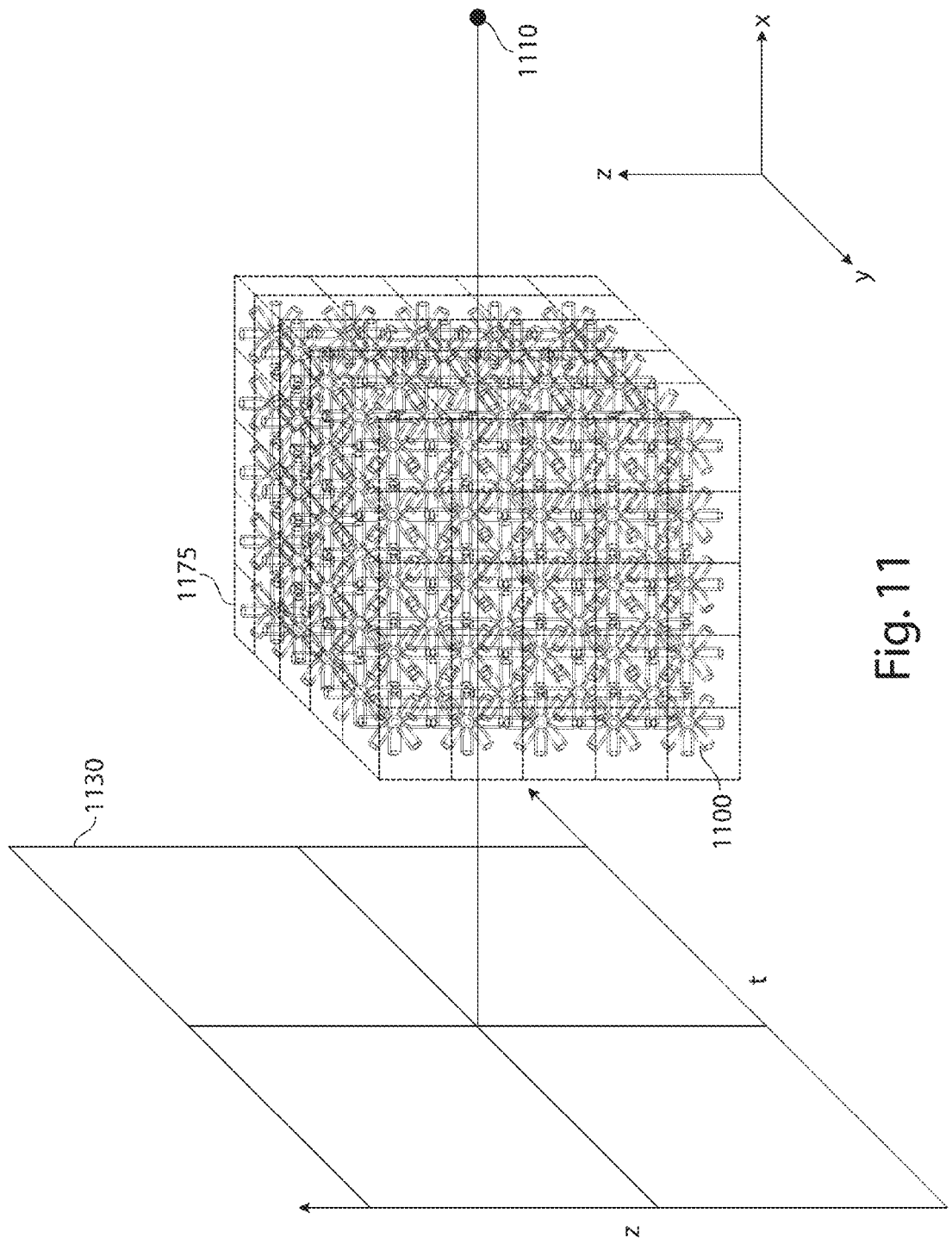

$$I(\mathbf{x}) = I_0 + \nabla I^t(\mathbf{x} - \mathbf{x}_0) + (\mathbf{x} - \mathbf{x}_0)^t H(\mathbf{x} - \mathbf{x}_0)$$
$$+ C_{ijk}(x_i - x_{i0})(x_j - x_{j0})(x_k - x_{k0}) + \ldots$$

Fig. 27A $$H = \begin{bmatrix} \dfrac{\partial^2 I}{\partial x^2} & \dfrac{\partial^2 I}{\partial x \partial y} & \dfrac{\partial^2 I}{\partial x \partial z} \\ \dfrac{\partial^2 I}{\partial x \partial y} & \dfrac{\partial^2 I}{\partial y^2} & \dfrac{\partial^2 I}{\partial y \partial z} \\ \dfrac{\partial^2 I}{\partial x \partial z} & \dfrac{\partial^2 I}{\partial y \partial z} & \dfrac{\partial^2 I}{\partial z^2} \end{bmatrix}$$

Fig. 27B $$f(\mathbf{x};\alpha,\beta,\gamma) = \sum_i k_i(\alpha,\beta,\gamma) f_i(\mathbf{x};\alpha_i,\beta_i,\gamma_i)$$

Fig. 28A $$(\alpha_i, \beta_i, \gamma_i) \begin{bmatrix} 1 & 0 & 0 \\ 0 & 1 & 0 \\ 0 & 0 & 1 \\ \frac{1}{\sqrt{3}} & \frac{1}{\sqrt{3}} & \frac{1}{\sqrt{3}} \\ -\frac{1}{\sqrt{3}} & \frac{1}{\sqrt{3}} & \frac{1}{\sqrt{3}} \\ \frac{1}{\sqrt{3}} & \frac{1}{\sqrt{3}} & -\frac{1}{\sqrt{3}} \end{bmatrix}$$

Fig. 28B $$\begin{bmatrix} \alpha^2 \\ \alpha\beta \\ \alpha\gamma \\ \beta^2 \\ \beta\gamma \\ \gamma^2 \end{bmatrix} = \begin{bmatrix} \alpha_0^2 & \alpha_1^2 & \alpha_1^2 & \alpha_2^2 & \alpha_3^2 & \alpha_4^2 \\ \alpha_0\beta_0 & \alpha_1\beta_1 & \alpha_2\beta_2 & \alpha_3\beta_3 & \alpha_4\beta_4 & \alpha_5\beta_5 \\ \alpha_0\gamma_0 & \alpha_1\gamma_1 & \alpha_2\gamma_2 & \alpha_3\gamma_3 & \alpha_4\gamma_4 & \alpha_5\gamma_5 \\ \beta_0^2 & \beta_1^2 & \beta_2^2 & \beta_3^2 & \beta_4^2 & \beta_5^2 \\ \beta_0\gamma_0 & \beta_1\gamma_1 & \beta_2\gamma_2 & \beta_3\gamma_3 & \beta_4\gamma_4 & \beta_5\gamma_5 \\ \gamma_0^2 & \gamma_1^2 & \gamma_2^2 & \gamma_3^2 & \gamma_4^2 & \gamma_5^2 \end{bmatrix} \begin{bmatrix} k_0 \\ k_1 \\ k_2 \\ k_3 \\ k_4 \\ k_5 \end{bmatrix}$$

Fig. 28C under 35 U.S.C. §120 and is a continuation (CON) of U.S. Ser. No. 13/969,669, entitled "METHODS AND APPARATUS FOR IDENTIFYING SUBJECT MATTER IN VIEW DATA," filed on Aug. 19, 2013, which claims priority under 35 U.S.C. §120 and is a continuation (CON) of U.S. Ser. No. 13/154,787, entitled "METHODS AND APPARATUS FOR IDENTIFYING SUBJECT MATTER IN VIEW DATA," filed on Jun. 7, 2011, which claims priority under 35 U.S.C. §120 and is a continuation (CON) of Ser. No. 11/299,558, entitled "METHODS AND APPARATUS FOR IDENTIFYING SUBJECT MATTER IN VIEW DATA," filed on Dec. 9, 2005, which claims priority under 35 U.S.C. §120 and is a continuation-in-part (CIP) of U.S. Ser. No. 10/871,265, entitled "METHODS AND APPARATUS FOR MODEL-BASED DETECTION OF STRUCTURE IN VIEW DATA," filed on Jun. 17, 2004, which claims priority under 35 U.S.C. §119(e) to U.S. Provisional Application Ser. No. 60/479,114, entitled "MODEL-BASED TOMOGRAPHIC RECONSTRUCTION OF VESSEL NETWORKS," filed on Jun. 17, 2003, all of which are herein incorporated by reference in their entirety.

METHODS AND APPARATUS FOR IDENTIFYING SUBJECT MATTER IN VIEW DATA

RELATED APPLICATIONS

This application claims priority under 35 U.S.C. §120 and is a continuation (CON) of U.S. Ser. No. 13/969,669, entitled "METHODS AND APPARATUS FOR IDENTIFYING SUBJECT MATTER IN VIEW DATA," filed on Aug. 19, 2013, which claims priority under 35 U.S.C. §120 and is a continuation (CON) of U.S. Ser. No. 13/154,787, entitled "METHODS AND APPARATUS FOR IDENTIFYING SUBJECT MATTER IN VIEW DATA," filed on Jun. 7, 2011, which claims priority under 35 U.S.C. §120 and is a continuation (CON) of Ser. No. 11/299,558, entitled "METHODS AND APPARATUS FOR IDENTIFYING SUBJECT MATTER IN VIEW DATA," filed on Dec. 9, 2005, which claims priority under 35 U.S.C. §120 and is a continuation-in-part (CIP) of U.S. Ser. No. 10/871,265, entitled "METHODS AND APPARATUS FOR MODEL-BASED DETECTION OF STRUCTURE IN VIEW DATA," filed on Jun. 17, 2004, which claims priority under 35 U.S.C. §119(e) to U.S. Provisional Application Ser. No. 60/479,114, entitled "MODEL-BASED TOMOGRAPHIC RECONSTRUCTION OF VESSEL NETWORKS," filed on Jun. 17, 2003, all of which are herein incorporated by reference in their entirety.

FIELD OF THE INVENTION

The present invention relates to imaging and more particularly to techniques for identifying subject matter of interest in view data, for example, in view data obtained from an X-ray scanning device.

BACKGROUND OF THE INVENTION

X-ray imaging technology provides a non-invasive technique for visualizing the internal structure of an object of interest by exposing the object to high energy electromagnetic radiation (i.e., X-rays). X-rays emitted from a radiation source interact with the object and are absorbed, scattered and/or diffracted at varying levels by the internal structures of the object. Transmitted X-ray radiation, for example, is attenuated according to the various absorption characteristics of the materials which the X-rays encounter. By measuring the attenuation of the X-ray radiation that exits the object, information related to the density distribution of the object may be obtained.

To obtain X-ray information about an object, an X-ray source and an array of detectors responsive to X-ray radiation may be arranged about the object. Each detector in the array, for example, may generate an electrical signal proportional to the intensity and/or energy of X-ray radiation impinging on a surface of the detector. The source and array may be rotated around the object in a predetermined path to obtain a number of views of the object at different angles. At each view, the detector signal generated by each detector in the array indicates the total absorption (i.e., attenuation) incurred by material substantially in a line between the X-ray source and the detector. Therefore, the array of detection signals records the projection of the object onto the detector array at a number of views of the object, and provides one method of obtaining view data of the object.

View data obtained from an X-ray scanning device may be of any form that provides transmission (attenuation), scatter and/or diffraction information as a function of view angle or orientation with respect to the object being scanned. View data may be obtained by exposing a planar cross-section of an object, referred to as a slice, to X-ray radiation. Each rotation about the object (e.g., a 180° rotation of the radiation source and detector array) provides information about the interaction of X-rays with a two-dimensional (2D) slice of the object.

Accordingly, the X-ray scanning process transforms a generally unknown material distribution of an object into view data having information about how the X-rays interacted with the unknown density. For example, the view data may indicate how the material distribution attenuated the X-rays, providing information related to the density and/or atomic number of the material distribution. FIG. 1A illustrates a diagram of the transformation operation performed by the X-ray scanning process. An object 100 having an unknown density distribution in object space is subjected to X-ray scanning. Object space refers herein to the coordinate frame of an object of interest, for example, an object undergoing an X-ray scan. A Cartesian coordinate frame (i.e., (x, y, z)) may be a convenient coordinate system for object space, however, object space may be described by any other suitable coordinate frame, such as spherical or cylindrical coordinates.

X-ray scanning process 110 generates object view data 105 in a view space coordinate frame (e.g., coordinate frame (t,θ,z)). For example, object view data 105 may include attenuation information from a plurality of detectors in an array (corresponding to the view space t-axis), at a number of orientations of the X-ray scanning device (corresponding to the view space θ-axis), over a number of cross-sections of the object (corresponding to the view space z-axis) to form three dimensional (3D) view data. The 3D view data may be considered as a series of 2D slices stacked on top of one another to form the third axis (e.g., the z-axis). Accordingly, X-ray scanning process 110 transforms a continuous density distribution in object space to discrete view data in view space.

To reconstruct the density distribution of the object from the view data, the view data may be projected back into object space. The process of transforming view data in view space into reconstructed data represented in object space is referred to as reconstruction. FIG. 1B illustrates a reconstruction process 120 that transforms view data 105 into reconstructed data 100' (e.g., a reconstructed density image of a portion of object 100). To form reconstructed data 100', a density value for each desired discrete location of object 100 in object space is determined based on the information available in view data 105. It should be appreciated that 2D and 3D images in an object space coordinate frame (e.g., images that generally mimic the appearance of subject matter as it is perceived by the human visual system) are reconstructed data. Many techniques have been developed for reconstruction to transform acquired view data into reconstructed data. For example, various iterative methods, Fourier analysis, back-projection, and filtered back-projection are a few of the techniques used to form reconstructed data from view data obtained from an X-ray scanning device.

It should be appreciated that the view data may be of any dimensionality. For example, the view data may be two dimensional (2D) representing a cross-section or slice of an object being scanned. The 2D view data may be reconstructed to form reconstructed data in two dimensional object space. This process may be repeated with view data obtained over successive slices of an object of interest. The reconstructed data may be stacked together to form reconstructed data in 3D (e.g., 3D voxel data $I(x_i,y_i,z_i)$). In medical imaging, computed tomography (CT) images may be acquired in this manner.

Reconstructed data contains less information than the view data from which the reconstructed data was computed. The loss in information is due, at least in part, to the discrete nature of X-ray scanning (i.e., a finite number of detectors and a finite number of views) and to assumptions made during back-projection. In this respect, reconstructed data represents intensity as a discrete function of space. The term "intensity" refers generally to a magnitude, degree and/or value at some location in the data, whether it be view data or reconstructed data. To back-project view data, the scan plane (i.e., the 2D cross-section of the object being scanned) may be logically partitioned into a discrete grid of pixel regions.

The reconstruction process, when determining intensity values for each of the pixel regions, typically operates on the assumption that all structure within a pixel region has a same and single density and therefore computes an average of the density values within the corresponding region of space. This averaging blurs the reconstructed data and affects the resulting resolution. When multiple structures are sampled within a single pixel (e.g., when structure within the object is smaller than the dimension of the corresponding pixel region and/or the boundary of a structure extends partially into an adjacent pixel region), information about the structure is lost. The result is that the reconstructed data has less resolution than the view data from which it was generated. This loss of resolution may obscure and/or eliminate detail in the reconstructed data.

In conventional medical imaging, a human operator, such as a physician or diagnostician, may visually inspect reconstructed data to make an assessment, such as detection of a tumor or other pathology or to otherwise characterize the internal structures of a patient. However, this process may be difficult and time consuming. For example, it may be difficult to assess 3D biological structure by attempting to follow structure through stacked 2D reconstructed data. In particular, it may be perceptually difficult and time consuming to understand how 2D structure is related to 3D structure as it appears, changes in size and shape, and/or disappears in successive 2D slices of reconstructed data. A physician may have to mentally arrange hundreds or more 2D slices into a 3D picture of the anatomy. To further frustrate this process, when anatomical structure of interest is small, the structure may be difficult to discern or absent altogether in the reconstructed data.

Image processing techniques have been developed to automate or partially automate the task of understanding and partitioning the structure in reconstructed data. Such techniques are employed in computer aided diagnosis (CAD) to assist a physician in identifying and locating structure of interest in 2D or 3D reconstructed data. CAD techniques often involve segmenting reconstructed data into groups of related pixels (in 2D) or voxels (in 3D) and identifying the various groups of voxels, for example, as those comprising a tumor or a vessel or some other structure of interest. However, segmentation on reconstructed data has proven difficult, especially with respect to relatively small or less salient structure in the reconstructed data.

Many segmentation techniques rely, in part, on one or more filtering operations. Filtering processes involve comparing reconstructed data with a numerical operator (i.e., the filter) to examine properties of the reconstructed data. For example, filters may be applied to reconstructed data to examine higher order properties of the data, such as first derivative and second derivative information. The higher order information often reveals characteristics of the reconstructed data that suggest how the data should be segmented, such as edge features that may demarcate boundaries between structures or ridge features that identify properties of a particular structure of interest. Filters may be designed to respond, emphasize or otherwise identify any number of properties, characteristics and/or features in the reconstructed data.

Filtering may be achieved by applying a function to the reconstructed data. In particular, a filter may comprise a function or discrete collection of numbers over the domain of the filter, referred to as the filter kernel. The filter may be superimposed on the reconstructed data and the underlying data convolved with the filter kernel to generate a value at the location (e.g., the center of the kernel) at which the kernel was applied. The filter may then be applied to the reconstructed data at a new location, and convolved with the reconstructed data to generate another value. This process may be repeated over all the reconstructed data or desired portion of the reconstructed data to generate new data having the filter output at each location as the intensity. Alternatively, the filter outputs may be used to modify, label or otherwise augment the reconstructed data being operated on.

A filter may be n-dimensional. That is, the domain of the filter may be a continuous or discrete function over any number of dimensions. For example, 2D filters and 3D filters may be applied to 2D and 3D reconstructed data to detect and/or identify properties of the data that facilitate locating structure of interest or otherwise facilitating the segmentation of the reconstructed data. A vast array of filters are known in the art such as Gaussian filters, derivative Gaussian filters, Hessian filters, edge detectors such as difference filters like the Sobel and Canny operators, and numerous other filters specially designed to perform a specific image processing task.

Reconstructed data from view data obtained from conventional X-ray scanning devices may be limited in resolution due, in part, to the lossy reconstruction process. For example, reconstructed data from some conventional X-ray scanning devices may be limited to a resolution of approximately 500 microns. As a result, conventional imaging techniques may be unable to capture structure having dimensions smaller than 500 microns. That is, variation in the density distribution of these small structures cannot be resolved by conventional reconstruction. Micro-computer tomography (microCT) can produce view data of small objects at resolutions that are an order of magnitude greater than conventional X-ray scanning devices. However, microCT cannot image large objects such as a human patient and therefore is unavailable for in situ and generally non-invasive scanning of the human anatomy.

The ability of filtering techniques to discriminate patterns, characteristics and/or properties in reconstructed data is limited to the resolution of the reconstructed data. Blurring and loss of information due to the reconstruction process frustrates a filter's ability to identify, distinguish and/or locate characteristics or properties in reconstructed data at high resolutions. Accordingly, conventional filtering techniques on reconstructed data have been ineffective at identifying and/or detecting the presence of relatively small structure that may be of interest.

SUMMARY OF THE INVENTION

One embodiment according to the present invention includes a method of filtering view data to detect subject matter of interest in view data obtained by scanning an object, the view data including scan information about the object at least along a view axis indicative of a view angle about the object at which the scan information was obtained, the method comprising acts of providing a filter adapted to respond to the subject matter of interest in the view data, the filter including a filter kernel, varying the filter kernel according to which location in the view data to which the filter is to be applied, and applying the filter to a plurality of locations to facilitate identifying the subject matter of interest in the view data.

Another embodiment according to the embodiment according to the present invention includes a method of detecting subject matter of interest in view data obtained by scanning an object, the subject matter of interest arising from structure of interest in the object, the method comprising acts of providing a filter, splatting the filter to provide a filter splat responsive to the subject matter of interest, and performing at least one operation on at least a portion of the view data using the filter splat to facilitate determining whether the subject matter of interest is present in the portion of the view data.

Another embodiment according to the present invention includes a computer readable medium encoded with a program for execution on at least one processor, the program, when executed on the at least one processor, performing a method of detecting subject matter of interest in view data obtained by scanning an object, the subject matter of interest arising from structure of interest in the object, the method comprising acts of providing a filter associated with the structure of interest, splatting the filter to provide a filter splat responsive to the subject matter of interest, and performing at least one operation on at least a portion of the view data using the filter splat to facilitate determining whether the subject matter of interest is present in the portion of the view data.

Another embodiment according to the present invention includes an apparatus adapted to detect subject matter of interest in view data obtained by scanning an object, the apparatus comprising at least one input adapted to receive the view data, and at least one controller, coupled to the at least one input, the at least one controller adapted to generate a filter adapted to respond to the subject matter of interest, splat the filter onto a portion of the view data to provide a filter splat, and perform at least one operation on the portion of the view data using the filter splat to facilitate determining whether the subject matter of interest is present in the portion of the view data.

BRIEF DESCRIPTION OF THE DRAWINGS

FIGS. 1A, 1B and 1C illustrate transformations of an X-ray scanning process, a reconstruction process, and the radon transform, respectively;

FIG. 11 illustrates the filter cluster of FIG. 10B sampled according to FIG. 10C positioned throughout logically tesselated object space to be splatted onto view data, in accordance with one embodiment of the present invention;

FIGS. 27A-27F illustrate the use of the Hessian as a filter, in accordance with one embodiment of the present invention;

FIGS. 28A-28C illustrate the use of steerable filters, in accordance with one embodiment of the present invention;

DETAILED DESCRIPTION

As discussed above, segmentation of reconstructed data, and particularly, segmentation of relatively small structure, is limited by noise, blurring and loss of resolution resulting from the reconstruction process. Structure at or below the resolution of the reconstructed data, though present in the view data, may be unavailable to detection and/or segmentation algorithms that operate on reconstructed data, such as the application of filters adapted to respond to structure of interest in the reconstructed data. For example, the reconstruction processes may blur or eliminate structure to the extent that a filter will not be responsive enough to provide filter outputs that can distinguish the structure of interest.

Model-based techniques have been employed to avoid some of the problems associated with reconstruction and post-reconstruction image processing algorithms, such as filtering. Model-based techniques may include generating a model to describe structure assumed to be present in the view data of an object of interest. For example, a priori knowledge of the internal structure of an object of interest may be used to generate the model. The model may then be compared to the view data to test the validity of the model and to modify its configuration based on the view data. However, conventional model-based techniques may suffer from the computational complexity of determining how to most appropriately configure the model. In addition, optimization techniques used to modify the configuration of the model may be vulnerable to converging to local minimum solutions that are not representative of the actual structure in the view data.

The term "model" refers herein to any geometric, parametric or other mathematical description and/or definition of properties and/or characteristics of a structure, physical object, or system. For example, in an X-ray environment, a model of structure may include a mathematical description of the structure's shape and density distribution. A model may include one or more parameters that are allowed to vary over a range of values, such that the model may be deformed to take on a variety of configurations. The term "configuration" with respect to a model refers herein to an instance wherein model parameters have been assigned a particular value.

Figure 1B:
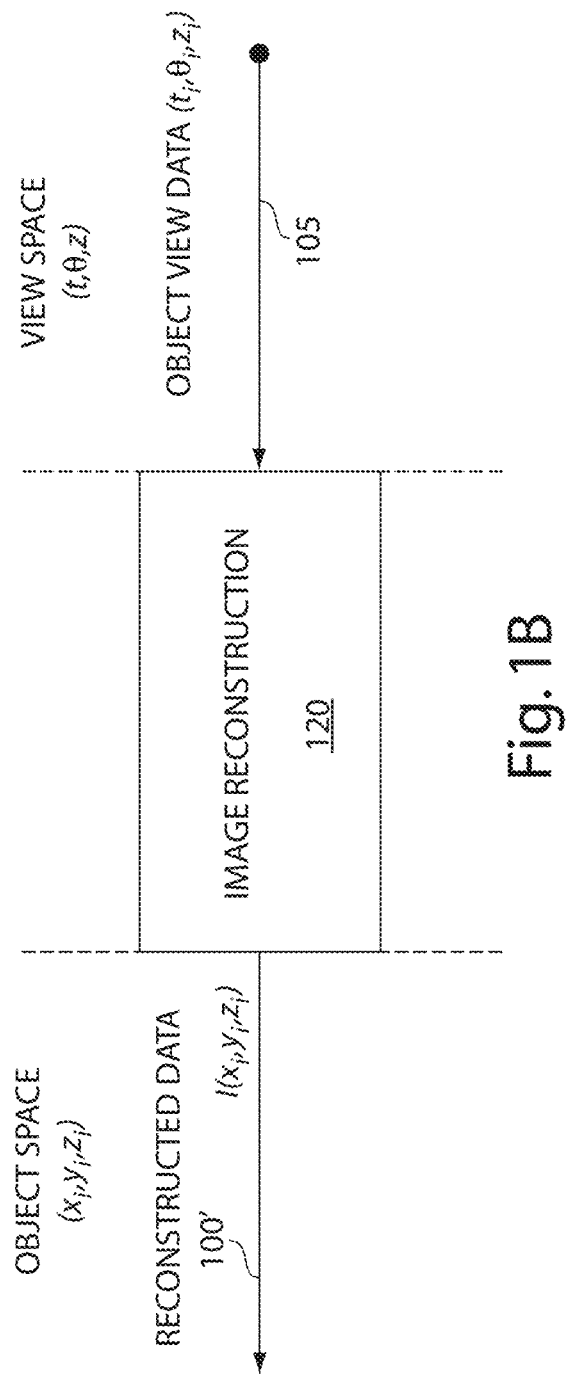
Figure 1C:
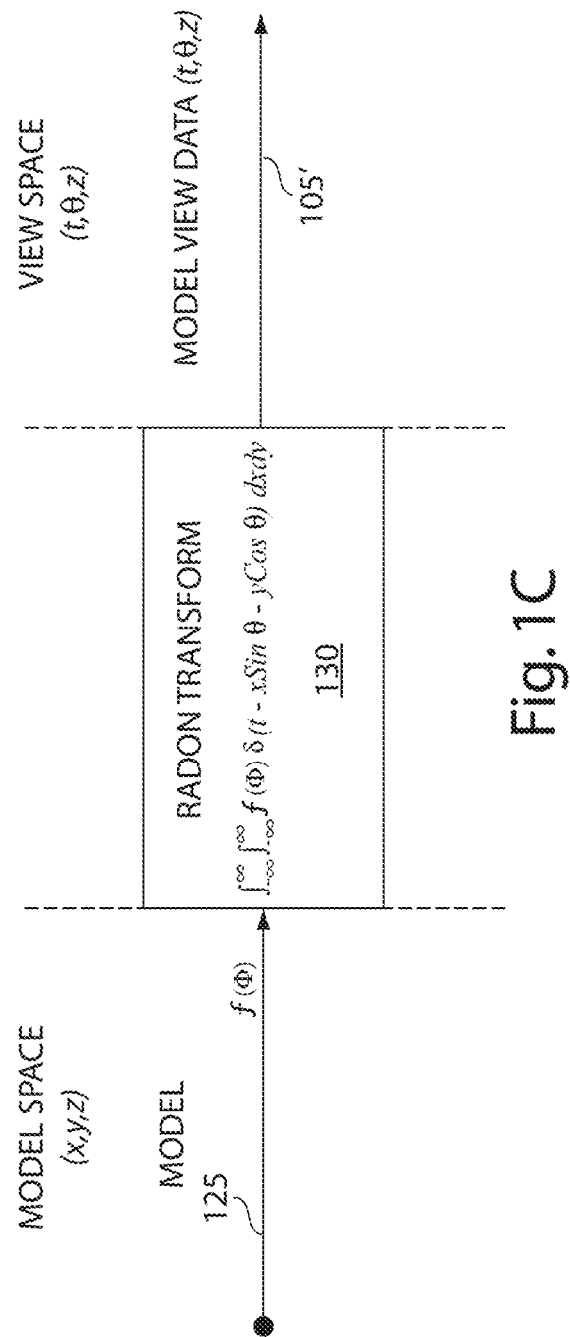

Once a configuration of a model is determined, view data of the model (referred to as model view data) may be computed, for example, by taking the radon transform of the model. The radon transform, operating on a function, projects the function into view space. FIG. 1C illustrates the operation of the radon transform 130 on a model 125 of object 100. Model 125 is described by the function $f(\Phi)$ in model space, where $\Phi$ is a vector of the parameters characterizing the model. Since model 125 is generated to describe object 100, it may be convenient to use the same coordinate frame for model space and object space, although they may be different so long as the transformation between the two coordinate frames are known. The radon transform 130 transforms model 125 from model space to model view data 105' (i.e., to a function in the view space coordinate frame).

It should be appreciated that X-ray scanning process 110 and radon transform 130 perform substantially the same operation, i.e., both perform a transformation from object space (or model space) to view space. The scanning process performs a discrete transformation from object space to view space (i.e., to a discrete function in $(\theta_i, t_i)$) and the radon transform performs a continuous transformation from object space to view space (i.e., to a continuous function in $(\theta, t)$). Model view data obtained by projecting a configuration of the model (i.e., an instance of $f$ where each parameter in $\Phi$ has been assigned a value) into view space via the radon transform, may then be compared to the object view data acquired from the X-ray scanning device to measure how accurately the model describes the structure of interest in the object being scanned. The model may then be deformed or otherwise updated until its radon transform (the model view data) satisfactorily fits the object view data, i.e., until the configuration of the model has been optimized.

However, conventional model based techniques that seek to avoid reconstruction have been frustrated by the combinatorial complexity of fitting a model configuration to the observed view data. In particular, when the structure being modeled is complex and comprises a number of deformable parameters, the combinatorial problem of configuring the model may become intractable. That is, as the number of parameters over which the model is allowed to vary increases, the number of possible configurations of the model tends to explode. In addition, Applicant has appreciated that with no guidance on how to initially configure the model, a poorly chosen initial hypothesis may cause a subsequent optimization scheme to converge to an undesirable local minimum. As a result, the selected model configuration may poorly reflect the actual structure that was scanned.

Applicant has developed techniques that benefit from both the flexibility of filtering and the high resolution of view data. In one embodiment according to the present invention, filtering techniques are applied to view data obtained from scanning an object to identify and/or locate properties characteristic of structure of interest within the object, rather than applying filtering techniques to reconstructed data formed from the view data. Filtering in the domain of the view data provides the flexibility of conventional filtering of reconstructed data, while permitting the filter to operate at the higher resolution of the view data. Filter processing on the view data thus facilitates detection of relatively small structure missed by and/or invisible to conventional filtering of reconstructed data.

Various aspects of the present invention derive from Applicant's appreciation that filtering view data to facilitate detection and/or segmentation of subject matter associated with structure of interest may be complicated due to the changing appearance of the subject matter in different portions of the view data, for example, across multiple views. That is, the structure of interest scanned at various view angles will project and therefore appear differently in the view data depending on the view angle. Accordingly, a filter adapted to respond to subject matter associated with structure of interest in one view may not be well suited to respond to the subject matter in another view. For example, the scale of the filter may become increasingly mismatched with the scale of the subject matter in the view data as the view angle changes.

Applicant has appreciated that filtering in view data may be made more effective by varying one or more characteristics of a filter as a function of one or more variables to more accurately match properties of the subject matter the filter is designed to detect. For example, by varying one or more characteristics of a filter across multiple views, the filter may be more responsive to the appearance of the subject matter as it varies across the multiple views of the view data.

In one embodiment, a filter kernel of a filter is varied depending on the location in the view data that the filter is applied. For example, in view data having an axis corresponding to view angle, the filter kernel may be varied depending on the location along the view axis at which the filter is applied. In one embodiment, the size of the filter kernel is varied depending on the location in the view data at which it is applied. In another embodiment, the values in the kernel are varied depending on the location in the view data at which the filter is applied. In one embodiment, a filter kernel is varied by splatting a filter represented in object space onto the view, as described in further detail below. It should be appreciated that the filter kernel may be varied in any manner such that the filter is generally more responsive to the subject matter of interest as it changes throughout the view data, as the aspects of the invention are not limited in this respect.

Applicant has appreciated that by providing a filter described and/or defined in object space (e.g., in the same coordinate frame as the structure of interest) and projecting the filter onto the view data (a process referred to herein as splatting, which is described in further detail below) may improve upon certain deficiencies in filtering view data caused by the variation of the appearance of the subject matter across one or more dimensions of the view data. That is, by performing an operation that, for example, causes a filter to undergo a same or similar transformation as the structure of interest, the transformed filter may be more responsive to the subject matter of interest as it varies throughout the view data.

In one embodiment according to the present invention, a 3D filter associated with structure of interest is generated and positioned at a desired location and orientation in object space. The 3D filter is then splatted (e.g., projected) onto two dimensions of view data obtained from scanning an object assumed to contain at least some structure of interest whose projection is assumed to produce the subject matter of interest. The resulting filter splat, responsive to the subject matter of interest, may then be used to operate on the underlying view data to generate a filter output indicative of the likelihood that the filter splat is operating on the subject matter of interest. For example, the filter splat may be convolved with the underlying view data to generate a likelihood value related to the strength of an assertion that structure is present at a position and orientation characterized by the configuration of the filter.

In another embodiment according to the present invention, the 3D filter is splatted onto a plurality of 2D views that form the view data obtained from scanning an object, each view representing 2D view data obtained at a different view angle with respect to an X-ray source. The resulting filter splats are then convolved with the underlying view data within the respective view onto which the 3D filter was splatted to generate filter data through each view (e.g., for an orbit) of the 3D view data. The filter data may be analyzed to determine the likelihood that the view data arose from structure of interest located and oriented (e.g., configured) approximately as characterized by the 3D filter configuration.

In another embodiment according to the present invention, structure below 500 microns is detected, at least in part, by performing filtering operations in view data obtained from a conventional large object X-ray scanning device, more preferably below 250 microns, more preferably below 100 microns, and even more preferably below 50 microns.

In another embodiment according to the present invention, structure at or below 50 microns is detected, at least in part, by performing filtering operations in view data obtained from a microCT scanning device, more preferably below 25 microns, more preferably below 10 microns, and even more preferably below 5 microns.

One application for the view space filtering techniques described herein relates to use with the pulmonary vessel network of humans, which is a relatively complex structure, wherein blood vessels with relatively large radii may branch off into blood vessels with smaller radii and so on. The ability to detect and segment this structure may provide a foundation for detection and/or characterization of many forms of disease of the lungs and heart such as the family of conditions known as chronic obstructive pulmonary disease (COPD), which includes: emphysema; lung cancer; pulmonary emboli; idiopathic pulmonary fibrosis; and pulmonary arterial hypertension.

In one embodiment according to the present invention, a filter adapted to respond to portions of a vessel network in 3D view data is provided at one or more configurations (e.g., locations, orientations and/or scales) to generate multiple hypotheses about the existence of vessel structure in the view data. The variously configured filters are then splatted onto two dimensions and compared with the underlying view data across multiple views of the 3D view data. The filter data produced from the filter splat comparisons with the view data may be used to analyze the probability that the view data resulted from vessel structure existing in the object at approximately the configuration of the corresponding filters.

Following below are more detailed descriptions of various concepts related to, and embodiments of, methods and apparatus according to the present invention. It should be appreciated that various aspects of the inventions described herein may be implemented in any of numerous ways. Examples of specific implementations are provided herein for illustrative purposes only. For example, while many of the embodiments are described in connection with view data obtained using X-ray technology, the aspects of the invention described herein are not limited to use with X-ray technology and may be used with view data from other sources, including but not limited to positron emission tomography (PET) scanners, single positron emission computed tomography (SPECT) scanners, and magnetic resonance imaging (MRI) devices.

Figure 2:
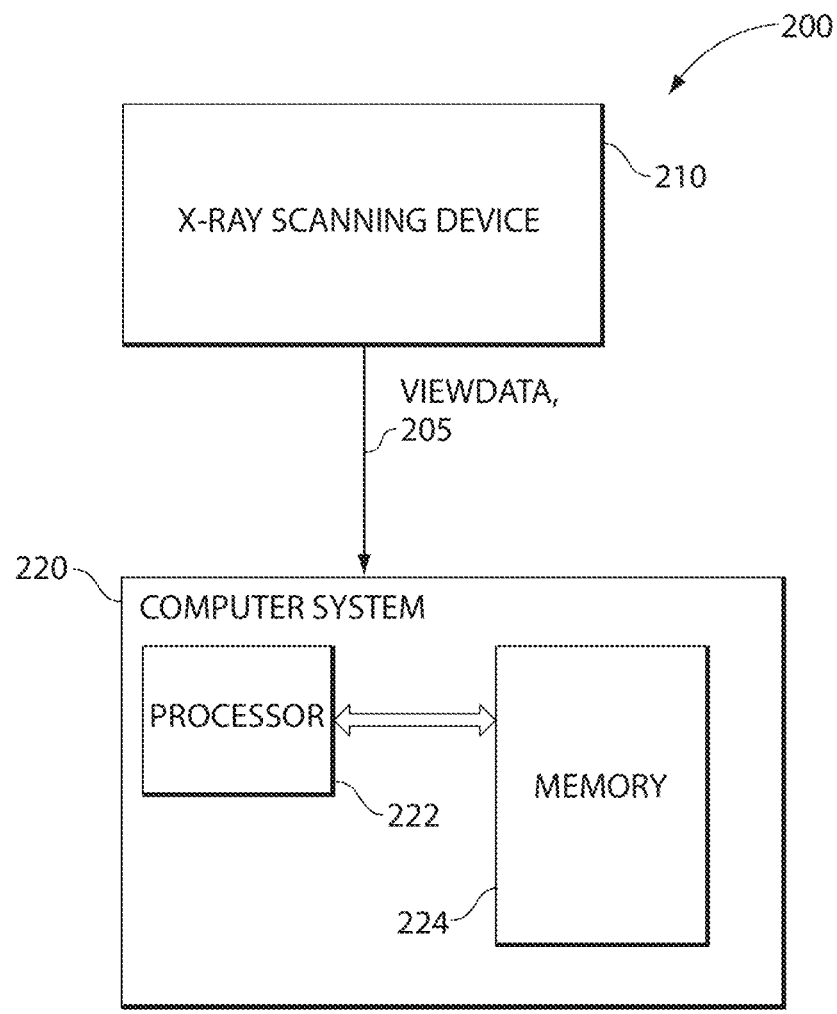
FIG. 2 illustrates one example of a system including an X-ray scanning device and a computer system suitable for practicing various aspects of the invention.

FIG. 2 illustrates a block diagram of one embodiment of a system 200 suitable for practicing various aspects of the present invention. System 200 includes an X-ray scanning device 210 and computer system 220. X-ray scanning device 210 may be any device capable of acquiring view data of an object of interest. X-ray scanning devices may be designed with varying capabilities, such as resolution, scan speed and scan path (e.g., circular, helical, etc.), may employ a variety of radiation emission technologies, such as cone beam, fan beam and pencil beam technologies, and may be arranged in numerous configurations, such as circular or rectangular geometry detector arrays, and may provide data of different types such as CT or laminographic data. Any X-ray scanning device providing view data may be suitable, as aspects of the invention are not limited to view data obtained from any particular type, arrangement and/or capability. As discussed above, view data may be obtained from other types of scanning devices, as aspects of the invention are not limited for use with view data obtained from X-ray scanning devices.

Computer system 220 may include a processor 222 connected to one or more storage devices including storage medium 224. Storage medium 224 may be any of various computer-readable media capable of storing electronic information and may be implemented in any number of ways. Storage medium 224 may be encoded with instructions, for example, as part of one or more programs that, as a result of being executed by processor 220, instruct the computer to perform one or more of the methods or functions described herein, and/or various embodiments, variations and combinations thereof.

Computer system 220 may be, for example, a personal computer (PC), work station, general purpose computer, or any other computing device. Computer system 220 may be integrated into X-ray scanning device 210 or may be a separate stand alone system, either proximate to or remote from X-ray scanning device 210. For example, computer system 220 may be connected to X-ray scanning device 210 over a network, connected to multiple scanning devices or may not be connected to any X-ray scanning device at all. In this last respect, computer system 220 may operate on view data previously stored in storage medium 224, or may obtain the view data from some other location, e.g., another computer system, over a network, via transportable storage medium, etc. It should be appreciated that any computing environment may be used, as the aspects of the invention described herein are not limited to use with a computer system of any particular type or implementation.

Figure 3A:
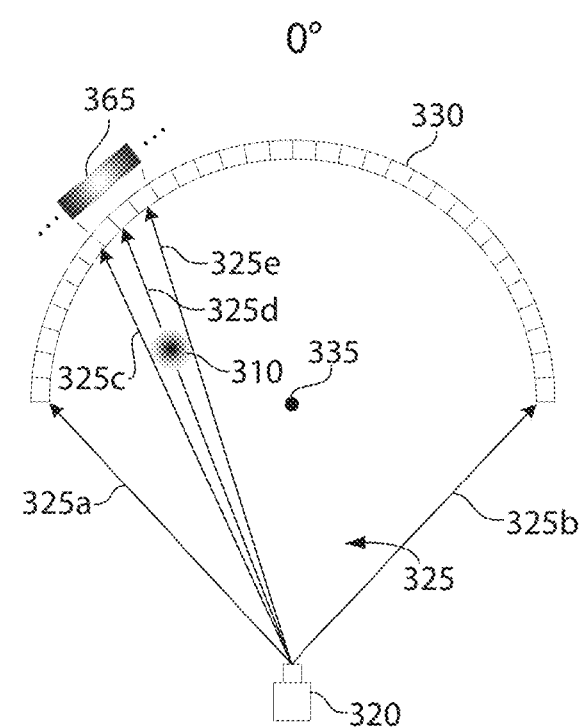
FIGS. 3A-3C illustrate an exemplary X-ray scanning process of an elliptical object having a Gaussian density distribution.
Figure 3B:
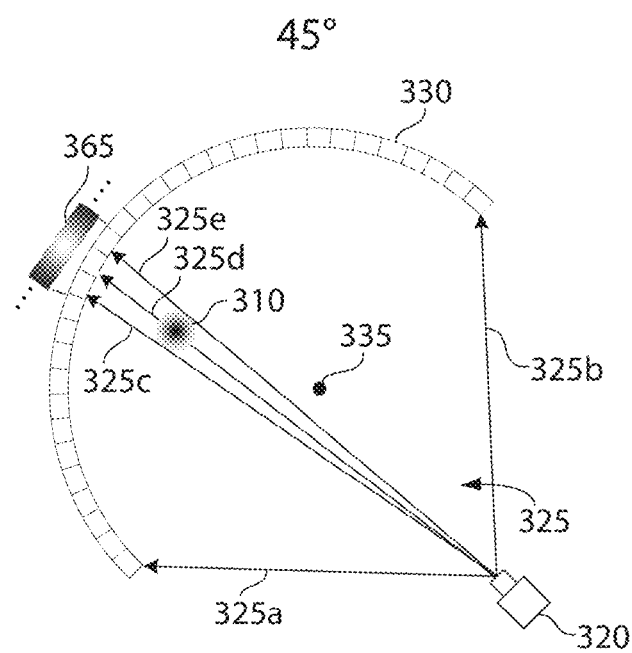
Figure 3C:
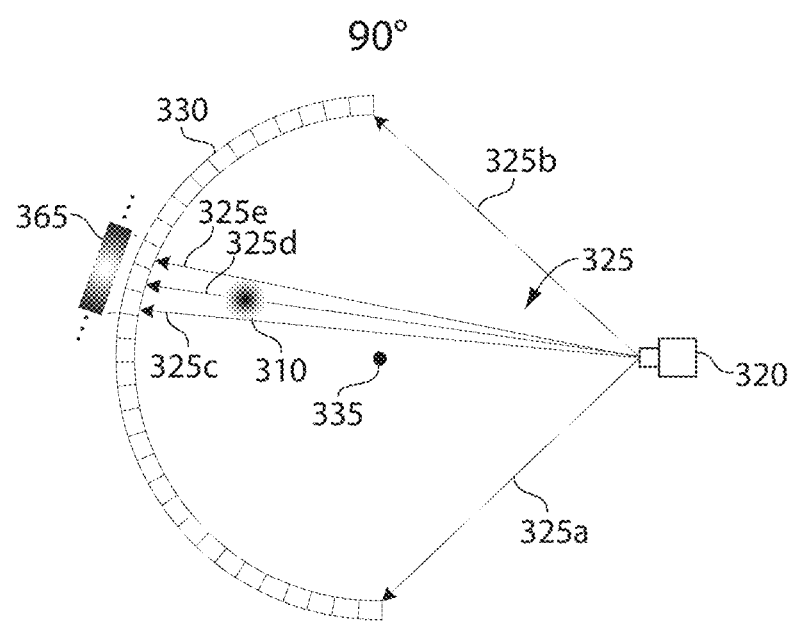

FIGS. 3A-3C illustrates a scanning process of an ellipse that may represent, for example, a cross-section of a vessel structure having a radial density similar to a Gaussian function. X-ray scanning device 300 may be used, for example, as the X-ray scanning device 210 in system 200 illustrated in FIG. 2, to obtain successive cross-sections of an object to form 3D view data. One cross-section of the view data obtained from the scan is represented by sinogram 400 illustrated schematically in FIG. 4. FIGS. 3A-3C illustrate a snapshot of portions of an X-ray scanning device 300 at a 0° orientation, including a radiation source 320 adapted to emit X-ray radiation and an array of detectors 330 responsive to the X-ray radiation. Radiation source 320 may emit a substantially continuous fan beam 325, e.g., over an arc between rays 325a and 325b defining the extent of the fan beam. The radiation source 320 may be positioned along the circular extensions of the semi-circular detector array and adapted to rotate together with detector array 330 about a center point 335.

As the radiation source 320 and the detector array 330 rotate about center point 335, the detectors in the array respond to impinging X-rays by generating a detection signal, for example, an electrical signal proportional to the intensity of the radiation impinging on respective detectors. As a result, the detector array records the radiation intensity profile at various orientations of the source and array with respect to ellipse 310. The detection signals generated by each detector in the array may be sampled to obtain values indicating the intensity of an X-ray extending substantially in a line between each detector and the radiation source. The detector array may be sampled, for example, at a degree angle interval, half-degree angle interval, quarter-degree angle interval, etc., as the device rotates to obtain a number of projections of the ellipse 310 at different views. FIGS. 3B and 3C illustrate snap-shots of the X-ray scanning device at 45° and 90°, respectively. A 2D scan of ellipse 310 may include obtaining projections of ellipse 310 over a 180° arc at a desired angle interval AO.

The majority of the radiation emitted by source 320 will impinge unimpeded on the detector array 330. However, some portion of the rays will pass through ellipse 310 before reaching the detector array. The impeded rays will be attenuated to an extent related to the density of ellipse 310. Exemplary rays 325c and 325e substantially tangent to the object will be the least attenuated rays of those that pass through the ellipse. Rays passing substantially through the center of ellipse 310 (e.g., ray 325d) have the most material to penetrate at the highest density and therefore will exhibit the greatest attenuation.

The detectors in the "shadow" of ellipse 310, therefore, will detect radiation having a profile that transitions from substantially zero attenuation at the tangent of ellipse 310, to peak attenuation at the center of ellipse 310, and back to zero attenuation at the other tangent of ellipse 310, as shown by profile 365. For example, profile 365 may be a grayscale representation of the detection signals provided by the detectors in the array that are in the shadow of the ellipse, wherein lighter gray levels indicate greater X-ray attenuation. Accordingly, detectors that are not in the shadow of ellipse 310 produce detection signals having substantially black grayscale values. Profile 365 is illustrated at a higher resolution than the detector array, i.e., profile 365 includes more than a single grayscale value for each detector in the shadow of ellipse 310 to illustrate the characteristic shape of the profile. However, it should be appreciated that each detector illustrated in detector array 330 may be considered as any number of individual detectors generating detection signals such that a profile may be provided at the resolution of the illustrated profile 365.

As the X-ray device rotates, the density distribution of the ellipse will project onto a changing combination of detectors. A 360° rotation of the device causes ellipse 310 to orbit center point 335 (from the perspective of radiation source 320) causing the location of the ellipse projection on the detectors to repeat. Ellipse 310 casts a periodic shadow that falls on the detectors at locations that trace across the detector array as a sinusoid as the orientation of the device increases, which can be mapped to 2D view space as discussed below.

Figure 4:
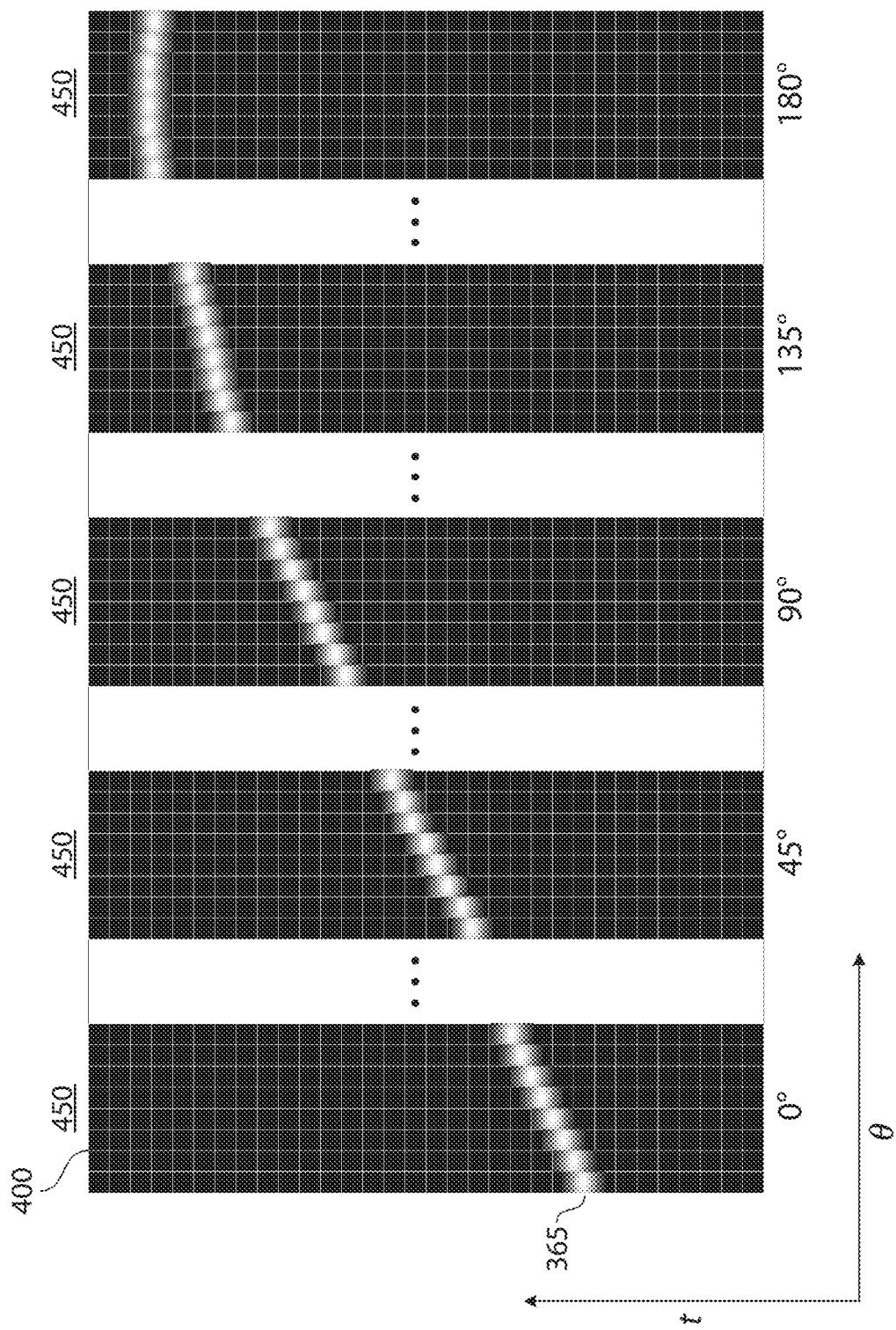
FIG. 4 illustrates a schematic of a sinogram of the view data obtained from the X-ray scanning process illustrated in FIGS. 3A-3C.

FIG. 4 illustrates a sinogram 400 of the view data obtained from scanning ellipse 310 over a 180° degree rotation at an angle interval of one degree. A sinogram is a representation of view data in view space. In particular, a sinogram maps intensity values (e.g., attenuation values, density values, etc.) to a discrete coordinate location in view space. Sinogram 400 has axes of θ and t, where θ represents the orientation of the X-ray device with respect to ellipse 310 and t refers to a location along the detector array. Accordingly, sinogram 400 provides a grayscale representation of the detection signals generated by detector array 330 as the X-ray scanning device rotates.

Specifically, sinogram 400 includes a grid of pixels 450, wherein each pixel has an intensity related to a sample of a detection signal from a respective detector in array 330 at a particular orientation of the X-ray device. For example, the first column of pixels (θ=0), indicates samples from respective detectors responding to impinging radiation at a 0° orientation of the X-ray device. As a result, the characteristic profile 365 from the detectors in the shadow of ellipse 310, centered approximately at the ninth detector in the snapshot illustrated in FIGS. 3A-3C, appears centered approximately at pixel (0,9) in the sinogram. The second column of pixels indicates samples from respective detectors responding to impinging radiation at a 1° orientation of the X-ray device and so on at degree angle intervals.

As θ increases, the location of the profile 365 traces out a portion of a sinusoid that reaches its half-period substantially at a 180° orientation. Portions of the sinogram 400 are illustrated in the vicinity of a 45° orientation, a 90° orientation, a 135° orientation and a 180° orientation to illustrate the sinusoidal transition of the location of profile 365 during the scan. Sinogram 400 illustrates a 2D slice of view data at a particular scan plane (or cross-section) intersecting the object being scanned. Subsequent to acquiring a slice of view data (i.e., 2D view data in the t,θ plane), the object being scanned and the scan plane may be moved relative to one another so that the scan plane intersects the object at a successive cross-section. The scanning process may be repeated to obtain multiple slices. As discussed above, the multiple slices obtained from scanning an object form 3D view data of the object.

Figure 5A:
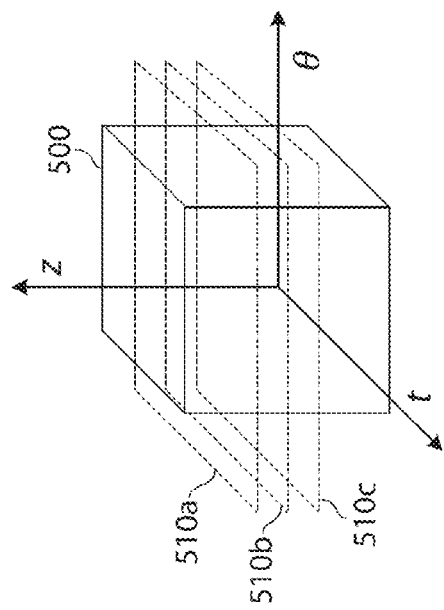
FIGS. 5A-5C illustrates examples of logically partitioning three dimensional (3D) view data into multiple two dimensional (2D) planes.
Figure 5B:
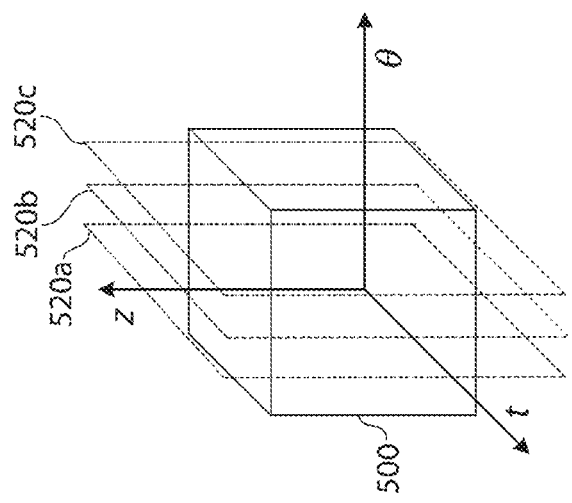
Figure 5C:
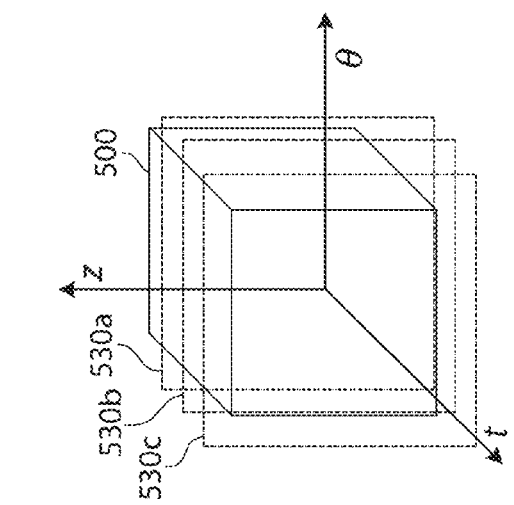

As illustrated schematically in FIGS. 5A-5C, view data may be represented as a discrete 3D function of t, θ and z, where the t-axis describes detector location, the θ-axis describes view angle, and the z-axis describes the location of the scan plane relative to cross-sections of the object from which the view data was obtained. View data 500 is represented schematically as a cube in 3D view space (e.g., in coordinate frame t, θ, z). The 3D view data 500 may be viewed as 2D planes by cutting the view data with planes parallel to the plane formed by any two of the axes, (e.g., planes 510, 520, 530 illustrated in FIGS. 5A-5C). That is, the view data may be viewed in the (t,θ) plane, the (t,z) plane, or the (θ, z) plane.

View data in the (t,θ) plane at a given value z, is referred to herein as a slice and represents 2D view data of a particular cross-section of the object. FIG. 5A illustrates planes 510a-510c intersecting view data 500 at different slices. View data in the (t,z) plane at a given value of $\theta_i$ is referred to herein as a view and represents 2D view data from a particular viewing angle of the X-ray source. FIG. 5B illustrates planes 520a-520c intersecting view data 500 at different views. FIG. 5C shows planes 530a-530c intersecting view data 500 to illustrate 2D view data with respect to a particular detector $t_i$.

Applicant has appreciated that structure of interest, when scanned, may result in characteristic features or properties in the resulting view data that can be detected to identify and/or locate subject matter of interest in the view data. For example, the elliptical structure in FIGS. 3A-3C having a generally Gaussian cross-section results in a generally detectable ridge structure that can be detected and used to configure a model of the structure of interest. Various methods of detecting features in view data to establish one or more parameters of a model configuration were described in application Ser. No. 10/871,265, of which this application is a continuation-in-part (CIP).

As discussed above, the appearance of structure of interest in the view data may change, sometimes substantially, through different portions of the view data. In particular, the appearance of the structure of interest may change from view to view, from cross-section to cross-section, etc. For example, as an X-ray source rotates about an object, structure within the object may be relatively close to the X-ray source at certain view angles and relatively far from the X-ray source at other view angles. Accordingly, the appearance of the structure in the view data (i.e., the subject matter arising from the scanned structure) at the different view angles may be vary across the multiple views. Accordingly, a filter having a kernel adapted to respond to the subject matter arising from the structure in one view, may not be well suited to respond to the subject matter arising from the structure in another view.

Applicant herein describes a generalized filtering scheme that facilitates, ultimately, identifying subject matter in view data at generally increased resolutions by filtering the view data. Embodiments of the generalized filter model include splatting a desired filter represented in object space onto the view data in view space, as described in further detail below. A filter that is responsive to, or that is adapted to respond to subject matter of interest describes a filter that, when applied to data having subject matter of interest, provides an output that has at least one property that is generally distinguishable from outputs resulting when the filter is applied to data essentially without the subject matter of interest. For example, the filter may respond with a stronger (e.g., larger magnitude value) output when applied to subject matter of interest than when applied to other content and/or noise.

A. Generalized Filter Model

Various aspects of the present invention derive from Applicant's appreciation that the appearance of structure of interest in view data may change as a function of one or more variables associated with the view data (e.g., as a function of view angle, cross-section, etc.). Applicant has developed filtering techniques that include varying the kernel of a filter as a function of the one or more variables associated with the view data to better respond to the appearance of the structure of interest as it varies in the view data.

Applicant has further appreciated that filtering techniques conventionally used on reconstructed data can be exploited on view data by projecting a filter designed to respond to subject matter of interest as it would appear in reconstructed data into view space (referred to as splatting) such that it operates directly on the view data. In one embodiment, the process of splatting a filter onto view data allows a filter to undergo a process similar to the scanning process. As a result, the kernel of the filter may vary through the different portions of the view data in a manner corresponding to the change in appearance of the structure of interest in the view data. Accordingly, the kernel of the filter may be more responsive to the appearance of the structure of the interest throughout the view data (e.g., across multiple views, cross-sections, etc.).

It should be appreciated that any filter having any characteristics and/or being responsive to any structure of interest or view data property may be used, as the aspects of the invention are not limited in this respect. In one embodiment according to the present invention, structure of interest is identified by splatting a 3D filter onto two dimensions of view data obtained from scanning an object assumed to contain at least some of the structure of interest to provide a filter splat responsive to subject matter of interest in the view data arising from the scanned structure of interest.

The term "splatting" refers herein to a process of projecting an n-dimensional function to n–i dimensions, where i is a non-zero integer less than n. For example, splatting may involve projecting a 3D function onto any one or combination of 2D planes of view data as shown in FIGS. 5A-5C. A splat of a 3D function may be computed in any number of ways, such as performing a volume integral over an appropriate domain of the 3D filter. In one embodiment, the splatting process is performed by taking line integrals through the filter along sampled rays extending from an X-ray source location through the filter, as discussed in further detail below. In one embodiment, the splatting process performs a similar transformation on a filter as the scanning process performs on an object being scanned. The term "filter splat" refers herein to the projection of a filter after the process of splatting (e.g., projecting) the filter. It should be appreciated that the filter splat operates as a filter on the view data and includes some domain over which the filter splat is defined (i.e., the filter kernel of the filter splat).

Figure 6:
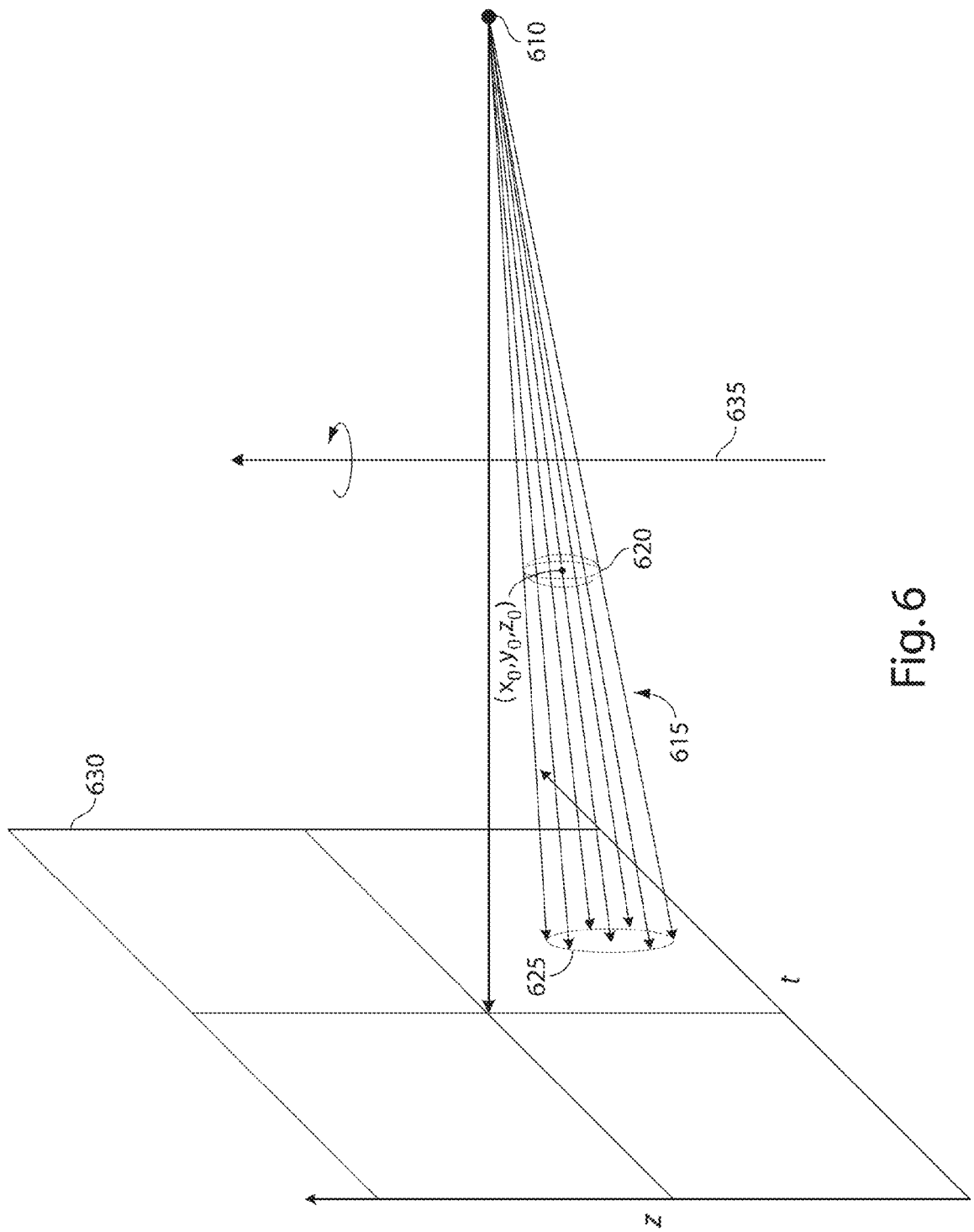
FIG. 6 illustrates one example of splatting a filter by computing line integrals along rays extending from an X-ray source location to a plane of view data, in accordance with one embodiment of the present invention.

FIG. 6 illustrates one method of splatting a 3D filter onto two dimensions of view data, in accordance with one embodiment of the present invention. Filter 620 may be any 3D function that can be used to filter the view data. For example, a 3D filter may be designed to have a strong response when applied to (e.g., convolved with) view data arising from structure of interest and a relatively weak response when applied to other structure or content in the view data. For simplicity, filter 620 is shown as an ellipsoid to represent generically the domain of the 3D filter (i.e., locations where the filter function is defined). The filter function can be any continuous or discrete function in object space, and operates as the kernel of the 3D filter. The filter function may be any of various 3D filters conventionally applied to reconstructed data, or any other function adapted to respond to structure of interest, as the aspects of the invention are not limited in this respect.

Filter 620 is centered at a location ($x_0$, $y_0$, $z_0$) in object space to test whether structure of interest was similarly situated in object space when the object was scanned. To test for the likelihood of the presence or absence of structure of interest, filter 620 may be splatted onto view 630. View 630 may correspond to view data in the (t,z) plane at a particular viewing angle $\theta_0$ of 3D view data of the scanned object. To determine the 2D splat of filter 620 on the 2D plane 630 rays (e.g., exemplary rays 615) emanating from source 610 that pass through filter 620 are generated, and the filter function is evaluated along each of the rays. In particular, a line integral of the filter function may be evaluated along each of the rays passing through filter 620.

The value of the line integral along each of the rays is then associated with a location in view 630 at which the respective ray intersects the 2D plane 630 to form filter splat 625. That is, filter splat 625 is a 2D discrete function in t and z, wherein each location ($t_i$, $z_i$) stores the value of the line integral of the filter 620 along a ray extending from source 610 to the location ($t_i$, $z_i$, and may also be associated with the underlying view data value at ($t_i$, $z_i$). The view data generally within the domain of filter splat 625 is referred to herein as the underlying view data. Filter splat 625 may then be used as an operator to process the underlying view data, e.g., by performing a convolution operation between the filter splat and the underlying view data, or otherwise comparing or applying the filter splat to the underlying view data.

It should be appreciated that rays 615 are exemplary and used to illustrate one embodiment of a splatting process. However, the filter function may be evaluated along any number of rays penetrating the filter at any number of locations, as the aspects of the invention are not limited in this respect. For example, the filter function may be sampled by a ray at a resolution that results in a line integral value that overlays every discrete location in the view data within the domain of filter splat 25, facilitating convolution or other filtering operations on the underlying view data. Alternatively, the filter splat may be over-sampled to provide line integral values at a sub-pixel resolution or under sampled such that line integral values are sparse with respect to the underlying view data.

As discussed above, filter splat 625 may be used as an operator on view data of an object to facilitate determining whether certain structures are present. In one embodiment, filter splat 625 is convolved with the underlying view data to obtain a filter output indicative of whether content generally responsive to the filter is present at the configuration of the filter. This can be viewed as a form of hypothesis testing. In particular, a hypothesis is made that structure having a particular density distribution and having a particular orientation and location existed during an X-ray scan of the object.

To test the hypothesis, a filter adapted to respond to the structure (typically by responding to the view data content resulting from the scan projections of the structure) is instantiated with a configuration corresponding to the hypothesis. For example, the filter is positioned and oriented to reflect location and orientation of the structure according to the hypothesis. The filter is then splatted into two dimensions (e.g., onto a view of the view data). The splatted filter may then be convolved or otherwise compared with the underlying view data to obtain a filter output (e.g., a single value) indicative of the likelihood that structure represented by the filter was present at the given configuration. For example, a strong response is highly suggestive that structure of interest was present. Similarly, a weak response suggests that the filter splat is operating on noise or content associated with structure other than the structure of interest.

It should be appreciated that a single filter splat provides information indicating the existence of structure configured approximately the same as the filter at a single view angle. However, if the structure of interest was present during the scan, its projection will likely be present, to some extent, in the view data across multiple views. As such, the process of splatting a filter onto a view and operating on the view data with the filter splat may be repeated for multiple views, for example, each angle θ from which view data was obtained. The information across the different views may be used to help support or contradict the hypothesis that structure of interest was present at the filter configuration during the scan.

For example, a single filter output value from a view $\theta_0$ may be vulnerable to false negatives or false positives. To make the likelihood measurement more robust, a 3D filter may be splatted on the next view (e.g., a view at the next viewing angle $\theta_1$) and the filter splat compared to the underlying view data of the second view. By repeating this process, each view in the 3D view data can provide an indication as to whether structure of interest was present at the configuration chosen for the filter, by examining the response of the filter on the content of the underlying view data across multiple views.

Figure 7:
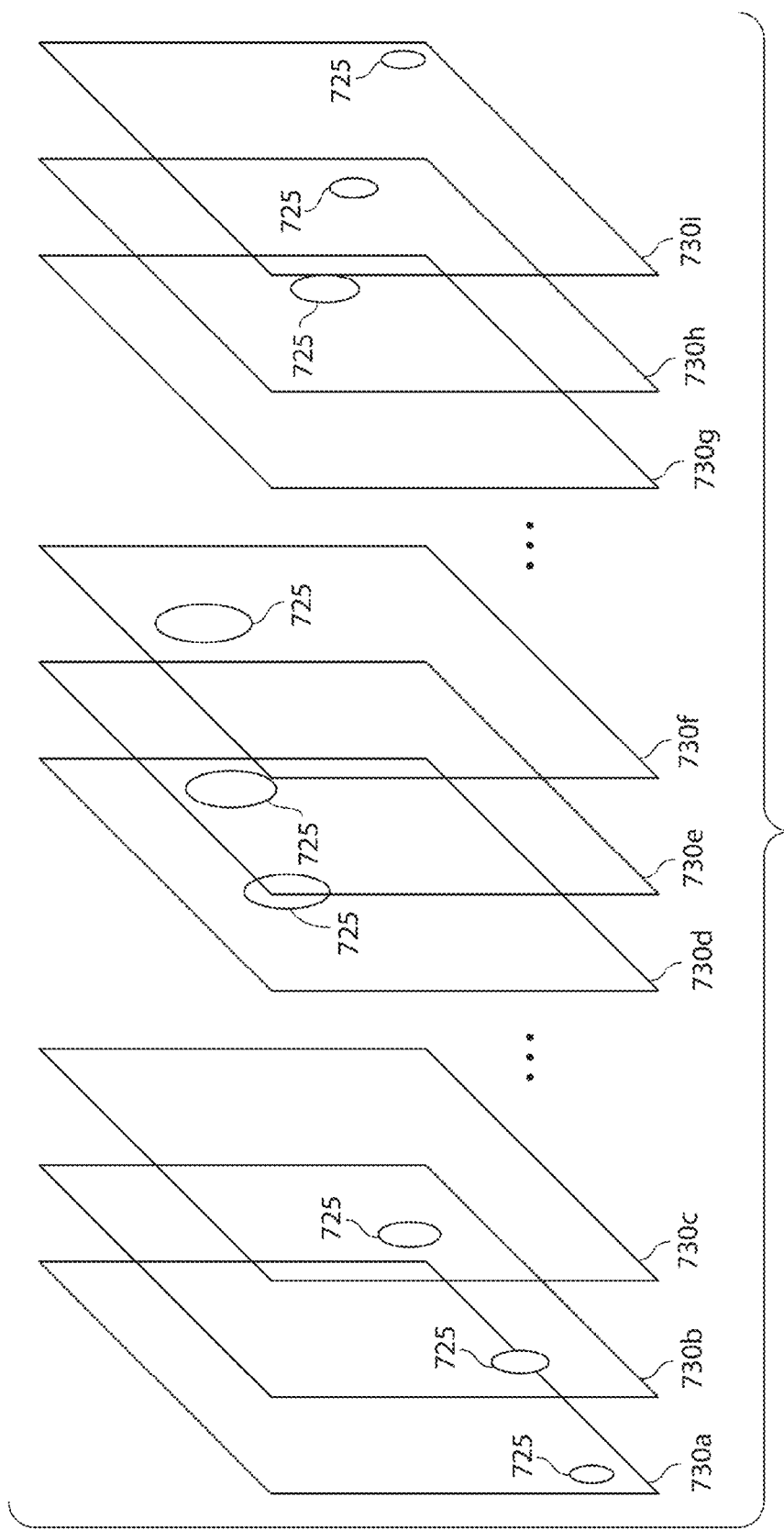
FIG. 7 illustrates a number of filter splats resulting from splatting a filter onto multiple views of 3D view data, in accordance with one embodiment of the present invention.

FIG. 7 illustrates the process of splatting a filter 720 onto the (t,z) plane of successive views of 3D view data obtained from scanning an object of interest, in accordance with one embodiment of the present invention. Planes 730a-730i are a sample of views of 3D view data. It should be appreciated that 3D view data may include hundreds, thousands, tens of thousands of views or more, and the illustrated views are merely exemplary samples of views across a view angle range from 0° to 180°. For example, planes 730a-730b may be three samples of views in the range of 0° to 30° view angle, planes 730d-730f may be view samples in the range between 75° to 105° view angle, and planes 730g-730i may be view samples in the range between 150° to 180° view angle.

Filter splats 725a-725i were computed from a volumetric filter positioned at a particular configuration in object space. Since a filter splat depends in part on the position of the filter relative to the X-ray source and the view plane, (e.g., depends on rays extending from the source to the view plane via the filter) the size and location of the resulting filter splat will vary from view to view as the X-ray source rotates about the filter (i.e., as the view angle θ is varied). As discussed above in connection with FIGS. 3A-3C and 4, a projected object will have an orbit as a function of θ that is generally sinusoidal shape, and which depends on the location of the object with respect to the central axis of rotation (e.g., axis 635 in FIG. 6). The orbit of filter splat 725 is shown schematically on sampled views 730a-730i.

Since the filter undergoes a transformation similar to the transformation performed by scanning the object, the filter splat adapts to changes in the appearance of the structure of interest and may be better suited to detect the subject matter arising from the structure of interest in the corresponding view. That is, the kernel of the filter is varied as a function of view angle to better respond to the appearance of the structure of the interest in the corresponding view. It should be appreciated that the filter kernel may be varied according to other variables such as cross-section, for example, by projecting the filter onto different planes of the view data. The kernel of the filter may be varied in any number of ways, as the aspects of the invention are not limited in this respect.

The filter splat associated with each view may then be compared with the underlying view data. For example, filter splat 725 may be convolved with the values of the view data onto which the filter was splatted, to provide multiple filter outputs indicating the likelihood of the presence of corresponding structure. By considering likelihood information derived from multiple views, the chances of arriving at an erroneous conclusion as to whether structure is present may be decreased. For example, a generally strong response from the filter across multiple views is more suggestive of structure of interest than a strong response in a single view. By analyzing the filter response across multiple views, false negative rates and false positive rates may be reduced. The filter outputs computed from each view may be analyzed in any manner. For example, the values may be summed or averaged to obtain a single likelihood value, or analyzed as separate values and/or compared to one another. The filter output from each slice may be used in a maximum likelihood statistical analysis, or in any other way, as the aspects of the invention are not limited in this respect.

It should be appreciated that a volumetric filter may be splatted on any number of views and any number of filter splats may be used to compute a likelihood value, as the aspects of the invention are not limited in this respect. For example, the filter may be splatted on each of n views taken of the object during the scan. Alternatively, a subset of the n views and/or a sampling of the views on which the filter is splatted may be chosen to reduce computation time. Similarly, any number of values computed by comparing a filter splat with the corresponding view data may be used in determining whether structure of interest is present in the object that was scanned.

Applicant has recognized that the data obtained from comparing a filter splat with the underlying view data at each angle from which the view data was obtained (e.g., by performing a filter splat comparison in each view) is equivalent to comparing the 3D filter with the reconstructed data, but for the higher resolution of the view data. For example, a convolution operation between a filter splat and the underlying view data in each of the views in given view data is equivalent to convolving the volumetric filter with the 3D reconstructed data.

Applicant has appreciated that a much higher resolution may be achieved by performing the filtering operation on the view data. Therefore, any of the various filtering operations conventionally performed on reconstructed data may be performed in view space without suffering the loss of resolution that is incurred during reconstruction. Accordingly, structure may be detected at higher resolutions (e.g., at the resolution of the view data rather than at the resolution of the reconstructed data).

As discussed above, filter outputs from filter splats operating on view data relate to the likelihood that the view data resulted from structure situated with approximately with the same configuration as the filter. That is, a given filter asserts a hypothesis about the presence of structure similarly situated. To determine the presence of structure elsewhere in the view data, multiple filters may be distributed throughout object space to assert hypotheses at different configurations. For example, object space may be partitioned into uniform or non-uniform regions and one or more filters may be positioned in each region to form hypotheses of the existence of structure throughout a desired portion of object space.

Figure 8:
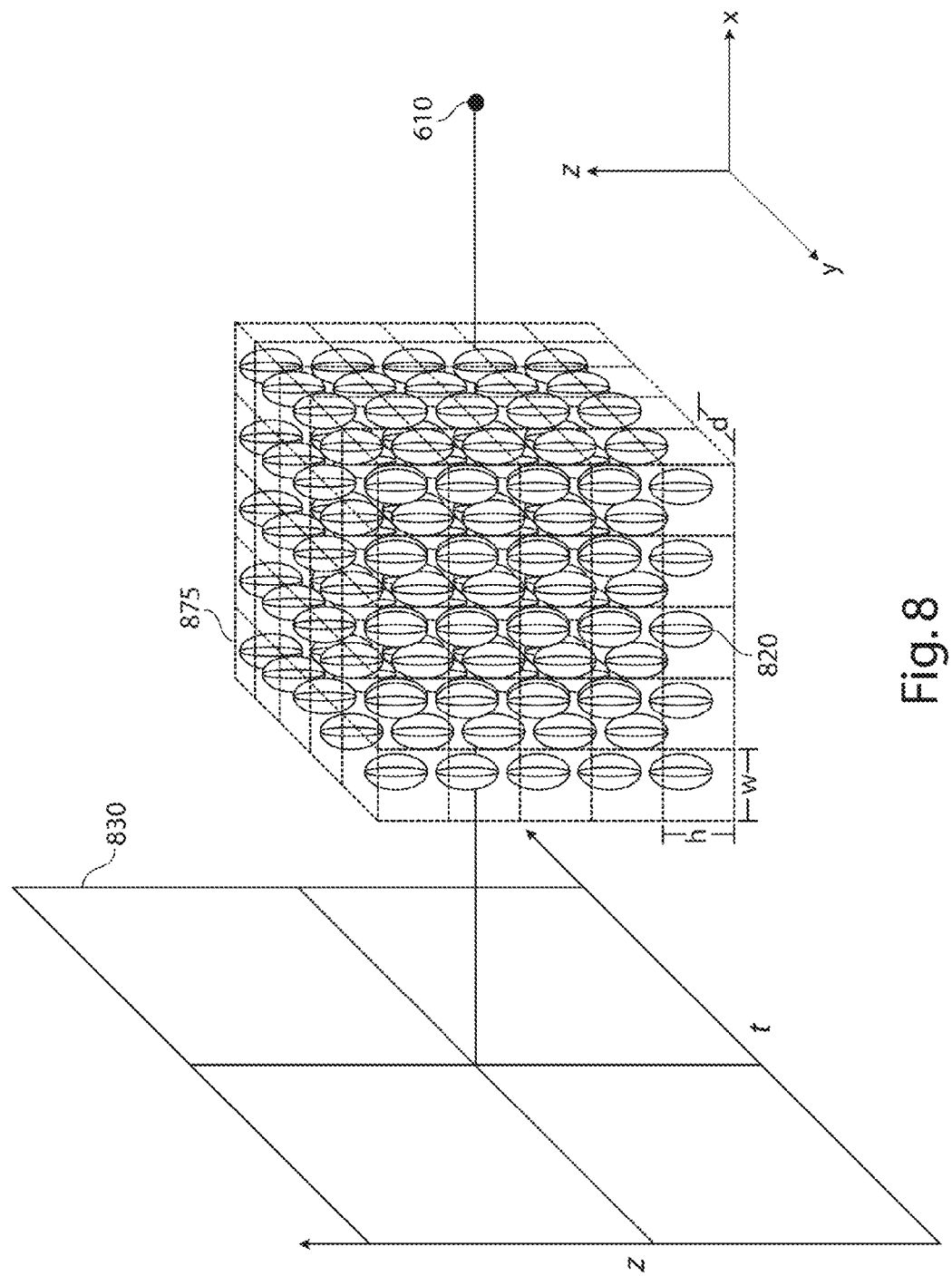
FIG. 8 illustrates positioning a number of filters throughout a logical tesselation of object space to be splatted onto view data, in accordance with one embodiment of the present invention.

FIG. 8 illustrates an object space partitioned into a regular 3D grid to form multiple hypotheses about the existence of corresponding structure. A portion of object space 875 is tessellated with regular Cartesian cubes, having a width w along the y-axis, a height h along the z-axis, and a depth d along the x-axis. One or more filters 820 may be positioned inside each cube at a desired orientation. Filters 820 are shown as ellipsoids to denote a generic filter that may be of any type. The filters in FIG. 8 are all illustrated as having the major axis of the ellipsoid aligned with the z-axis, however, the filters can have any desired orientation for which it is desired to test for the presence of structure of interest. Moreover, each cube may include more than one filter at different orientations such that each region provides multiple hypotheses, as described in further detail below.

After positioning the filters in partitioned object space, each filter may be splatted to two dimensions, for example, splatted to the (t,z) plane of a view of view data in which structure is being detected. The resulting filter splats may then be compared to the underlying view data to generate a value indicative of the likelihood of the presence of structure similarly situated. As discussed above, the splatting procedure may be repeated in any number of views to further support or contradict the hypothesis that structure exists. The likelihood information collected from each view may be analyzed to determine whether structure corresponding to the associated filter was present in the scanned object.

It should be appreciated that the size of the filter may be chosen to reflect the size of the structure being detected (i.e., to achieve detection at a desired resolution). For example, when the structure of interest is small, the regions in partitioned space may be decreased in size to reflect the dimensions of the structure being detected. In addition, the size of the filters may be varied to simultaneously detect structure of different dimensions within the view data. The view space filtering allows for detection of structure at a resolution conventionally not attainable by filtering reconstructed data.

In one embodiment, the structure being detected is blood vessels in an X-ray scan of biological tissue. In filter design, it is often desirable to model the characteristics of the subject matter being detected to best construct a filter responsive to the subject matter. Blood vessels may be modeled by cylindrical segments having an appropriate cross-sectional function that approximates the density distribution of the blood vessel. As discussed above, a blood vessel network often consists of a network of branching blood vessels of varying dimensions. A number of cylindrical segments together may form a model of a blood vessel network. As discussed above (and described in detail in the Ser. No. 10/871,265 application), filter outputs can be used to establish parameter values for a model configuration. The configured model may then operate as the representation of the object, may be further optimized, and/or used to make a determination about the object, such as a medical diagnosis.

Figure 9A:
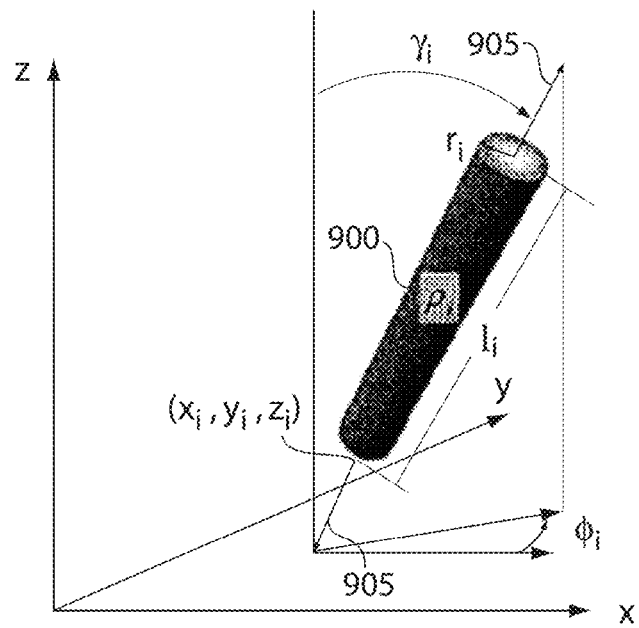
FIG. 9A illustrates a cylinder model in accordance with one embodiment of the present invention.

FIG. 9A illustrates one example of a cylindrical segment 900 that may be used as a component primitive in a cylinder network model of, for example, vessel structure such as human vasculature. A configuration of cylindrical segment 900 may be described by a number of parameters in a particular coordinate frame (i.e., parameterized in model space). As discussed above, model space may be the same 3D coordinate frame as an object or structure being modeled (i.e., model space and object space may describe the same space). For example, the position of cylindrical segment 900 may be described by a location of the cylindrical axis 905 at a point $(x_i, y_i, z_i)$ in space, for example, the origin or termination of the cylindrical segment. The orientation of cylindrical segment 900 may be specified by the angle $\phi_i$ from the x-axis and the angle $\gamma_i$ from the y-axis. Since cylindrical segment 900 is axially symmetric, its rotation about the z-axis may not need to be specified, although it may be parameterized as well. The length of the cylindrical segment may be specified by $l_i$ and the radius of the cylindrical segment 900 may be specified by $r_i$. Accordingly, cylindrical segment 900 may be configured by assigning values to the seven parameters $x_i, y_i, z_i, \phi_i, \gamma_i, l_i$, and $r_i$.

Figure 9B:
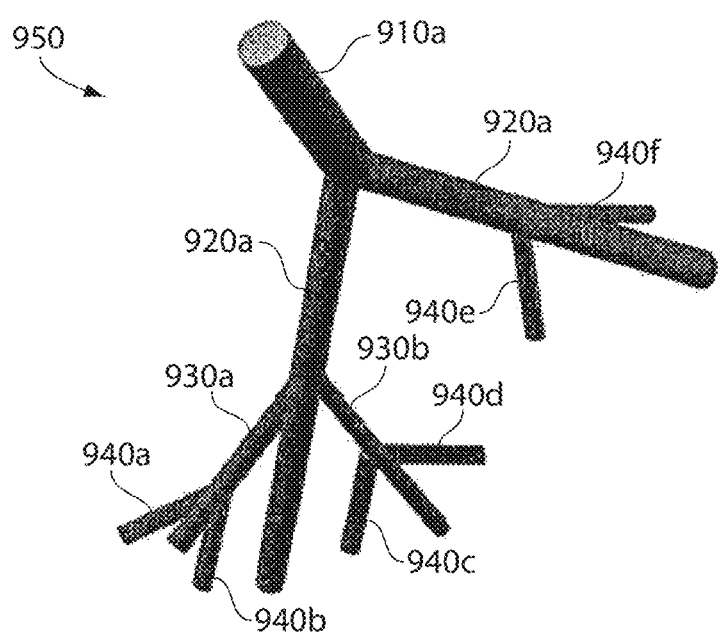
FIG. 9B illustrates a configuration of a cylinder network model built from the cylinder model in FIG. 9A, in accordance with one embodiment of the present invention.

FIG. 9B illustrates a configuration 950 of a cylindrical network model formed from a plurality of cylindrical segments arranged in a hierarchy. As discussed above, a vessel structure may include numerous vessels, each vessel having its own configuration in space to be described by the model. Configuration 950 includes a cylindrical segment 910a which branches into two cylindrical segments 920a and 920b, which further branch until the network terminates at the leaves of the hierarchy (i.e., cylindrical segments 920 branch into cylindrical segments 930, which in turn branch into segments 940, 950, 960 and so on).

Figure 10A:
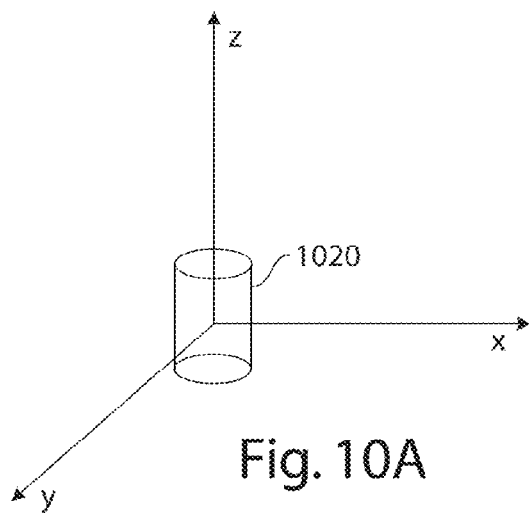
FIG. 10A illustrates a schematic of a filter adapted to respond to the cylindrical structure shown in FIG. 9A, in accordance with one embodiment of the present invention.

To detect structure that may appear at any number of locations, orientations and scales (e.g., blood vessels in a blood vessel network), it may be desirable to position filters having a variety of configurations to identify and/or detect structure that itself may be arbitrarily configured. FIG. 10A illustrates a filter configured to respond to cylindrically shaped (tubular) structure. Filter 1020 is depicted as a cylinder to demarcate the approximate domain of the filter and is symbolic of the structure it is configured to respond to and does not illustrate the actual filter function. It should be appreciated that the filter is actually a 3D function that responds in some detectable manner to tubular or cylindrically shaped objects. For example, filter 1020 may be a Gaussian function, one or more derivatives of the Gaussian function, a Hessian operator, etc. One embodiment, wherein filter 1020 has a radial second derivative Gaussian distribution, is described below.

Filter 1020 includes a number of parameters that together define the configuration of the filter. For example, to detect vessel structures, it may be desirable to vary the filter with respect to orientation and/or scale to account for the variation of the vessels in a vessel network. Accordingly, filter 1020 may include orientation parameters $\phi_i, \gamma_i$ to describe its orientation with respect to the x-axis and y-axis, respectively, and a radial parameter $r_i$ to describe the scale. It should be appreciated that the parameters of filter 1020 may correspond to parameters of the model of vessel structures in FIG. 9B. The parameterization of the filter allows the filter function to be configured to respond to structure of interest at a variety of locations, orientation and/or scales. The configuration of the filter parameters at which the filter is the most responsive may indicate the configuration of the underlying structure in the view data. As discussed above, the cylinder is merely symbolic of the domain of the filter function and the parameterization of any particular filter function may depend on the function itself. For example, the σ of a Gaussian filter function may operate as the scale parameter.

Figure 10B:
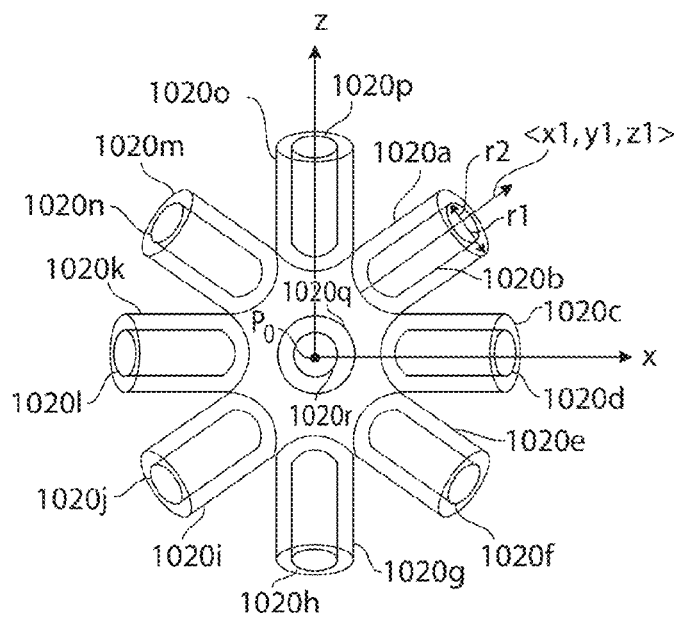
FIG. 10B illustrates an example the filter of FIG. 10A positioned at a number of different orientations and scales to form a filter cluster, in accordance with one embodiment of the present invention.

FIG. 10B illustrates a plurality of the filters 1020 parameterized to form a cluster providing a wide range of hypotheses about how the structure is configured. Filter cluster 400 includes multiple filters 1020 positioned at a number of different orientations and scales, forming a filter bank adapted to test multiple hypotheses about the existence of structure at different configurations. For example, cylindrical filter 1020*a* has a radius $r_1$ and a longitudinal axis oriented along vector $<x_1, y_1, z_1>$, which has orientation parameters $\phi_i, \gamma_i$. Cylindrical filter 1020*b* has a radius of $r_2$ and is oriented along the same vector $<x_1, y_1, z_1>$. Similarly, a selected number of other cylindrical filters (e.g., filters 1020*a*-1020*r*) are distributed at various orientations and scales to provide multiple hypotheses at a given location in space. It should be appreciated that, to better illustrate the orientations, the cylinders are not shown as having a common location, however, each of the filters 1020 may be given a common location point $P_0$.

Figure 10C:
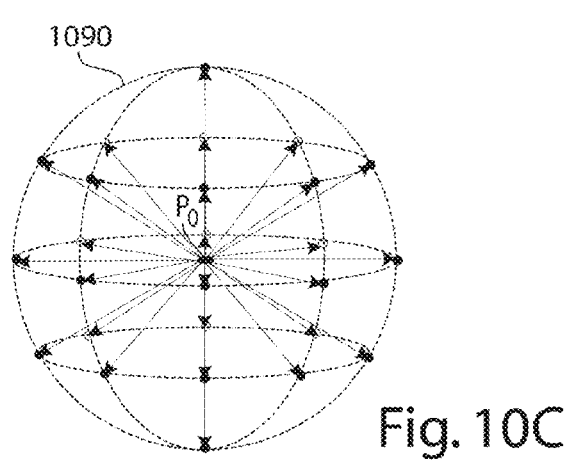
FIG. 10C illustrates one example of sampling object space to determine orientations of filters in a filter cluster, in accordance with one embodiment of the present invention.

In one embodiment, the orientations of filters in a filter cluster located at a point $P_0$ are selected by sampling a 3D space at $\pi/2$ intervals over the $4\pi$ directions, as shown in FIG. 10C. In particular, any orientation in 3D may be described by the direction of a vector from a center point $P_0$ to a surface of a sphere 1090. One sampling of this orientation space includes providing a vector $<x,y,z>$ from center location $P_0$ to each of the twenty-six locations of the 3D space sampled every $\pi/2$ radians. By symmetry, a cylinder positioned at $P_0$ and oriented along vector $<x_0,y_0,z_0>$ is identical to a cylinder positioned at $P_0$ and oriented along vector $<-x_0,-y_0,-z_0>$. Accordingly, in one embodiment, the thirteen unique orientations are used to form a filter cluster. A filter may then be provided at location $P_0$ for each sampled orientation. In addition, filters at one or more scales (e.g., filters being assigned different radii) may be provided at each orientation.

It should be appreciated that any of a filter's parameters may be varied to provide additional hypotheses of the existence of structure similarly configured. A filter cluster may comprise any type of filter that responds to structure of interest and may include filters of different types. For example, a combination of different filter types may be associated with a point $P_0$ to test for the existence of different or the same structure generally located at point $P_0$. In addition, any number of filters at any configuration may be used, as the invention is not limited in this respect. The number of orientations and scale at which filters are distributed may depend on the type of structure that is being identified in the view data. For example, when vessels of the human body are being detected, the scale of the filters may correspond approximately to the scale of the vessels being detected. When vessels at multiple scales are being detected, filters may be provided by distributing filters over a wide range of scales.

A filter cluster may be positioned at sample locations P in object space to generate hypotheses at multiple locations. FIG. 11 illustrates a filter cluster 1100 distributed over a selected volume of object space. In one embodiment, the filter 1020 illustrated in FIG. 10A may be assigned sampled orientations as described in FIG. 10C to form filter cluster 1100. The filter cluster may then be distributed at various locations in object space to test for the presence of structure similarly located. For example, each partitioned region of tessellation 1175 may include a filter cluster comprising a filter oriented at the thirteen orientations of a 3D space sampled over the $4\pi$ directions at $\pi/2$ radian intervals. In addition, one or more filters having different scales may be provided at each of the orientations. It should be appreciated that any filter cluster distributed in any fashion (e.g., uniformly or non-uniformly) may be used, as the aspects of the invention are not limited in this respect.

The filters in each of the filter clusters may then be splatted to two dimensions, such as onto the (t,z) plane 1130 of view data obtained from scanning an object of interest. The filter splats may then be compared with the underlying view data to generate a measure of likelihood of structure for the corresponding configuration of the filter. As a result, a filter cluster may produce a likelihood value for each of the filter configurations in the cluster, generating a vector $l=<l_1, l_2, l_3, \ldots, l_i>$, where l is a filter output and i is the number of filter configurations in the filter cluster. For example, the filter clusters described in FIGS. 10B and 10C produce a vector l of length 13 if a single scale is used (i.e., each filter configuration has the same radius r), a vector l of length 26 if two scales are used, etc.

Each filter cluster may be splatted onto multiple views of the view data. As a result, each cluster may generate a number of values equal to the product of the length of the vector l and the number of views onto which the cluster is splatted. This set of data, referred to herein as filter cluster data, provides a likelihood measure for the existence of structure positioned at the location of the corresponding filters in the cluster. That is, at each location in object space where a filter cluster is positioned, a hypothesis of structure existing at that location is made at multiple values for each varied filter parameter (e.g., a hypothesis may be made over multiple orientations and/or scales). The resulting filter cluster data from each filter cluster may be analyzed in any number of ways to determine whether the structure hypothesis is true, and which filter configurations most likely correspond to the actual configuration of the structure.

For example, the components of a vector l may be thresholded and peaks selected as the most likely configuration of the structure. Various probabilistic models may be used to determine the likelihood that structure exists at a particular configuration given the filter cluster data. As discussed above, the operation of convolving a filter splat from a 3D filter with the underlying view data in each of the views is equivalent to performing the convolution of the 3D filter with the 3D reconstructed data, except at the higher resolution of the view data. Accordingly, the various methods used to interpret conventional filter data from reconstructed data may be used to analyze the filter data from the view data to detect, identify and/or determine whether structure of interest is present.

It should be appreciated that as the number of filters positioned in object space is increased, the process of the splatting the filters becomes more computationally expensive. In addition, as the size of the view data increases, the number of splatting operations may also need to be increased. For example, if each of the filters positioned in object space is splatted onto each view taken over a view angle range of 180°, the number of splatting operations may be relatively large. Applicant has appreciated that, by symmetry, the number of splatting operations may be reduced, often significantly. In particular, filter splats computed for particular filters at certain view angles may be reused at different view angles, reducing the total number of splatting operations that need be performed.

Figure 12:
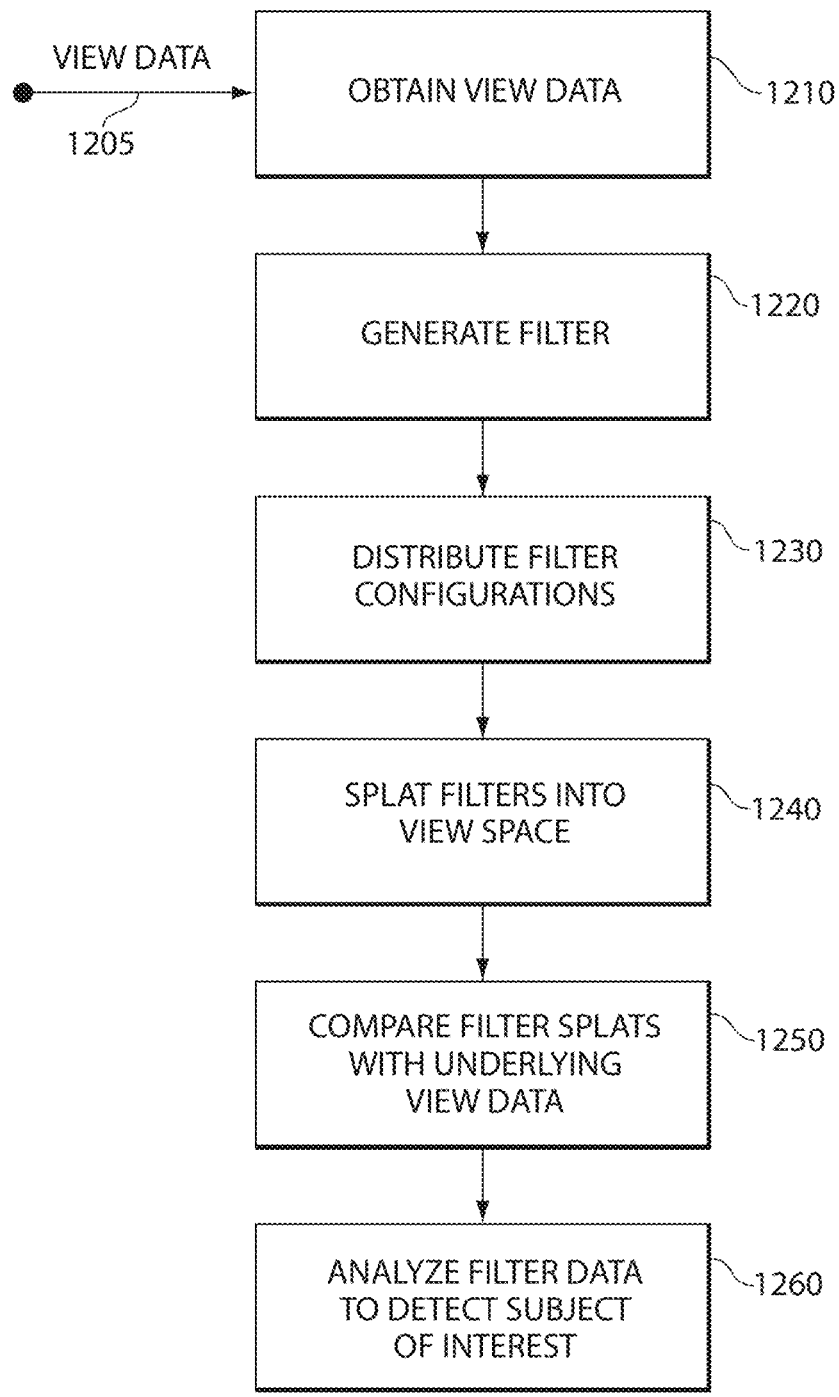
FIG. 12 illustrates a method of detecting subject matter of interest in view data by splatting a filter adapted to respond to the subject matter of interest onto the view data, in accordance with one embodiment of the present invention.

FIG. 12 illustrates a method of detecting structure of interest in view data obtained from scanning an object assumed to contain at least some of the structure of interest, in accordance with one embodiment of the present invention. In act 1210, view data 1205 of an object of interest is obtained. The view data may correspond to 3D information formed from scanning a plurality of two-dimensional slices of the object of interest. View data 1205 may be obtained in any suitable way, as the invention is not limited in this respect. For example, the view data may be obtained directly from an X-ray scanning device, from a storage medium storing previously obtained view data, over a network, etc.

In act 1220, a filter adapted to respond in a detectable way to the structure of interest is generated. For example, the filter may be configured to have a strong response when operating on view data resulting from the structure of interest and a weak response when operating on noise or content other than the structure of interest. Alternatively, the filter may be configured to respond in a pattern or other detectable characteristic in the presence of the subject matter of interest. For example, the filter may be configured such that filter data resulting from application of a filter over a selected region of the view data has peaks, zero-crossings or other identifying patterns that indicate the presence of the structure of interest. Any filter configured to respond to or extract detectable properties of the structure of interest may be used, as the aspects of the invention are not limited in this respect.

In act 1230, the selected filter is distributed in object space at a desired number of configurations. For example, the filter may be distributed throughout object space at locations spaced apart to achieve a desired resolution in the detection of the structure of interest. At each location, the filter may be provided with multiple configurations, such as providing the filters at a number of different orientations and/or scales. The filter may be distributed in object space in any way and at any number of configurations, as the aspects of the invention are not limited in this respect.

In act 1240, each of the filters distributed in object space are splatted into view space, to provide a plurality of filter splats to be compared with the underlying view data. For example, each of the filters may be projected onto one or more views of the view data by computing line integrals through the filter function along a number of rays penetrating the filter. Other discrete and continuous methods may be used to splat the configured filters to provide filter splats to operate on the view data, as the aspects of the invention are not limited in this respect. In one embodiment, the configured filters distributed in object space are splatted onto each view of the 3D view data.

In act 1250, the filter splats are compared with the underlying view data. For example, each filter splat may function as an operator on the view data over which the filter was projected to produce a filter output. The filter operation may be a convolution operation or other comparison of the filter splat values with the underlying view data. In one embodiment, the filter splats resulting from the differently configured filters at a given location in object space are convolved with the underlying view data in each view onto which the filter is splatted, each convolution operation providing the response of the underlying view data with the filter at the respective filter configuration. This operation may be repeated in each view to provide the equivalent operation of convolving the 3D filter with 3D reconstructed data, but at the increased resolution of the view data.

In act 1260, the filter outputs are analyzed to determine the likelihood that structure of interest is present at the configuration of the corresponding filter. For example, the filter outputs resulting from a particular location may (e.g., filter outputs resulting from each filter in a particular filter cluster) form a vector indicative of the likelihood of structure of interest being present in a respective view and having the configuration of the respective filters. Accordingly, each filter cluster provides a vector filter output in each view onto which the filter cluster is projected. The vectors over multiple views provide an indicator of whether or not structure is present at a given location, and at what configuration (e.g., orientation and/or scale). The vectors across multiple views resulting from a given filter cluster may be compared to provide a likelihood measure that structure of interest is present. For example, the vectors from a given filter cluster may be summed or averaged to provide a single likelihood vector at each location at which a filter cluster is provided.

A likelihood vector may then be analyzed in any number of ways to determine whether structure of interest is present. For example, a strong response (e.g., a large value) in one of the components of the likelihood vector relative to responses in other components may indicate the presence of structure of interest having the configuration associated with the predominant component. Accordingly, detection of the structure may include inspecting peaks and/or strong responses in the likelihood vectors. Alternatively, the likelihood vectors may be used in a probabilistic framework to determine the likelihood that structure is present. For example, a hypothesis that structure exists at a given location may be tested by determining the probability that the computed likelihood vectors resulted from the presence of structure. In addition, filter outputs may be analyzed for patterns such as peaks, zero-crossings, edges or other detectable properties in much the same way as conventional filter outputs are analyzed. Any method may be used to analyze the filter outputs to determine whether structure of interest is present in a location and configuration indicated by the associated filter, as the aspects of the invention are not limited for use with any particular analysis technique.

B. Filter Design for Tubular Structure

As discussed above, filter design may depend on the type of structure being detected. In general, a filter is designed to be responsive to the subject matter of interest in the view data, or to produce a detectable property or pattern when operating on the view data. In one embodiment, the second derivative of the Gaussian function is used to form a filter for identifying the presence or absence of tubular structure in view data obtained from scanning an object of interest. For example, the filter may be used to detect vessel structures in view data obtained from scanning a human patient or other biological subject containing vasculature.

The following describes one embodiment of a filter designed to respond to subject matter of interest in view data arising from tubular structure, and the response of the projected filter splat. One embodiment of determining the likelihood that subject matter of interest is present from the filter data using Bayesian analysis is set forth in section C below. One embodiment of a filter for identifying tubular structure, for example, blood vessels, includes a three dimensional filter function having the second derivative of the Gaussian function as a radial distribution (e.g., in the XY plane of object space) and a Gaussian distribution along the z-axis. That is, the filter has a second derivative Gaussian cross-section having a radius that falls off as the Gaussian. The filter function may be expressed as:

$$h_{rr} = \left(\frac{r^2}{\sigma_r^2} - 1\right) e^{\frac{-1}{2\sigma_r^2}(r^2)} e^{\frac{-1}{2\sigma_z^2}(z^2)} \quad (1)$$

Figure 13:
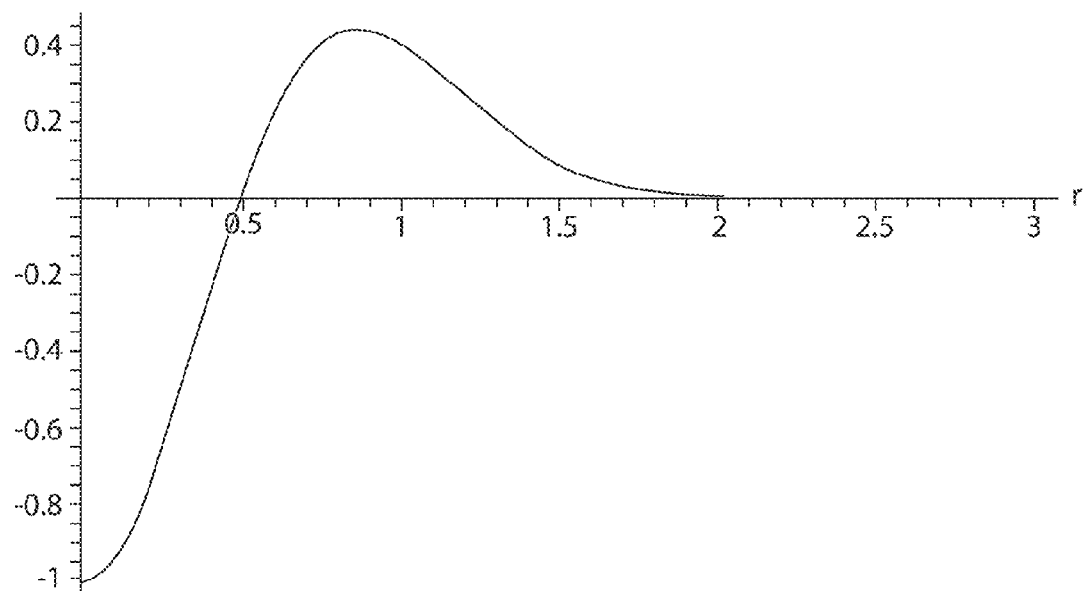
FIG. 13 illustrates a profile of one example of a filter adapted to respond to tubular structure, in accordance with one embodiment of the present invention.

The profile (i.e., the radial cross-section) of this filter for $\alpha=0.5$ is shown as a function of r in FIG. 13. It should be appreciated that the profile is symmetric for negative values of r. As discussed above, a filter may be applied to view data by splatting the filter to two dimensions, a process which includes taking a volume integral of the filter. It may be desirable to have the volume integral of the filter vanish such that the filter does not respond to view data having a constant density. However, the $2^{nd}$ derivative of the Gaussian does not integrate to zero. Rather, $$\int_0^\infty \left(\frac{r^2}{\sigma_r^2} - 1\right) e^{\frac{-1}{2\sigma_r^2}(r^2)} e^{\frac{-1}{2\sigma_z^2}(z^2)} r\, dr\, dz = 1 \quad (2)$$

The integral can be forced to zero by providing an offset, $$\int_0^\infty \left(\frac{r^2}{\sigma_r^2} - 2\right) e^{\frac{-1}{2\sigma_r^2}(r^2)} e^{\frac{-1}{2\sigma_z^2}(z^2)} r\, dr\, dz = 0 \quad (3)$$

For purposes of illustrating certain characteristics of the above filter, a tubular structure is modeled as a line impulse. The line impulse may be parameterized as an infinite line of the parameter t passing through an origin at an angle $\alpha$ from the radial axis r (i.e., from the XY plane). The line may be parameterized as, $$r(t)=t\,\text{Cos}\,\alpha$$

$$z(t)=t\,\text{Sin}\,\alpha \quad (4)$$

To illustrate how the filter responds to line impulses at various angles $\alpha$, the parameterized line of equation 4 may be substituted into equation 3, $$h_{rr}(t, \alpha) = k \frac{1}{\sigma_r^2} \left(\frac{t^2 \text{Cos}^2 \alpha}{\sigma_r^2} - 2\right) e^{\frac{-1}{2\sigma_r^2}(t^2 \text{Cos}^2 \alpha)} e^{\frac{-1}{2\sigma_z^2}(t^2 \text{Sin}^2 \alpha)} \quad (5)$$

Figure 14:
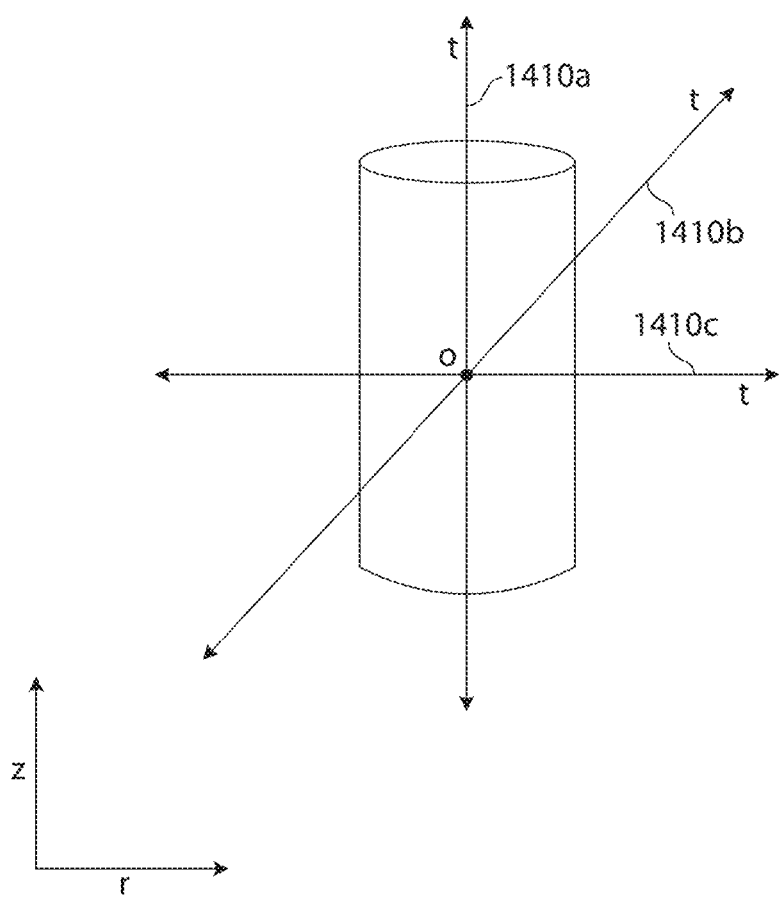
FIG. 14 illustrates symbolically one example of a filter adapted to respond to tubular structure with three parameterized lines penetrating the filter at three different angles $\alpha$, in accordance with one embodiment of the present invention.

FIG. 14 symbolically illustrates the filter described in equation 3. As discussed above, filter 1420 generally demarcates the domain of the filter. As shown in equation 3, the filter function describes a second derivative Gaussian in the radial direction that falls off as the Gaussian in the z direction, and does not describe a cylinder. However, to demonstrate how the filter responds to line impulses, the filter is represented as a cylinder. Three parameterized lines 1410a, 1410b and 1410c at $\alpha=\pi/2$, $=5\pi/12$ and $\alpha=0$, respectively, from the r-axis are shown in FIG. 14. Line impulses 1410 illustrate three possible ways in which an arbitrarily positioned filter may be located with respect to structure of interest (e.g., line impulses).

Figure 15A:
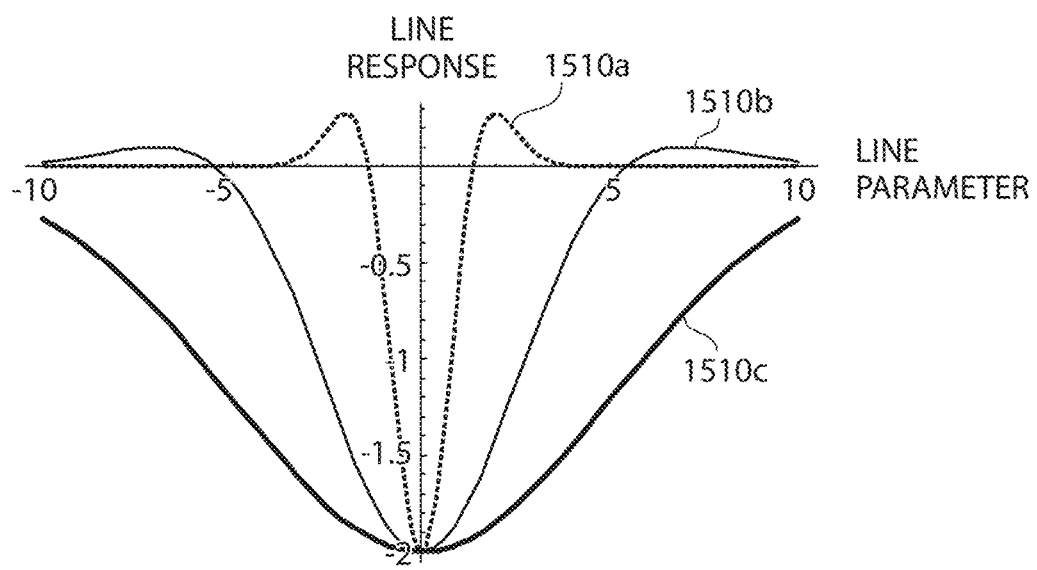
FIG. 15A illustrates profiles of a filter function of one example of the filter in FIG. 14 along the parameterized lines illustrated in FIG. 14, in accordance with one embodiment of the present invention.

FIG. 15A illustrates profiles of the filter function along each of lines 1410 with respect to the line parameter t. In particular, profile 1510a corresponds to the variation of the filter function described in equation 5 along line impulse 1410a, profile 1510b corresponds to the variation of the filter function along line impulse 1410b and profile 1510c corresponds to the variation of the filter function along line impulse 1410c. The line impulse response may be found by integrating the profiles over t. For an arbitrary $\alpha$, the line impulse response may be expressed in closed form as, $$h_\alpha(\alpha) = \frac{k}{\sigma_r^2} \int_{-\infty}^\infty \left(\frac{t^2 \text{Cos}^2 \alpha}{\sigma_r^2} - 1\right) e^{\frac{-1}{2\sigma_r^2}(t^2 \text{Cos}^2 \alpha)} e^{\frac{-1}{2\sigma_z^2}(t^2 \text{Sin}^2 \alpha)} dt \quad (6)$$

Accordingly, the line impulse response may be found at desired values of $\alpha$. To determine how the filter responds to line impulses at various orientations, equation 6 may be evaluated over some range of interest, for example, from $\alpha=0$ to $\alpha=\pi/2$. The filter responds most strongly to a line impulse at $\alpha=\pi/2$ when the filter and the line impulse have the most similar orientation. Similarly, the filter responds weakest at $\alpha=0$ when the filter and the line impulse have generally orthogonal orientations.

Figure 15B:
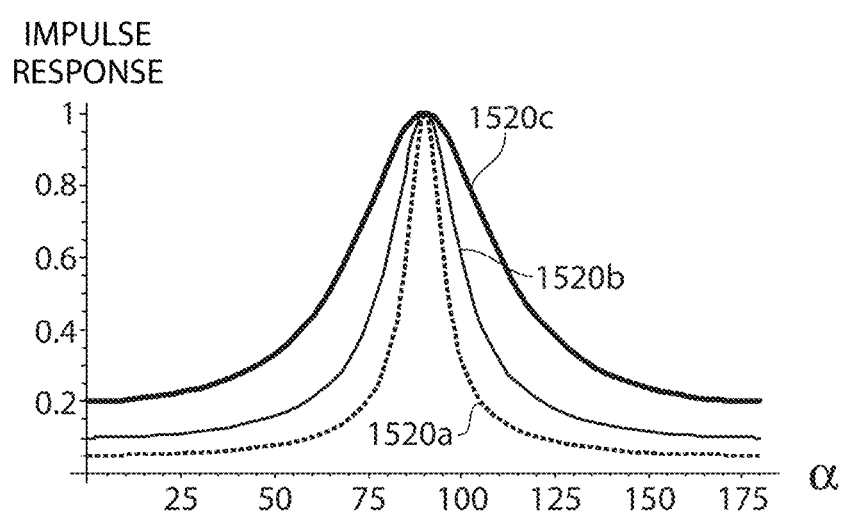
FIG. 15B illustrates profiles of impulse line responses through the filter function of the filter in FIG. 14 using three different sharpness ratios $\epsilon$, in accordance with one embodiment of the present invention.

It may be desirable to normalize the line impulse response so that the peak response is +1. The shape of the filter may be controlled by varying the width of the radial profile of the second derivative (i.e., $\sigma_r$ of the filter function) and by varying how quickly the radial distribution decays in the z-direction (i.e., $\sigma_r$ of the filter function). The normalization function may be expressed as, $$f_i(\alpha_c, \rho; \varepsilon) = \rho \frac{\varepsilon}{2} \frac{(\text{Cos}^2((\alpha_c - \alpha_i) + 2\varepsilon^2 \text{Sin}^2((\alpha_c - \alpha_i))}{(\text{Cos}^2(\alpha_c - \alpha_i) + \varepsilon^2 \text{Sin}^2(\alpha_c - \alpha_i))^{\frac{3}{2}}}. \quad (7)$$

where, the ratio, $$\varepsilon = \frac{\sigma_r}{\sigma_z}$$

controls the sharpness of the filter response, and $\rho$ is an impulse density scaling factor. FIG. 15B illustrates impulse line responses for three different sharpness ratios $\epsilon$. In particular, the impulse response 1520a illustrates the integral of the line impulse profile over a range of orientations from $\alpha=0$ to $\alpha=\pi$ with a sharpness ratio $\epsilon=0.4$. Similarly, impulse response 1520b illustrates the impulse response of the filter function with respect to $\alpha$ for $\epsilon=0.4$, impulse response 1520c shows the filter response at $\epsilon=0.1$. As illustrated, the filter response is maximum at $\alpha=\pi/2$, when the filter function is aligned with the line impulse.

Figure 16A:
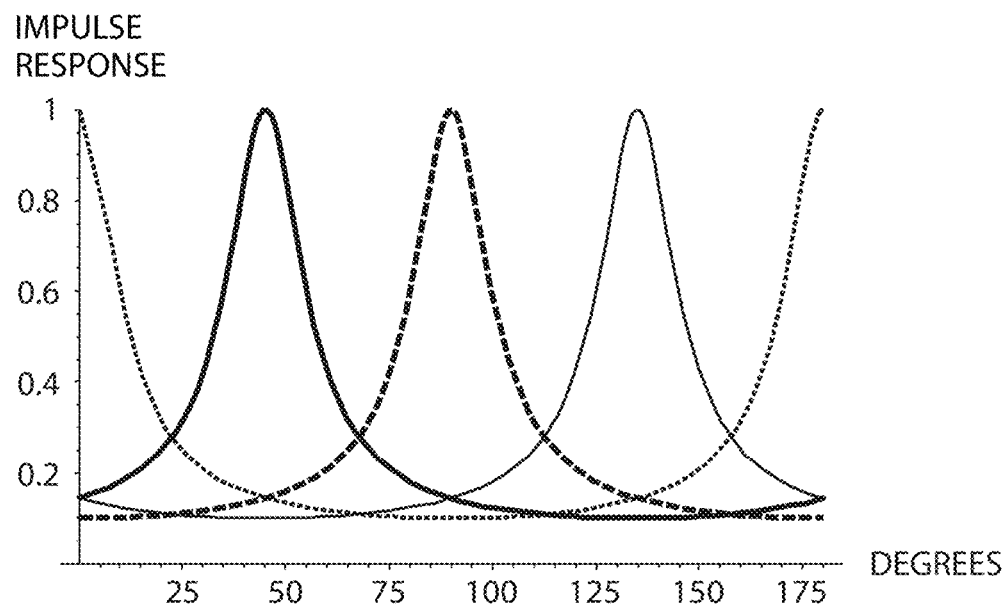
FIG. 16A illustrates line impulse responses over a range of angles $\alpha$ of four filters oriented every 45 degrees, in accordance with one embodiment of the present invention.
Figure 16B:
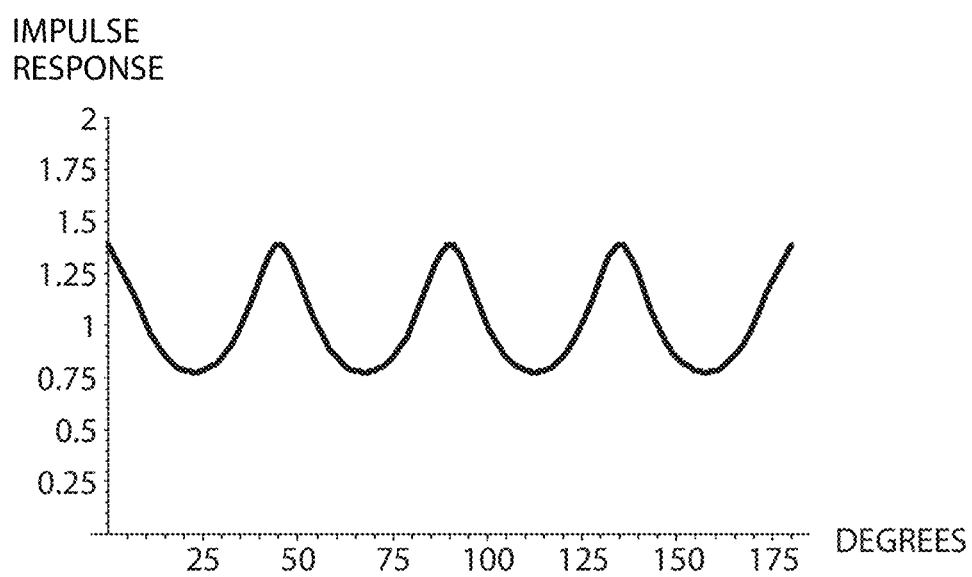
FIG. 16B illustrates the sum of the impulse responses shown in FIG. 16B, in accordance with one embodiment of the present invention.

FIG. 16A illustrates the line impulse responses integrated over the interval $\alpha=[0, \pi]$ with a normalization ratio $\epsilon=0.2$ using four filters oriented every 45° over the integration interval. As shown, the filter bank has maximum response at $\pi/2$ for each 45° location. The sum of the filter responses is illustrated in FIG. 16B. The response of the filter bank to structure, for example, a cylinder modeling tubular structure in the view data can be found by integrating over the cross-section of the cylinder. That is, the impulse response of the filter designed according to equation 5 can be used to determine the response of the filter to any structure by integrating over the modeled function for the structure of interest.

As discussed above, the filter data obtained from filtering the view data in view space may be used to determine the likelihood that the response to the filter resulted from the structure being detected or whether the response resulted from noise or other subject matter or content. There are numerous methods of processing the filter data to make this determination, including the various methods currently used in conventional filtering of reconstructed data to categorize, classify and/or otherwise identify filter responses resulting from subject matter of interest. For example, empirical methods such as analyzing the features of the filter response to identify characteristic patterns such as peaks, zero-crossings, maximal/minimal gradients, etc., may be used. Any of various statistical methods may be used to generate the likelihood that a filter response resulted from subject matter of interest.

In one embodiment, a Bayesian framework is used to determine the likelihood of the presence of subject matter of interest and to determine the parameters of that subject matter (e.g., to determine the orientation, scale, etc. of the subject matter of interest), as described below. It should be appreciated that any method of analyzing the filter data may be used, as the aspects of the invention are not limited in this respect.

C. Bayesian Framework for Hypothesis Testing

The following hypothesis testing framework is one exemplary formulation that may be used to determine the likelihood that subject matter of interest is present in view data based on the filter data output by a filter splat. Probabilistic methods such as the one described below are known in the art. Hypothesis testing includes determining the likelihood that structure of interest modeled by a selected model parameter vector $\Psi$ is present based on observed data D. It should be appreciated that model parameter vector $\Psi$ may be chosen to model any desired structure of interest. In one embodiment, the structure of interest is tubular structure modeled by cylindrical segments having a model parameter vector defined by, $\Psi=\{a,\alpha,\phi,\Delta r,\rho\}$: cylinder radius, elevation angle, azimuthal angle, radial offset, density. The posterior probability distribution for a set of models, $M_i$ is given by, $$p(M_i, \Psi \mid f_0, f_1, \ldots f_{n-1}) = \frac{p(f_0, f_1, \ldots f_{n-1} \mid M_i, \Psi)}{p(f_0, f_1, \ldots f_{n-1})} p(M_i, \Psi)$$

The posterior probability can be processed in numerous ways including: 1) marginalizing out the unknown parameters, resulting in the marginal posterior (MP) probability; and 2) finding the parameter values that maximize the posterior density (MAP) and computing the probability of the model as the maximum joint probability for $\Psi=\hat{\Psi}$ using the determined parameter values. The latter expression only provides the joint probability that we have model $M_i$ when the parameter values are in an interval around $\hat{\Psi}$. If there are multiple solutions with nearly the same probability, the estimate of the model probability may not locate the optimal solution. In either case, the model that should be selected is the one that maximizes either of the expressions in equation 8 and equation 9 below.

$$p(M_i) = \int_\Psi p(M_i, \Psi \mid f_0, f_1, \ldots f_{n-1}) d\Psi \quad MP \tag{8}$$

$$p(M_i, \hat{\Psi}) = \underset{\Psi=\hat{\Psi}}{\mathrm{argmax}}\, p(M_i, \Psi \mid f_0, f_1, \ldots f_{n-1}) \quad MAP \tag{9}$$

In one embodiment, there are n filters for the one-dimensional orientation of a cylinder in a meridian plane and these filters are spaced equally in object space. Each filter, $f_i$, is centered on an angle, $\alpha_i$. Given a set of parameters, $\Psi$, a cylinder would have a specific ideal response, $[f_0, f_1, \ldots f_{n-1}]_{Cyl}(\Psi)$. In one simple example, the parameter set is $\Psi=\{\alpha_c, \rho\}$, the unknown orientation of the cylinder model and its density. For example, if the cylinder is the line impulse, then the filter outputs are given by, $$f_i(\alpha_c, \rho; \varepsilon) = \rho \frac{\varepsilon}{2} \frac{(\cos^2((\alpha_c - \alpha_i) + 2\varepsilon^2 \sin^2((\alpha_c - \alpha_i)))}{(\cos^2(\alpha_c - \alpha_i) + \varepsilon^2 \sin^2(\alpha_c - \alpha_i))^{\frac{3}{2}}} \tag{10}$$

The actual response $[f_0, f_1, \ldots f_{n-1}]_D$ will differ from the ideal response due to noise. Suppose that, $$[f_0, f_1, \ldots f_{n-1}]_D = [f_0, f_1, \ldots f_{n-1}]_{Cyl}(\Psi) + [\eta_0, \eta_1, \ldots \eta_{n-1}]_{Noise} \tag{11}$$

and that each filter noise element is independent and normally distributed with the same variance, $\sigma$. In this case, the difference between the ideal and actual filter responses may be taken, to form the expression, $$p(F_D \mid Cyl, \Psi) = \frac{1}{\left(\sqrt{2\pi}\,\sigma\right)^n} e^{\frac{-1}{2}(F_D - F_{Cyl}(\Psi))^t \Sigma^{-1}(F_D - F_{Cyl}(\Psi))} \tag{12}$$

where $F_D = [f_0, f_1, \ldots f_{n-1}]_D$ and $F_{Cyl}(\Psi) = [f_0, f_1, \ldots f_{n-1}]_{Cyl}(\Psi)$ and $\Sigma^{-1} = \mathrm{Diag}\left[\frac{1}{\sigma^2}\right]$ Suppose the assumption of a model where nothing is in the filter volume, i.e., $$F_{nothing} = [0, 0, \ldots 0]. \tag{13}$$

$$p(F_D, \mathrm{Nothing}) = \frac{1}{\left(\sqrt{2\pi}\,\sigma\right)^n} e^{\frac{-1}{2}(F_D - F_{Nothing})^t \Sigma^{-1}(F_D - F_{Nothing})}$$

$$= \frac{1}{\left(\sqrt{2\pi}\,\sigma\right)^n} e^{\frac{-1}{2}(F_D)^t \Sigma^{-1}(F_D)}$$

The probability of the data overall given these two models is, $$p(F_D) = \left[\int_\Psi p(F_D \mid Cyl, \Psi) p(\Psi \mid Cyl) d\Psi\right] p(Cyl) + \tag{14}$$

$$p(F_D \mid \mathrm{Nothing}) p(\mathrm{Nothing})$$

where $p(\Psi|Cyl)$ is the prior distribution on cylinder parameters. The marginal posterior (MP) probability of a cylinder being present in the data is given by, $$p(Cyl \mid F_D) = \frac{\left[\int_\Psi p(F_D \mid Cyl, \Psi) p(\Psi \mid Cyl) d\Psi\right] p(Cyl)}{p(F_D)} \quad MP \tag{15}$$

The MAP probability for the cylinder is, $$p(Cyl, \hat{\Psi} \mid F_D) = \underset{\Psi=\hat{\Psi}}{\mathrm{argmax}} \frac{[p(F_D \mid Cyl, \Psi) p(\Psi \mid Cyl) P(Cyl)]}{p(F_D)} \quad MAP \tag{16}$$

i. Probability of a Line Impulse Vs. Noise

First consider the conditional probability of the data given a unit line impulse at some angle, $\alpha_c$. The probability density with respect to $\alpha_c$ of the output of one filter, $\alpha_i$, is given by, $$p(f_i \mid Cyl, \alpha_c) = \frac{1}{\sqrt{2\pi}\,\sigma} e^{\frac{-1}{2\sigma^2}(f_i - \hat{f}_i(\alpha_c;\varepsilon))^2} \tag{17}$$

-continued where $$\hat{f}_c(\alpha_c; \alpha_i, \varepsilon) = \rho \frac{\varepsilon}{2} \frac{(\text{Cos}^2((\alpha_c - \alpha_i)) + 2\varepsilon^2 \text{Sin}^2((\alpha_c - \alpha_i)))}{(\text{Cos}^2(\alpha_c - \alpha_i) + \varepsilon^2 \text{Sin}^2(\alpha_c - \alpha_i))^{\frac{3}{2}}}$$

Consider the joint probability, $$p(f_i, \hat{f}_i, Cyl) = \frac{1}{\sqrt{2\pi}\,\sigma} e^{\frac{-1}{2\sigma^2}(f_i - \hat{f}_i)^2} p(\hat{f}_i) P(Cyl) \quad (18)$$

It is desired to express the joint probability on $\alpha_c$ rather than on $\hat{f}_i(\alpha_c;\varepsilon)$, so that the unknown $\alpha_c$ can be marginalized away. To effect the change in variables it is necessary to compute the Jacobian of $(f_i, \hat{f}_i(\alpha_c;\varepsilon))$ with respect to $(f_i, \alpha_c)$, $$J = \begin{bmatrix} 1 & 0 \\ 0 & \frac{\partial \hat{f}_i}{\partial \alpha_c} \end{bmatrix} \quad (19)$$

The transformed joint density is given by, $$p(f_i, \alpha_c, Cyl) = \frac{1}{\sqrt{2\pi}\,\sigma} e^{\frac{-1}{2\sigma^2}(f_i - \hat{f}_i(\alpha_c;\varepsilon))^2} |J| p(\hat{f}_i(\alpha_c;\varepsilon)) P(Cyl) = \quad (20)$$

$$\frac{1}{\sqrt{2\pi}\,\sigma} e^{\frac{-1}{2\sigma^2}(f_i - \hat{f}_i(\alpha_c;\varepsilon))^2} \left|\frac{\partial \hat{f}_i}{\partial \alpha_c}\right| \frac{p(\alpha_c)}{\left|\frac{\partial \hat{f}_i}{\partial \alpha_c}\right|} P(Cyl)$$

$$p(f_i \mid \alpha_c, Cyl) = \frac{p(f_i, \alpha_c, Cyl)}{p(\alpha_c) P(Cyl)}$$

which leads to the result as stated. Note that the transformation of coordinates in the conditional density is compensated by the transformation of coordinates in the prior distribution, leaving the original density.

Figure 17A:
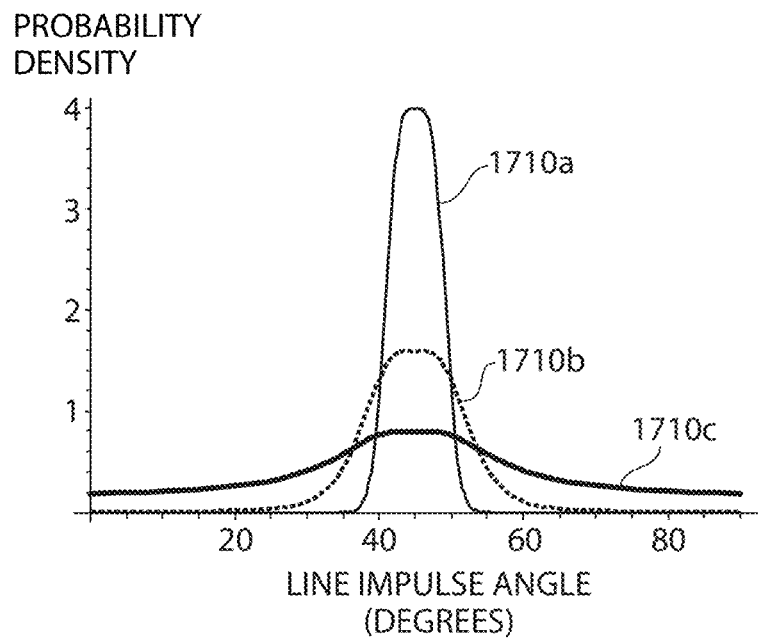
FIG. 17A illustrates probability density functions for a filter response to a line impulse at three different standard deviations $\sigma$, in accordance with one embodiment of the present invention.

FIG. 17A illustrates the conditional probability density p($f_i$|Cyl,$\alpha_c$) for a single filter response to a line impulse, $f_i=1$, $\alpha_i=45°$, $\varepsilon=0.2$. The three separate probability distributions 1710 show the conditional probability with the standard deviation, σ, varied by different amounts, characterizing the amount of noise present in the filter outputs. Since the filter output is normalized to one (i.e., $f_i=1$), the signal to noise ration is $$\frac{1}{\sigma}.$$

Probability density distribution 1710a illustrates the conditional probability with the noise level varied as σ=0.1. Probability density distribution 1710b illustrates the conditional probability with the noise level varied as σ=0.25. Probability density distribution 1710c illustrates the conditional probability with the noise level varied as σ=0.5. Note that the noise variance has a significant effect on the density function. If the noise were zero, then the density would become an impulse at 45 degrees.

Figure 17B:
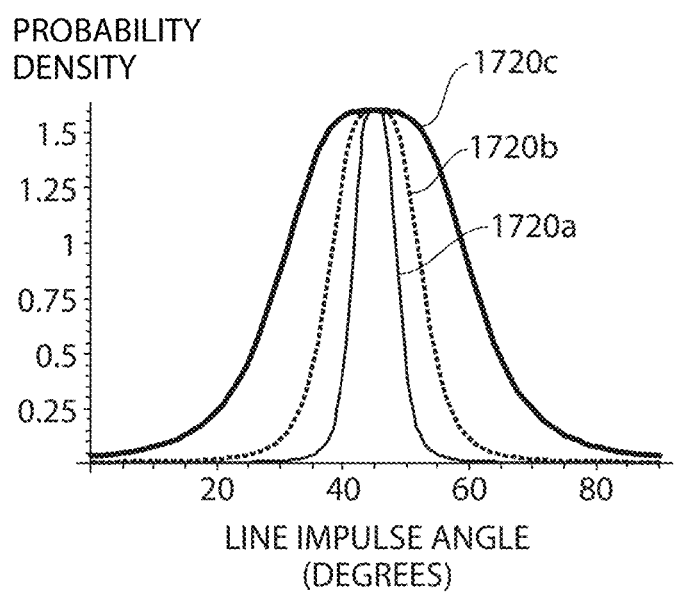
FIG. 17B illustrates probability density functions for a filter response to a line impulse at three filter sharpness values $\epsilon$, in accordance with one embodiment of the present invention.

The effect of filter sharpness is illustrated in FIG. 17B, which shows the conditional probability density for a single filter response to a unit line impulse at various filter sharpness values, ε. Probability density distribution 1720a illustrates the conditional probability with a filter sharpness of ε=0.1. Probability density distribution 1720b illustrates the conditional probability with a filter sharpness of ε=0.2. Probability density distribution 1720c illustrates the conditional probability with a filter sharpness of ε=0.4. The probability density at the peak orientation of the filter is independent of filter sharpness since the peak value is always unity, so the density is just that of a normal distribution at zero, i.e., $$\frac{1}{\sqrt{2\pi}\,\sigma}.$$

It is now possible to compare the probability of two hypotheses: H1) a line impulse is present; and H2) only noise is present. For the single filter example the posterior probability for H1 is, $$p(Cyl \mid f_i) = \frac{p(f_i \mid \alpha_c, Cyl) p(\alpha_c) P(Cyl)}{p(f_i)} \quad (21)$$

The probability for H2 is, $$p(\text{Noise} \mid f_i) = \frac{p(f_i \mid \text{Noise}) P(\text{Noise})}{p(f_i)} \quad (22)$$

The conditional probability density for an observed filter output given only noise is present is, $$p(f_i \mid \text{Noise}) = \frac{1}{\sqrt{2\pi}\,\sigma} e^{\frac{-f_i^2}{2\sigma^2}} \quad (23)$$

The probability density of the observed data is, $$p(f_i) = p(f_i \mid \text{Noise}) P(\text{Noise}) + p(f_i \mid Cyl) P(cyl) \quad (24)$$

Figure 18:
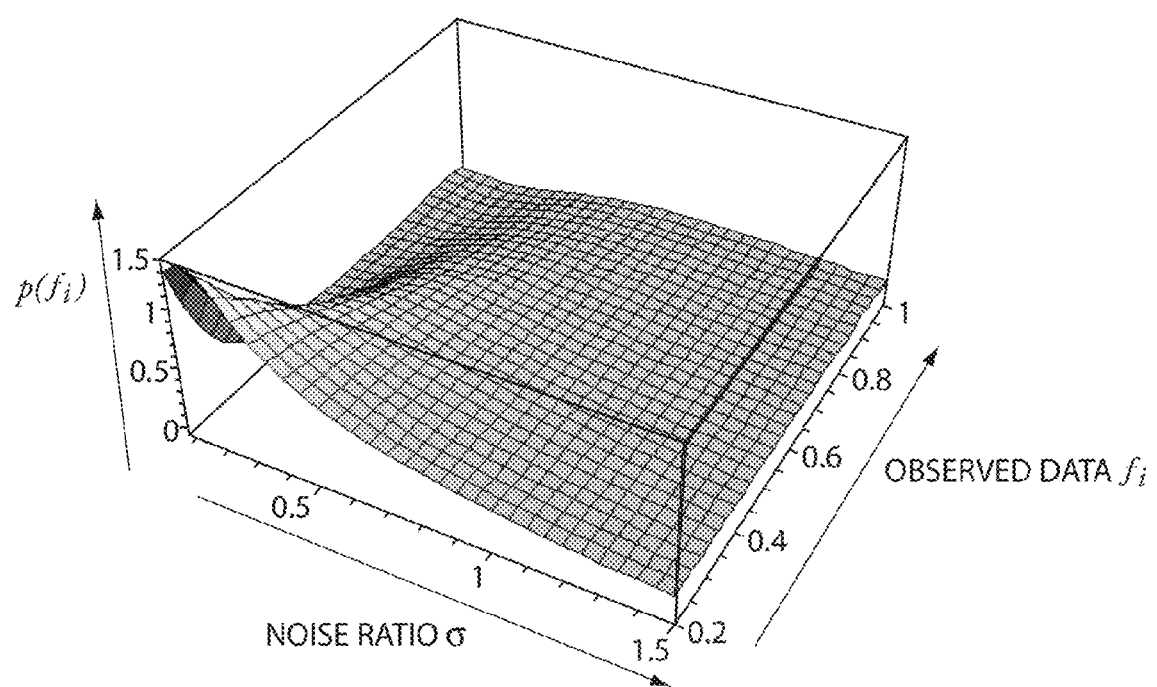
FIG. 18 illustrates a probability density function for observed data under an assumption that a cylinder hypothesis and a noise hypothesis are equally likely, in accordance with one embodiment of the present invention.

FIG. 18 illustrates the probability density function for the observed data assuming that the cylinder and the noise hypothesis are equally likely (i.e., assuming that P(Noise)=P(cyl)=0.5), with a filter sharpness of ε=0.2. As might be expected, observed filter output densities near zero are most probable since both noise and line impulses not at the peak filter response produce small observed data values.

Figure 19A:
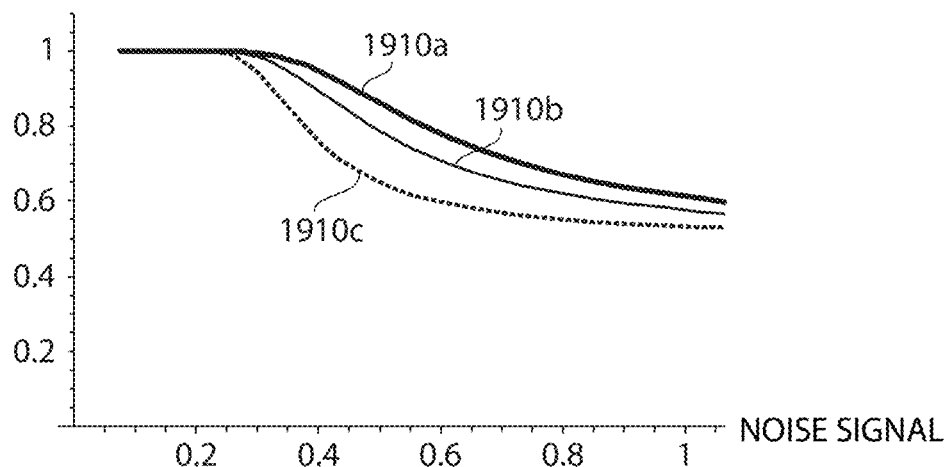
FIG. 19A illustrates the probability of a cylinder being present in the data as a function of the standard deviation of the noise for three different filter sharpness values $\epsilon$, in accordance with one embodiment of the present invention.
Figure 20:
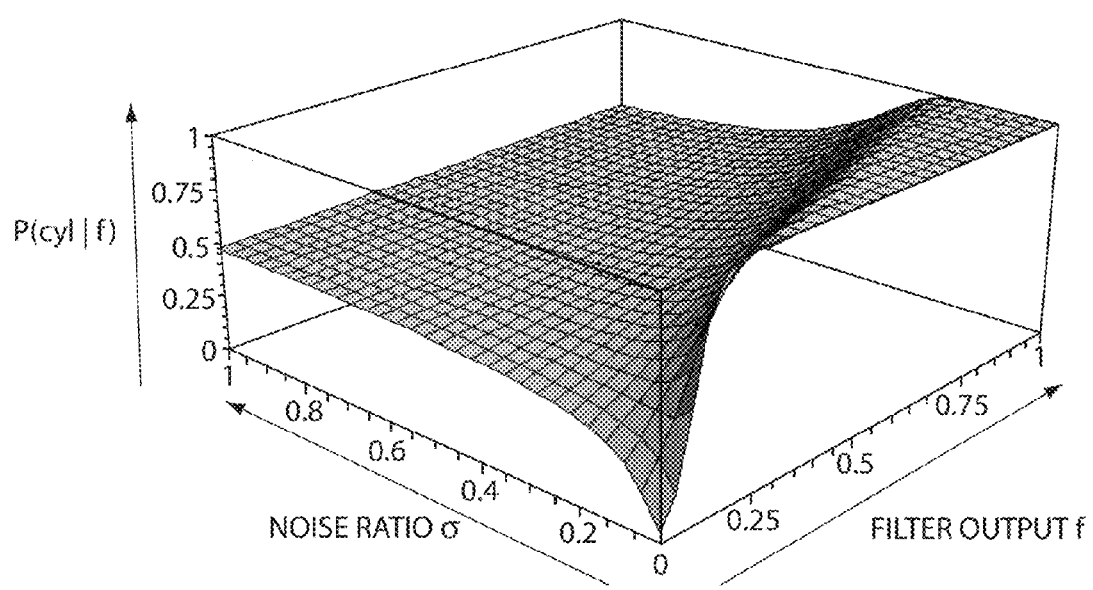
FIG. 20 illustrates the probability of a cylinder being present in the data versus noise level with a filter sharpness value of $\epsilon=0.2$, in accordance with one embodiment of the present invention.

FIGS. 19A and 20 demonstrate the probability that the filter response corresponds to a unit line impulse as a function of noise level. As the noise level increases, the probability of these two hypotheses both approach 0.5, which is their assumed prior probability. Sharper filter responses cope worse with noise than a broader filter as far as detection is concerned. The best noise performance is for the isotropic filter, i.e., ε=1.

FIG. 19A illustrates the probability of a cylinder, given that $f_i=1$, as a function the standard deviation of the noise, σ, at different filter sharpness. Probability density distribution 1910a illustrates the conditional probability with a filter sharpness of ε=1.0. Probability density distribution 1910b illustrates the conditional probability with a filter sharpness of ε=0.4. Probability density distribution 1910c illustrates the conditional probability with a filter sharpness of ε=0.1.

Figure 19B:
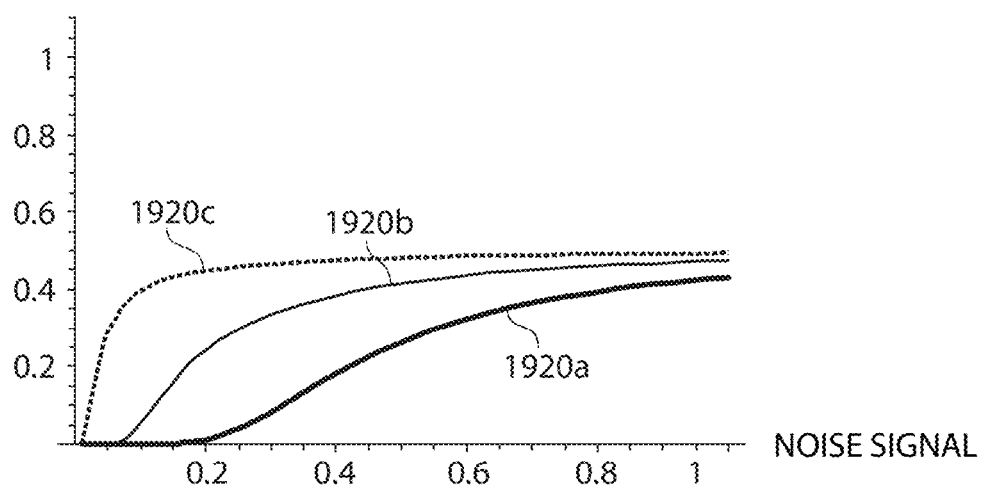
FIG. 19B illustrates the probability of a cylinder being present in the data as a function of the standard deviation of the noise for three different filter sharpness values $\epsilon$, in accordance with one embodiment of the present invention.

FIG. 19B illustrates the probability of a cylinder, given that $f_i=0.01$, as a function the standard deviation of the noise, σ, at different filter sharpnesses. Probability density distribution 1920a illustrates the conditional probability with a filter sharpness of $\epsilon=1.0$. Probability density distribution 1920b illustrates the conditional probability with a filter sharpness of $\epsilon=0.4$. Probability density distribution 1920c illustrates the conditional probability with a filter sharpness of $\epsilon=0.1$. FIG. 20 illustrates the probability of a cylinder present in the data versus noise level and filter output with a filter sharpness of $\epsilon=0.2$.

ii. Orientation Accuracy

Next, consider the accuracy of the orientation that can be determined from the filter output, once it is decided that a filter is present. The parameters of the cylinder can be determined by a number of processing methods once a cylinder has been detected. For example, a linked chain of cylinder detections may be used to determine the local orientation of the axis. In one embodiment, the cylinder orientation is determined from the filter outputs in the probabilistic framework, as analyzed below. The posterior probability density for the line impulse orientation, given that a line impulse is present is, $$p(\alpha_c | f_i, Cyl) = \frac{\frac{1}{\sqrt{2\pi}\,\sigma} e^{\frac{-1}{2\sigma^2}(f_i-\hat{f}_i(\alpha_c;\varepsilon))^2} p(\alpha_c)}{p(f_i)} \quad (25)$$

Figure 21A:
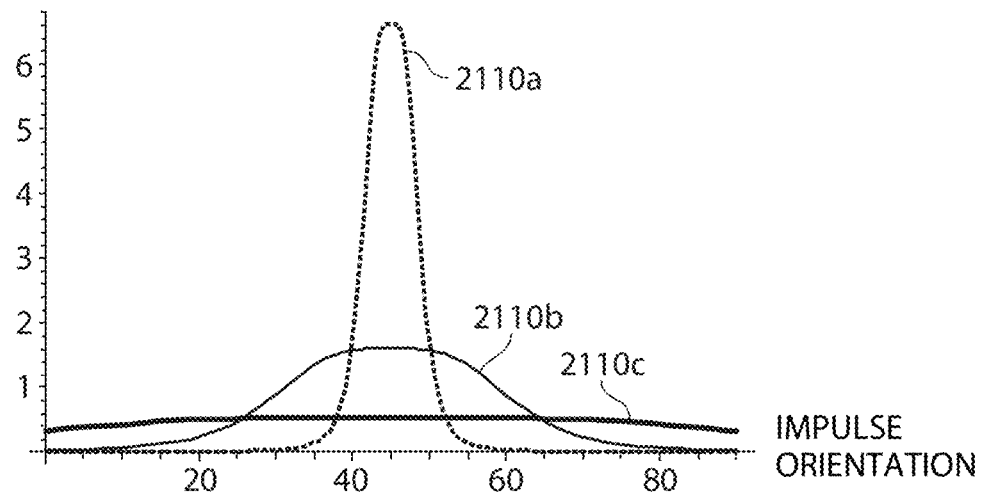
FIG. 21A illustrates the probability density of line impulse orientation for different sharpness values $\epsilon$, in accordance with one embodiment of the present invention.

FIG. 21A illustrates the probability density of line impulse orientation for $f_i=1$, $\alpha_i=45°$, and $\sigma=0.25$ and different filter sharpness values. Probability density 2110a illustrates the probability density of line impulse orientation with filter sharpness $\epsilon=0.1$. Probability density 2110b illustrates the probability density of line impulse orientation with filter sharpness $\epsilon=0.4$. Probability density 2110c illustrates the probability density of line impulse orientation with filter sharpness $\epsilon=1.0$. As shown, there is a tradeoff between noise immunity and localization of cylinder orientation.

Figure 21B:
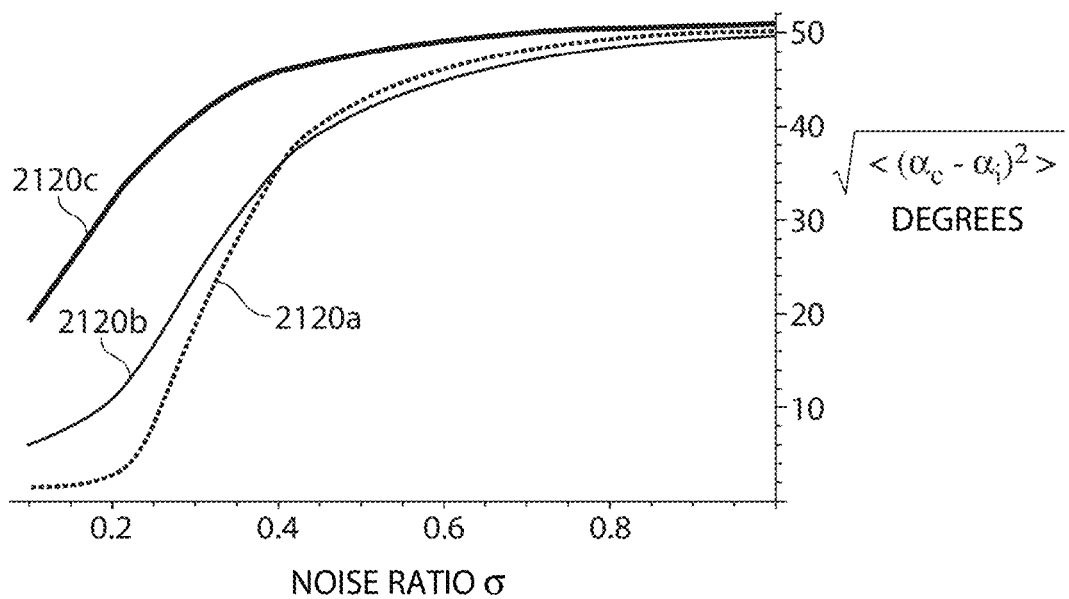
FIG. 21B illustrates the standard deviation in probable line orientation as a function of noise ratio for different sharpness values $\epsilon$, in accordance with one embodiment of the present invention.

FIG. 21B illustrates the standard deviation in probable line orientation as a function of noise ratio, σ, with different filter sharpness values, ε. Standard deviation 2120a illustrates the standard deviation in probable line orientation with a filter sharpness value of $\epsilon=0.1$. Standard deviation 2120b illustrates the standard deviation in probable line orientation with a filter sharpness value of $\epsilon=0.4$. Standard deviation 2120c illustrates the standard deviation in probable line orientation with a filter sharpness value of $\epsilon=1.0$.

iii. Multiple Filters

Multiple filter outputs and their effect on detection and orientation accuracy are explored herein. For the analysis, it will be assumed that the noise in each filter output is independent of the noise in other filter outputs. This may not be the case near the center of the filter domain, since all orientations share the same data. However, for filters with high directionality, most of the integrated response is due to the data uniquely sampled by only one filter. In any case, the first-level analysis here will not consider statistical dependence between the filter outputs.

Figure 22A:
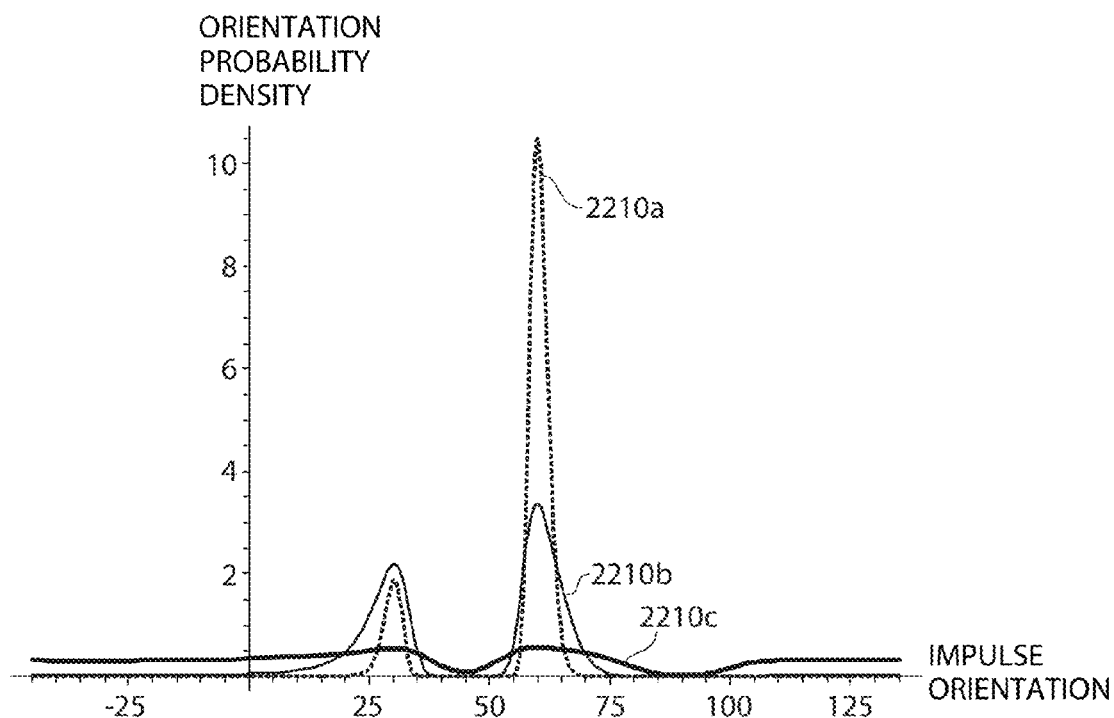
FIG. 22A illustrates the probability density for line impulse orientation with filters oriented at 45 degrees and 90 degrees for three different noise ratios, in accordance with one embodiment of the present invention.

As a first example, consider two filters with orientations of 45° and 90°. The observed data values are fixed at the filter outputs that correspond to a line impulse orientation of 60°. The resulting probability density for the unknown source orientation is shown in FIG. 22A. In particular, FIG. 22A illustrates the probability density for line impulse orientation with filters oriented at 45° and 90°. The observed filter output vector is [0.42, 0.21], corresponding to an ideal filter response to a line impulse at 60°. The probability densities are shown for various noise ratios. Probability density 2210a illustrates the probability density for line impulse orientation with a noise ratio of $\sigma=0.05$. Probability density 2210b illustrates the probability density for line impulse orientation with a noise ratio of $\sigma=0.1$. Probability density 2210c illustrates the probability density for line impulse orientation with a noise ratio of $\sigma=0.3$.

Figure 22B:
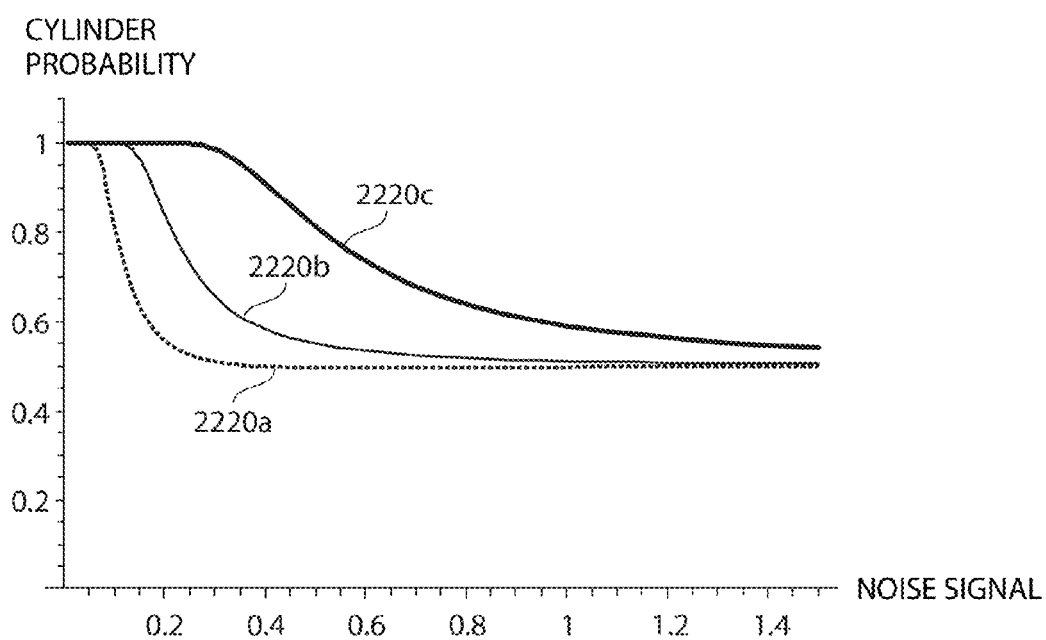
FIG. 22B illustrates cylinder probabilities over a range of line impulse orientations for three different sharpness ratios $\epsilon$, in accordance with one embodiment of the present invention.

The maximum probability is at 60°, as expected. A second peak near 30° results from similar observed filter outputs to those at 60°, i.e., [0.42, 0.11]. As the noise level increases the distinction of the correct orientation is lost. The marginal probability of a cylinder being present is shown in FIG. 22B. In particular, FIG. 22B illustrates cylinder probabilities over a range of line impulse orientations for different filter sharpness ratios ε. In particular, cylinder probability 2220a illustrates the cylinder probability over a range of line impulse orientations for $\epsilon=0.1$. Cylinder probability 2220b illustrates the cylinder probability over a range of line impulse orientations for $\epsilon=0.2$. Cylinder probability 2220c illustrates the cylinder probability over a range of line impulse orientations for $\epsilon=0.5$. As shown, sharper filters fare worse with respect to noise.

Figure 23:
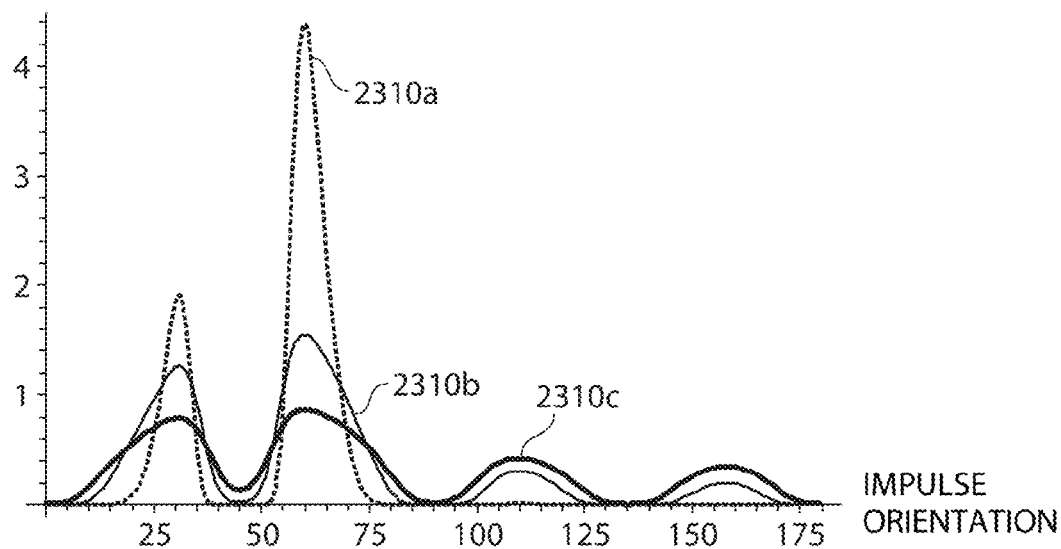
FIG. 23 illustrates the probability density for line impulse orientation with filters oriented at 0, 45, 90 and 135 degrees with a filter sharpness ratio $\epsilon=0.2$, in accordance with one embodiment of the present invention.

An additional experiment determined the localization probability density for the full set of four filter orientations spaced 45° in the meridian plane, as shown in FIG. 23. In particular, FIG. 23 illustrates the probability density for line impulse orientation with filters oriented at 0, 45, 90 and 135 degrees with filter sharpness ratio $\epsilon=0.2$. The observed filter output vector is [0.12, 0.42, 0.21, 0.10], corresponding to an ideal filter response to a line impulse at 60 degrees. Probability density 2310a illustrates orientation probability for noise ratio $\sigma=0.1$. Probability density 2310b illustrates orientation probability for noise ratio $\sigma=0.2$. Probability density 2310c illustrates orientation probability for noise ratio $\sigma=0.3$. Again, as shown, noise levels above about $\sigma=0.3$ severely limit the orientation accuracy of the filter bank. Orientations near the peak response of each filter have negligible probability density, since the observed filter outputs are far from the required values for a line impulse oriented at one of the filter orientations, i.e., [0, . . . , 1, 0, . . . 0].

iv. Point Impulse Hypothesis

Figure 24:
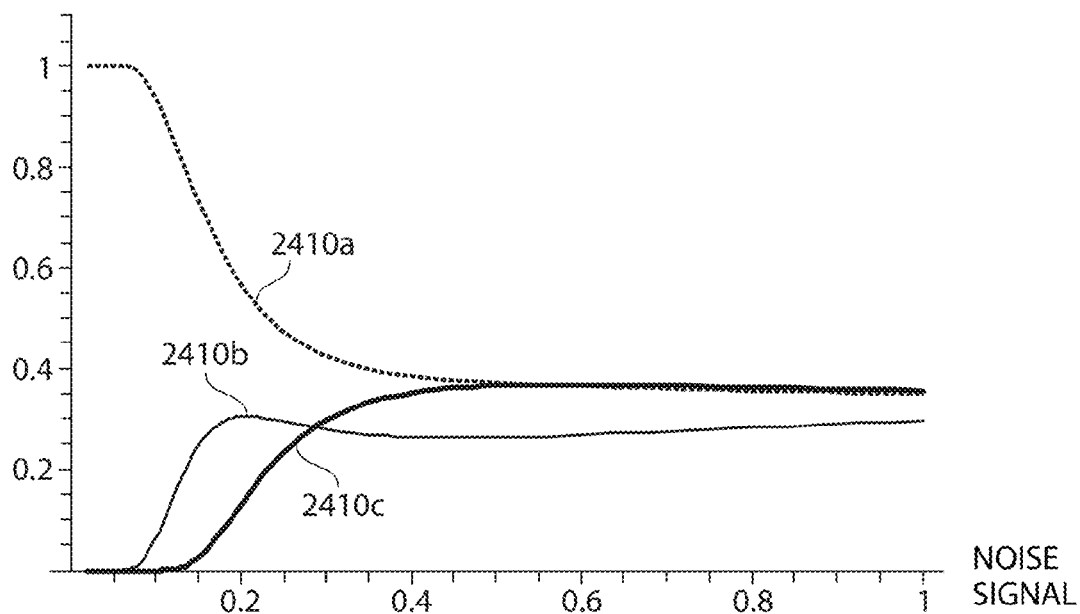
FIG. 24 illustrates the class probability for a cylinder, sphere and noise assuming each class is equally likely, in accordance with one embodiment of the present invention.

An additional hypothesis that reflects possible competition with the existence of a cylinder (expressed as a line impulse) is a point impulse at the origin of the filter. This model represents small spherical material contained within the central lobe of the filter. When the sphere is centered on the origin, all filters respond equally to the excitation. This source may be of any density, ρ, and so the ideal filter bank response to the point impulse is $F_{point}(\rho)=\rho[1, 1, \ldots, 1]$. The point impulse probability density is assumed uniform on the range, [0, 1]. An example of the variation of class probability with noise level is shown in FIG. 24. Each class was assumed equally likely, that is, P(cyl)=P(sphere)=P(noise)=⅓.

Figure 25:
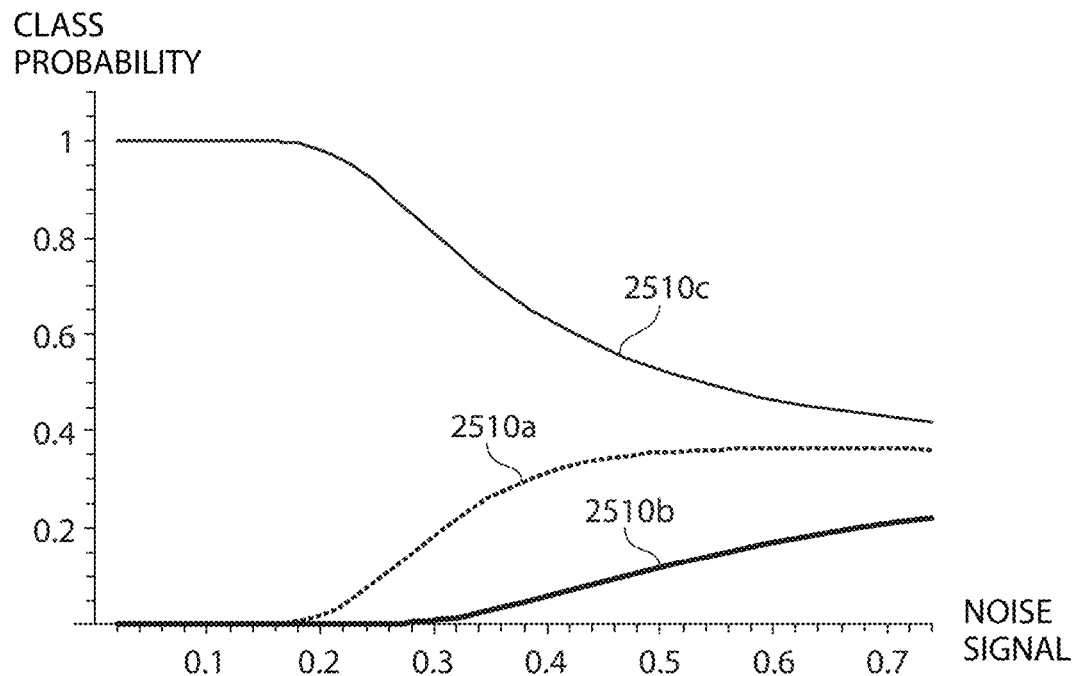
FIG. 25 illustrates the class probability for a cylinder, sphere and noise when the respective filter outputs are equal, in accordance with one embodiment of the present invention.

Class probability 2410a illustrates the class probability for a cylinder. Class probability 2410b illustrates the class probability for a sphere. Class probability 2410c illustrates the class probability for noise. The observed filter output vector is [0.12, 0.42, 0.21, 0.10], corresponding to an ideal filter response to a line impulse at 60 degrees. The spherical impulse becomes most probable if the filter outputs are all equal. An example is shown in the class probabilities illustrated in FIG. 25. The dominance of the sphere hypothesis persists to significantly higher noise levels than the cylinder hypothesis in the example of FIG. 24. Class probability 2510a illustrates the class probability for a cylinder. Class probability 2510b illustrates the class probability for a sphere. Class probability 2510c illustrates the class probability for noise. The observed filter output vector is [0.5, 0.5, 0.5, 0.5], corresponding to a spherical impulse with density, 0.5.

Figure 26:
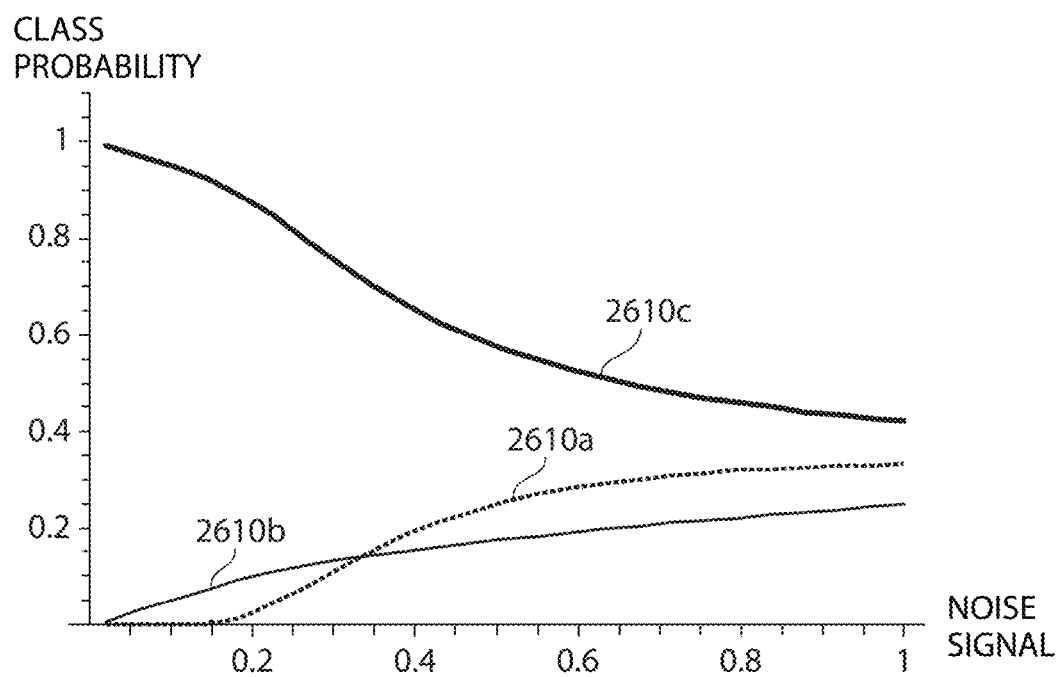
FIG. 26 illustrates the class probability for a cylinder, sphere and noise when the respective filter outputs are randomly distributed with a small variance about zero, in accordance with one embodiment of the present invention.

The noise hypothesis is favored if the outputs are randomly distributed with a small variance about zero, as shown in FIG. 26. Class probability 2610a illustrates the class probability for a cylinder. Class probability 2610b illustrates the class probability for a sphere. Class probability 2610c illustrates the class probability for noise. The observed filter output vector is [−0.08, 0.075, −0.05, 0.01], corresponding to a spherical impulse with density, 0.5.

It should be appreciated that any number or type of hypothesis for various class types may be tested. The above hypothesis testing in a Bayesian framework is described merely as one exemplary embodiment of a method for analyzing filter outputs to determine if subject matter of interest is present in the view. As discussed above, any method of analyzing the filter outputs or processing the filter data may be used, as the aspects of the invention are not limited for use with any particular analysis method or type of processing the filter data.

D. Exemplary Filters

It should be appreciated that the generalized filter model described above may be used in connection with filters of any design. In particular, a filter may be designed to respond to any subject matter in the view data associated with any structure, material, item, etc. in an object, as the aspects of the invention are limited for use with any particular filter or to detect the presence of any particular type of subject matter. As discussed above, tubular or generally cylindrical structure may be of interest when detecting the presence of such things as blood vessels in view data of a biological object, such as a patient, and the filter described in Section B illustrates one embodiment of a filter designed to respond to generally tubular structure. While any filter may be used in connection with the various aspects of the invention (e.g., from relatively simple filters such as difference and/or smoothing filters, to more complex and sophisticated filters adapted to respond to specific subject matter of interest), several exemplary filters are provided below.

Figure 27C:
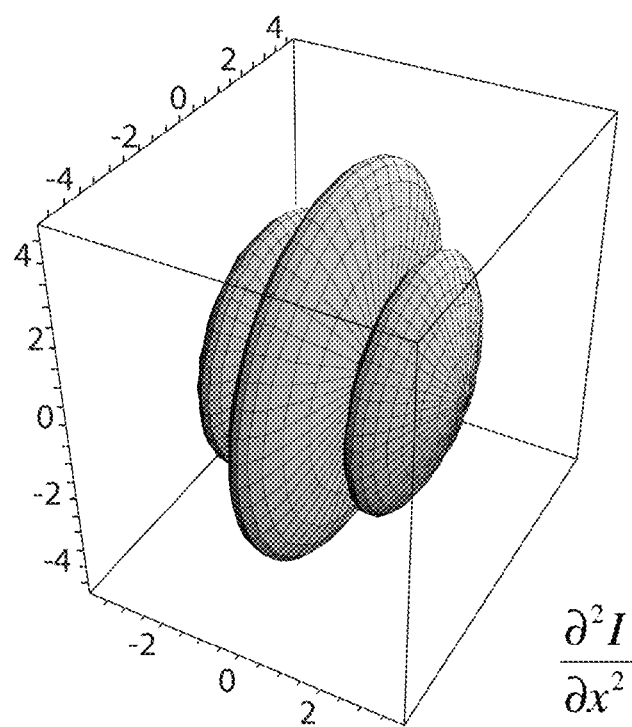
Figure 27D:
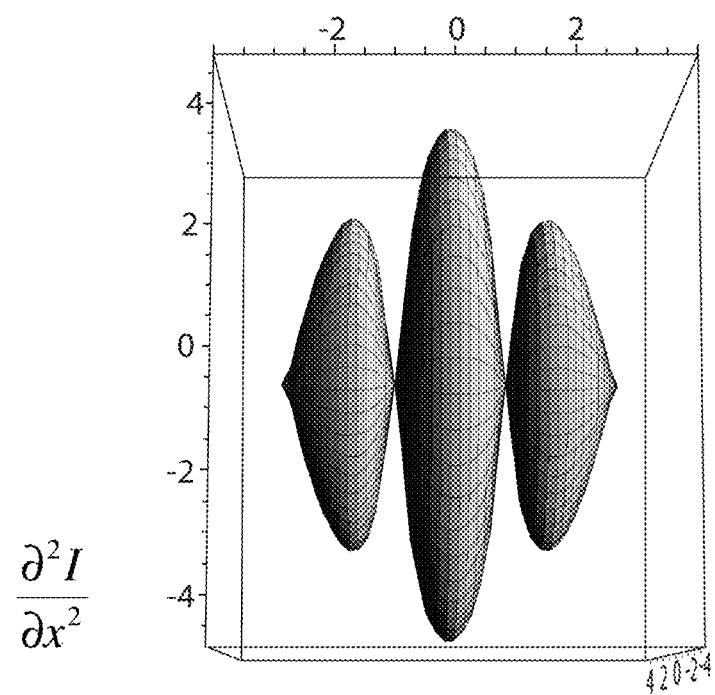
Figure 27E:
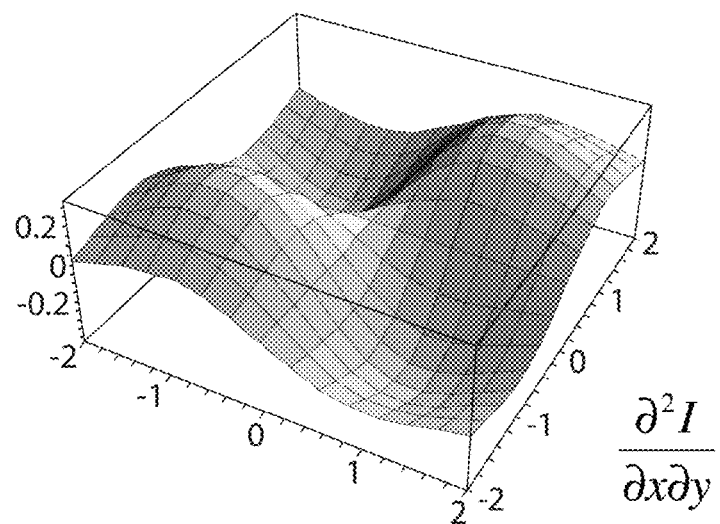
Figure 27F:
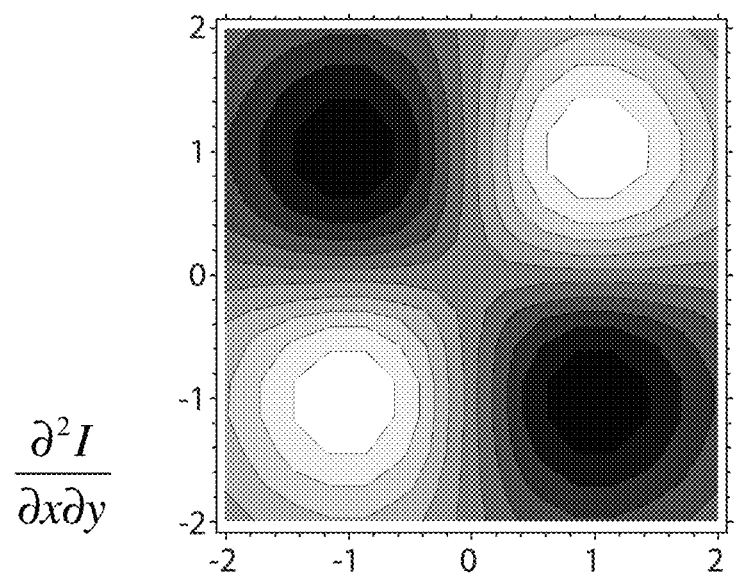

FIGS. 27B and 28B illustrate embodiments of other filter designs that may be used in connection with the various aspects of the present invention. FIG. 27B illustrates the use of the Hessian operator in designing a filter as a derivation of the Taylor Series expansion of the density as illustrated in FIG. 27A. The 3D Hessian operator is illustrated in FIG. 27B. FIGS. 27C and 27D illustrate the even function associated with the second partial derivative with respect to x and FIGS. 27E and 27F illustrate the odd function associated the partial derivative with respect to x and y. The principal directions of the output from the Hessian operator indicate the orientation of, for example, tubular structure that, when scanned, gave rise to the view data on which the filter operates.

FIG. 28B illustrates the use of steerable filters formed from an even $2^{nd}$ order polynomial (e.g., derivative of Gaussian as in the Hessian). The steerable filter, however constituted, may be rotated to form six evenly distributed directions to be used as basis filters $f(x)$. The direction cosines are illustrated in FIG. 28A. The steering equation for an arbitrary filter direction defined by the direction cosines $(\alpha, \beta, \gamma)$ is shown in FIG. 28B. The steering coefficients $k_i$ may be found by inverting the set of constraints on the monomials illustrated in FIG. 28C.

In another embodiment, a cylinder model is expanded into a set of spherical harmonics as shown in equation 26 below. The filters may be applied by using any number of harmonics. For example, up to $3^{rd}$ order harmonics may be applied as filters. Cylinder parameters may be recovered from the values of $A_{lm}$ in equation 26.

$$\tilde{I}(\rho, \theta, \phi) = \sum_{l,m} A_{lm} Y_{lm}(\theta, \phi) e^{\frac{1}{2\sigma^2}(\rho-\rho_0)^2} \quad (26)$$

As discussed above, the filters described in the embodiments herein are merely exemplary, as the aspects of the invention are not limited in this respect. Various concepts related to applying a filter to view data that varies as a function of at least one variable associated with the view data and/or concepts related to splatting or projecting filters onto view data are intended to be general and can be used with any type of filter having any type of filter function.

It should be appreciated that the generalized filter model described above may be used to filter view data obtained in any number of X-ray scanning configurations. In particular, the generalized filter model may be used with view data obtained using a cone beam, a fan beam, a pencil beam, or other beam configurations, as the aspects of the invention are not limited in this respect. For example, filtering view data according to some aspects of the present invention may result in the same operation as filtering reconstructed data (and at the higher resolution of the view data) for view data obtained using an X-ray beam having either parallel or non-parallel rays, as discussed in further detail below.

E. Filtering with Non-Parallel Beams

Figure 29A:
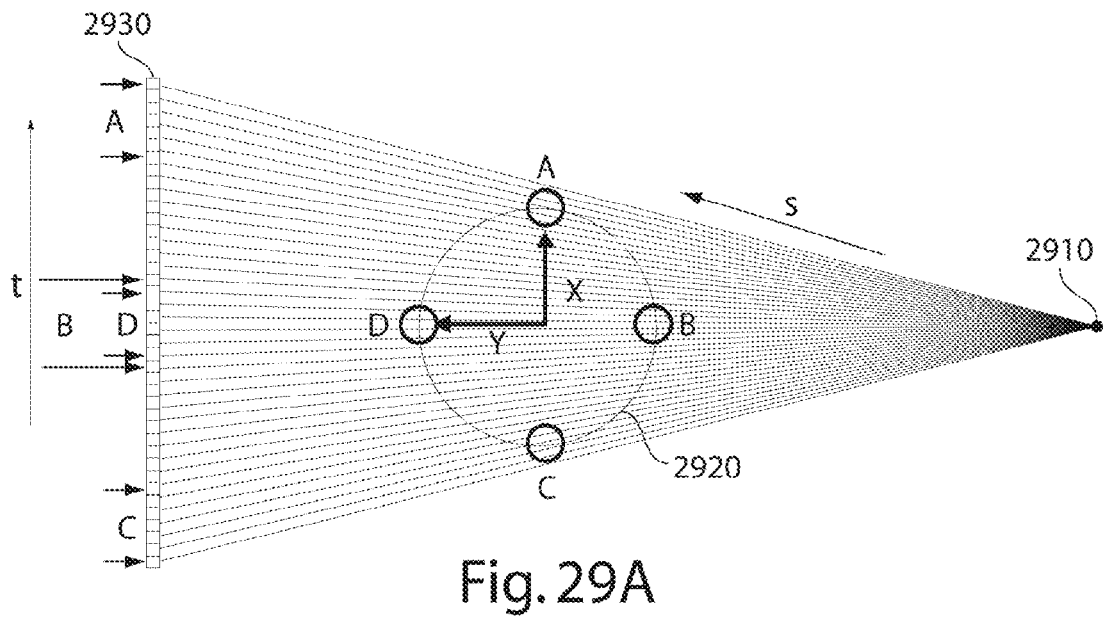
FIGS. 29A and 29B illustrate projections of an object in non-parallel ray and parallel ray environments, respectively, in accordance with one embodiment of the present invention.

FIG. 29A illustrates a filter 2920 being splat (e.g., projected) onto plane 2930 using non-parallel X-rays emanating from a source 2910. As shown in FIG. 29A, X-ray imaging with a fan beam (or cone beam) geometry causes an apparent change in scale of the shadow of an object (e.g., an object being scanned, or a filter being splatted) on the plane 2930, for example, the relative scale of disks A, B, C and D are 7, 8, 7 and 6, respectively. There is over a 30 percent change in scale from the point on the orbit closest to source 2910 to the opposite point nearest plane 2930 (e.g., a detector array, a plane of view data, etc.). In addition, there is a change in the orientation of the rays with respect to position, due to the angular spread of the rays.

According to one approach, filter splatting may be performed by taking line integrals through the filter in correspondence to the same process by which the original X-ray projection is formed. To determine the effect of non-parallel rays (e.g., a fan beam geometry) on the resulting filter response, the relationship between the non-parallel beam and parallel beam scenarios is examined below.

i. Parallel Beam Filtering

Figure 29B:
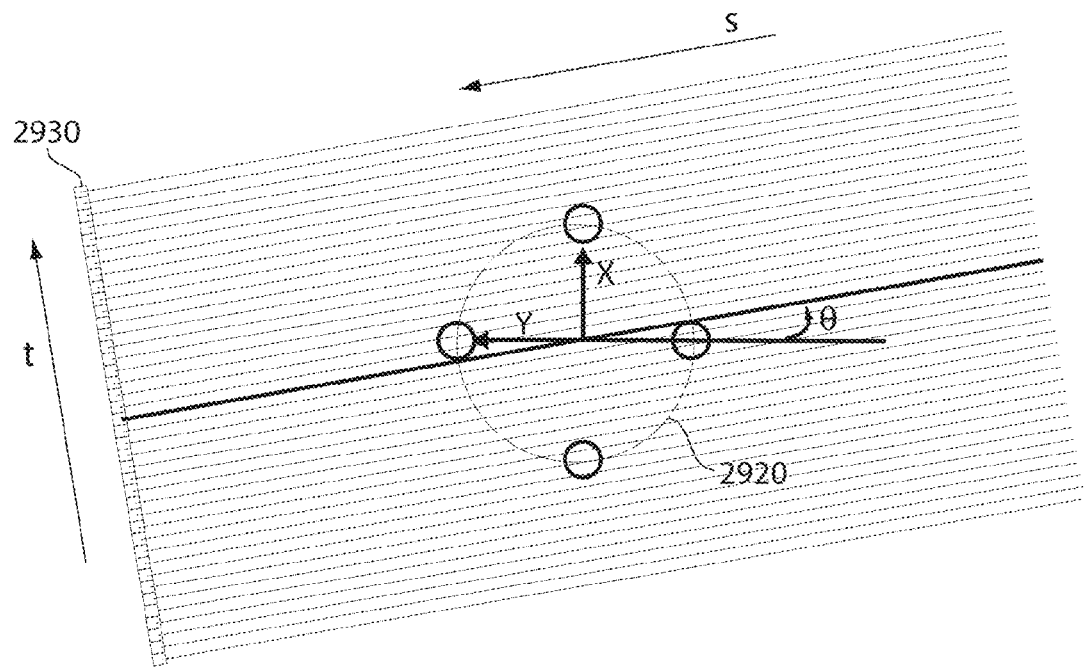

FIG. 29B illustrates a filter 2920 being projected or splat onto plane 2930 using parallel rays. In general, parallel beam projection produces the Radon transform for a given projection angle, $\theta$, as shown in FIG. 29B. The projection of a structure (e.g., structure being scanned, a filter being splatted, etc.) in the X-Y plane is formed by line integration along the s direction forming a 1-d image as a function of t. That is, $$\begin{bmatrix} t \\ s \end{bmatrix} = \begin{bmatrix} \cos\theta & \sin\theta \\ -\sin\theta & \cos\theta \end{bmatrix} \begin{bmatrix} x \\ y \end{bmatrix} \quad (27)$$

The 1-d image (−log image) of a density function is given by, $$\bar{\mu}_\theta(t) = \int_{-\infty}^{\infty} \mu(t,s)\,ds \quad (28)$$

The symbol $\bar{\mu}_\theta$ denotes the parallel X-ray projection of the corresponding 2-d function $\mu$ along direction $\theta$. Suppose that the density function is filtered by a 2-d operator, $f(t-u, s-v)$, leading to the projected convolution, $$\overline{(\mu*f)}_\theta(t) = \int_{-\infty}^{\infty}\left[\int_{-\infty}^{\infty}\int_{-\infty}^{\infty} \mu(u,v) f(t-u, s-v)\,du\,dv\right] ds \quad (29)$$

The order of integration can be reversed to produce, $$\begin{aligned}\overline{(\mu*f)}_\theta(t) &= \int_{-\infty}^{\infty}\left[\int_{-\infty}^{\infty} \mu(u,v)\left[\int_{-\infty}^{\infty} f(t-u, s-v)\,ds\right] dv\right] du \\ &= \int_{-\infty}^{\infty}\left[\int_{-\infty}^{\infty} \mu(u,v)\,dv\, \overline{f}_\theta(t-u)\right] du \\ &= \int_{-\infty}^{\infty} \bar{\mu}_\theta(u)\,\overline{f}_\theta(t-u)\,du\end{aligned} \quad (30)$$

That is, the projection of the convolution is the convolution of the projection for the parallel beam case, which is an assumption underlying embodiments of the filter splat process of model-based reconstruction.

a. Parallel Beam Reconstruction

Define a ramp filter on the projection image, given by, $$g(t) = \int_{-\infty}^{\infty} |\omega| e^{2\pi i \omega t}\,d\omega \quad (31)$$

It can be shown via the Fourier slice theorem that filtered back projection will produce the original 2-d response. That is, $$(\mu*f)(x,y) = \int_0^\pi \int_{-\infty}^{\infty} g(x\cos\theta + y\sin\theta - t)\left(\int_{-\infty}^{\infty} \bar{\mu}_\theta(u)\,\overline{f}_\theta(t-u)\,du\right) dt\,d\theta \quad (32)$$

is an exact reconstruction of the original filtered density function. It should be noted that the definition of the ramp filter is not convergent. Typically a windowing function is applied to $|\omega|$, which renders $g(t)$ well-defined. As long as the spatial frequencies of $(\mu*f)$ vanish outside the window then the reconstruction will remain exact. In practice there are not a continuous set of views but instead a discrete set of projections taken at $\theta_i$. The discrete form of filtered back projection can be rearranged as, $$\begin{aligned}(\mu*f)(x,y) &= \\ \sum_i &\left(\int_{-\infty}^{\infty} \bar{\mu}_{\theta_i}(u)\int_{-\infty}^{\infty} g(x\cos\theta_i + y\sin\theta_i - t)\overline{f}_{\theta_i}(t-u)\,dt\right) du = \\ \sum_i &\left(\int_{-\infty}^{\infty} \bar{\mu}_{\theta_i}(u)\int_{-\infty}^{\infty} g(x\cos\theta_i + y\sin\theta_i - t)\overline{f}_{\theta_i}(t-u)\,dt\right) du.\end{aligned} \quad (33)$$

Define, $$h(t_0(\theta_i) - u) = \int_{-\infty}^{\infty} g(t_0(\theta_i) - t)\overline{f}_{\theta_i}(t-u)\,dt \quad (34)$$

where $t_0(\theta_i) = x_0\cos\theta_i + y_0\sin\theta_i$ as shown in FIG. 29B. The function, $t_0(\theta_i)$ is the usual sinogram that plots the center of the projected filter response with projection angle over the orbit. Thus, the reconstructed 2-d filter response at $(x_0, y_0)$ is given by, $$(\mu*f)(x_0, y_0) = \sum_i \int_{-\infty}^{\infty} \bar{\mu}_{\theta_i}(u)\,h(t_0(\theta_i) - u)\,du \quad (35)$$

Note that this result does not depend on uniform or even known values of $\theta_i$. As long as the sinogram position $t_0(\theta_i)$ corresponds to the projection of $(x_0, y_0)$, the summation will represent the discrete reconstruction of the filtered density at that point. It should be appreciated that if the angular distribution of discrete orientations is too non-uniform and too sparse the reconstruction will have artifacts.

ii. Fan Beam Mapping

The relationship between the X-Y coordinate system and the t-s coordinate system in the case of fan beam geometry can be represented by a projective mapping. The projection of a world point (x, y) is given by, $$\begin{bmatrix} wt \\ w \end{bmatrix} = \begin{bmatrix} f & t_p \\ 0 & 1 \end{bmatrix}\begin{bmatrix} \cos\theta & \sin\theta & 0 \\ -\sin\theta & \cos\theta & \dfrac{f}{2} \end{bmatrix}\begin{bmatrix} x \\ y \\ 1 \end{bmatrix} \quad (36)$$

The mapping from the line y=0 to t is given by, $$\begin{bmatrix} wt \\ w \end{bmatrix} = \begin{bmatrix} f & t_p \\ 0 & 1 \end{bmatrix}\begin{bmatrix} \cos\theta & 0 \\ -\sin\theta & \dfrac{f}{2} \end{bmatrix}\begin{bmatrix} x \\ 1 \end{bmatrix} \quad (37)$$

which is a 1-d projective transformation on the line.

a. Affine Approximation to the Fan Beam

Figure 30A:
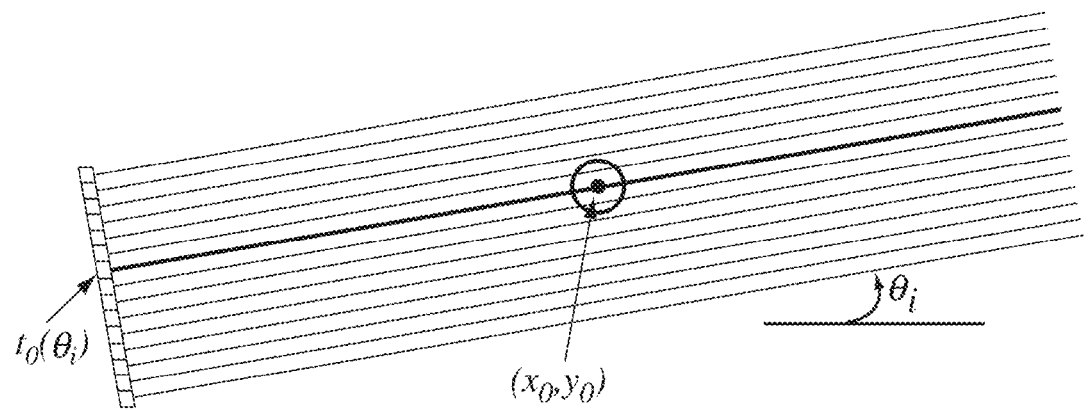
FIGS. 30A and 30B illustrate projections of an object in non-parallel ray and parallel ray environments, respectively, in accordance with one embodiment of the present invention.
Figure 30B:
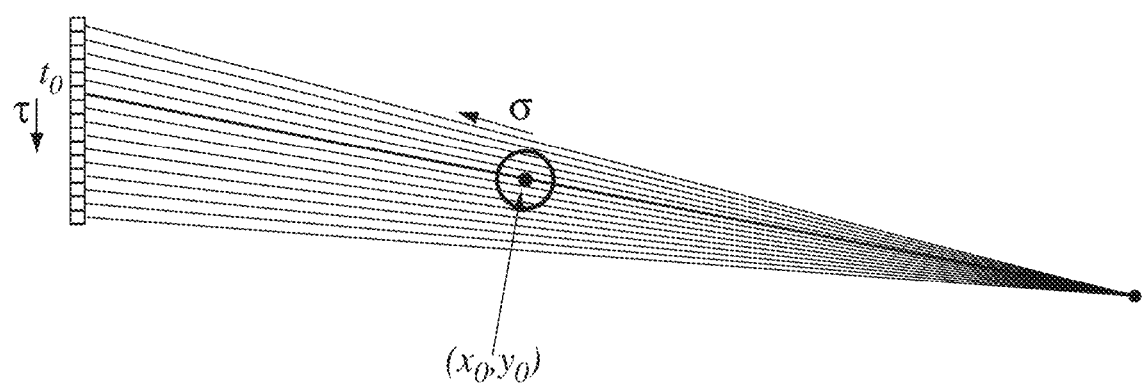

In filters with a relatively limited spatial extent, the mapping can be expanded about a point $(x_0, y_0)$ as shown in FIGS. 30A and 30B. In this local region, it is assumed that the rays from the X-ray source are approximately parallel and that the projective scale factor, w, is constant over the filter domain. This follows since, $$\begin{aligned}t - t_p &= \dfrac{f(x\cos\theta + y\sin\theta)}{-x\sin\theta + y\cos\theta + \dfrac{f}{2}} = \dfrac{f((x_0 + \Delta x)\cos\theta + (y_0 + \Delta y)\sin\theta)}{-(x_0 + \Delta x)\sin\theta + (y_0 + \Delta y)\cos\theta + \dfrac{f}{2}} \\ &\approx \dfrac{f(x_0\cos\theta + y_0\sin\theta) + f(\Delta x\cos\theta + \Delta y\sin\theta)}{\left(-x_0\sin\theta + y_0\cos\theta + \dfrac{f}{2}\right)}\end{aligned} \quad (38)$$

if $$\Delta x, \Delta y \ll \left(-x_0\sin\theta + y_0\sin\theta + \dfrac{f}{2}\right). \quad (39)$$

Thus, $$\begin{bmatrix} w\tau \\ w \end{bmatrix} \approx \begin{bmatrix} f & 0 \\ 0 & 1 \end{bmatrix}\begin{bmatrix} \cos\theta & \sin\theta & (x_0\cos\theta + y_0\sin\theta) \\ 0 & 0 & \left(-x_0\sin\theta + y_0\cos\theta + \dfrac{f}{2}\right) \end{bmatrix}\begin{bmatrix} \Delta x \\ \Delta y \\ 1 \end{bmatrix}, \quad (40)$$

where τ=t−t₀ and the projection is an affine projection. The projected affine center is given by, $$t_0 = \frac{f(x_0 \cos\theta + y_0 \sin\theta)}{\left(-x_0 \sin\theta + y_0 \cos\theta + \frac{f}{2}\right)} + t_p. \quad (41)$$

The affine projection of the filter region is identical to the parallel projection case, except that there is a scaling in the image by a factor, a. The resulting local image coordinate, τ, is given by, $$\tau = \frac{wt}{w} = \frac{f(\Delta x \cos\theta + \Delta y \sin\theta)}{-x_0 \sin\theta + y_0 \cos\theta + \frac{f}{2}} = \quad (42)$$

$$\frac{f(\tau_{para})}{-x_0 \sin\theta_{para} + y_0 \cos\theta_{para} + \frac{f}{2}} = a\tau_{para}.$$

The variable $\tau_{para}$ is the projection coordinate that corresponds to a true parallel projection at point $(x_0, y_0)$. Note that under this approximation, the ray arc length is the same as in the parallel beam case but the orientation of the rays is now different from the orientation specified by the parallel projection rotation angle, $\theta_{para}$. The actual orientation is given by, $$\theta = \theta_{para} + \mathrm{Tan}^{-1}\left(\frac{t_0 - t_p}{f}\right). \quad (43)$$

b. Correcting the Affine Mapping

There are two effects of the affine mapping to consider. First, the difference between θ and $\theta_{para}$. This effect of perspective orientation changes may be ignored. In one approach, a 2-d point is ray traced and then the 1-d filter splat is computed for that image point using the full perspective fan-beam projection geometry. This splatting process ensures that $t_0(\theta_i)$ corresponds to $(x_0, y_0)$. Second, the scale factor a. To investigate the effect of scale, consider the basic projection convolution relation in local coordinates centered on $t_0(\theta_i)$, $$\overline{\mu_\theta * f_\theta}(0) = \int_{-\infty}^{\infty} \overline{\mu_\theta}(u) \overline{f_\theta}(-u) du \quad (44)$$

Because of the affine scale factor, what is actually computed in one embodiment of the algorithm is, $$\overline{\mu_\theta * f_\theta}_{\mathrm{affine}}(0) = \int_{-\infty}^{\infty} \overline{\mu_\theta}\left(\frac{u}{a}\right) \overline{f_\theta}\left(-\frac{u}{a}\right) du \quad (45)$$

where this convolution is centered on $t'_0(\theta_i)$, the projection of $(x_0, y_0)$ under the affine approximation. Defining a new variable of integration, $$\overline{\mu_\theta * f_\theta}_{\mathrm{affine}}(0) = a \int_{-\infty}^{\infty} \overline{\mu_\theta}(v) \overline{f_\theta}(-v) dv = a\overline{\mu_\theta * f_\theta}(0). \quad (46)$$

So ignoring the back projection filter, $$g(t) = \int_{-\infty}^{\infty} |\omega| e^{2\pi i \omega t} d\omega,$$

the current filtering dot products may be corrected by dividing out the scale factor, that is, $$\overline{\mu_\theta * f_\theta}(t_0) = \frac{1}{a}\overline{\mu_\theta * f_\theta}_{\mathrm{affine}}(t'_0). \quad (47)$$

In order to apply the ramp back projection filter, g(t), the integral below may need to be interpreted, $$h_{\mathrm{affine}}\left(-\frac{u}{a}\right) = \int_{-\infty}^{\infty} g(-t)\overline{f}_{\theta_i}\left(\frac{t-u}{a}\right) dt. \quad (48)$$

Again, define a change in variables as, $$h_{\mathrm{affine}}\left(-\frac{u}{a}\right) = a \int_{-\infty}^{\infty} g(-av) \overline{f}_{\theta_i}\left(v - \frac{u}{a}\right) dv \quad (49)$$

where $$v = \frac{t}{a}.$$

Thus, to get the desired result, the domain of the ramp filter may be scaled according to the affine scale factor. That is, a stretched version of g(t) is defined, $g_a(t) = g(t/a)$. Then, a new form for $$h_{\mathrm{affine}}\left(-\frac{u}{a}\right)$$

may be constructed, $$\tilde{h}_{\mathrm{affine}}\left(-\frac{u}{a}\right) = a \int_{-\infty}^{\infty} g_a(-av) \overline{f}_{\theta_i}\left(v - \frac{u}{a}\right) dv = a \int_{-\infty}^{\infty} g(-v) \overline{f}_{\theta_i}\left(v - \frac{u}{a}\right) dv. \quad (50)$$

Thus, to get the desired composite filter, compute:

$$\int_{-\infty}^{\infty} g(-v) \overline{f}_{\theta_i}\left(v - \frac{u}{a}\right) dv = \frac{1}{a} \tilde{h}_{\mathrm{affine}}\left(-\frac{u}{a}\right). \quad (51)$$

Accordingly, by using an affine approximation to the parallel beam scenario, computations may be significantly reduced. In some embodiments, processing speeds may be increased by an order of magnitude. However, increased processing speeds are not a limitation on the aspects of the invention. It should be appreciated that the above illustrates one example of performing filtering on view data for a non-parallel beam environment. However, other methods may be used, as the aspects of the invention are not limited in this respect. For example, while in some embodiments filtering the view data may perform the same operation as filtering reconstructed data (but at the higher resolution of the view data), other embodiments of filtering the view data may perform separate operations, as the aspects of the invention are not limited in this respect.

It should be appreciated that the view data operated on in methods of the various embodiments described herein may be at the maximum resolution that a given X-ray scanning device can generate. For example, various factors such as the number of detectors in the X-ray scanning device (or the sampling rate of a detector array), the angle interval over which the data is obtained, etc., limit the resolution of the view data. As discussed above, the resolution of the view data exceeds the resolution of images reconstructed from the data. For example, the resolution of the view data may be up to five times the resolution of the reconstructed image data, or more. Accordingly, by operating directly on the view data, various aspects of the invention may facilitate detection of structure at a higher resolution than available by detection methods applied to conventional reconstructed images.

For example, conventional reconstructed data computed from view data obtained by large object X-ray devices (i.e., devices other than microCT devices, such as those suitable for scanning portions of the human anatomy in situ) may be unable to resolve structure below 500 microns. By detecting structure via direct processing of the view data according to methods of the present invention described herein, structures may be detected having dimensions below 500 microns, more preferably below 250 microns, more preferably below 100 microns, and even more preferably below 50 microns.

As discussed above, microCT may be capable of providing view data at a resolution an order of magnitude or more higher than large object X-ray devices. Conventional reconstructed data computed from view data obtained by microCT devices may be unable to resolve structure below 50 microns. By detecting structure via direct processing of the view data according to methods of the present invention described herein, structures may be detected below 50 microns, more preferably below 25 microns, more preferably below 10 microns, and even more preferably below 5 microns.

It should be appreciated that optimizing or otherwise updating a configuration via comparisons with the view data is different than detecting features in the view data to determine a value for one or more model parameters. Detecting a feature involves gleaning information directly from the view data itself as opposed to conventional techniques for optimizing a model to view data, whereby any information about the view data is determined indirectly through the use of the model.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed function. The one or more controller can be implemented in numerous ways, such as with dedicated hardware, or with general purpose hardware (e.g., one or more processor) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code.

In this respect, it should be appreciated that one embodiment of the invention is directed to a computer readable medium (or multiple computer readable media) (e.g., a computer memory, one or more floppy discs, compact discs, optical discs, magnetic tapes, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

It should be understood that the term "program" is used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. The invention is capable of other embodiments and of being practiced or of being carried out in various ways. In particular, various aspects of the invention may be used with models of any type to detect any type of feature in the view data and is not limited to any particular model, to modeling any particular type of structure, or to any detecting any particular type of feature, property or characteristic. Accordingly, the foregoing description and drawings are by way of example only.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. An apparatus adapted to detect subject matter of interest in view data obtained by scanning an object, the apparatus comprising:
   at least one input adapted to receive the view data; and
   at least one controller, coupled to the at least one input, the
      at least one controller adapted to generate a three-
      dimensional filter adapted to respond to the subject matter of interest, splat the filter onto a portion of the view data in two dimensions to provide a filter splat, and perform at least one operation on the portion of the view data using the filter splat to facilitate determining whether the subject matter of interest is present in the portion of the view data.

2. The apparatus of claim 1 wherein the at least one controller comprises means for generating the three-dimensional filter, means for splatting the filter onto the portion of the view data in two dimensions, and means for performing the at least one operation on the portion of the view data.

3. The apparatus of claim 1, wherein the at least one controller determines a response to the three-dimensional filter, and, based on the response, updates at least one parameter of the three-dimensional filter to be more responsive to the subject matter of interest in the view data.

* * * * *